(12) United States Patent
Jørgensen et al.

(10) Patent No.: US 6,399,347 B1
(45) Date of Patent: Jun. 4, 2002

US006399347B1

(54) RHAMNOGALACTURONAN HYDROLASES

(75) Inventors: Per Linå Jørgensen; Kirk Schnorr, both of Copenhagen; Lene Nonboe Andersen, Allerød; Martin Schülein, Copenhagen; Helle Outtrup, Balleruf, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/311,626

(22) Filed: May 13, 1999

Related U.S. Application Data

(63) Continuation of application No. PCT/DK99/00244, filed on May 3, 1999.
(60) Provisional application No. 60/084,358, filed on May 5, 1998.

(30) Foreign Application Priority Data

May 1, 1998 (DK) ............................................. 0608/98

(51) Int. Cl.⁷ .......................... C12N 9/26; A23K 1/165; C11D 7/42
(52) U.S. Cl. .......................... 435/200; 426/61; 510/392
(58) Field of Search .......................... 435/200; 426/61; 510/392

(56) References Cited

U.S. PATENT DOCUMENTS 5,716,849 A * 2/1998 Ligon et al. ................. 435/419

FOREIGN PATENT DOCUMENTS

| EP | 0 570 075 | 11/1993 |
| JP | 10-33169 | 2/1998 |
| WO | WO 92/19728 | 11/1992 |
| WO | WO 94/20612 | 9/1994 |
| WO | WO 95/34223 | 12/1995 |
| WO | 99/57255 | * 11/1999 |

OTHER PUBLICATIONS

Parkhill et al. EMBL Accession SC5C7. Sep. 1998.*
F. Kunst et al. "The Complete Genome Sequence of the Gram–Positive Bacterium Bacillus subtilis", Nature 390: 249–256. Nov. 1997.*
Kunst et al., Database EMBL accession No. 031526, XP–002091959 (Jan. 1998).
Kunst et al. Database EMBL accession No. 031527, XP–002091960 (Jan. 1998).
Kofod et al., The Journal of Biological Chemistry, vol. 269, No. 46, pp. 29182–29189 (Nov. 18, 1994).
Kauppinen et al., The Journal of Biological Chemistry, vol. 270, No. 6, pp. 27172–27178 (Nov. 10, 1995).
Azadi et al., Glycobiology, vol. 5, No. 8, pp. 783–789 (1995).
Mutter et al., Plant Physiol, vol. 110, pp. 73–77 (1996).
Mutter et al., Plant Physiol, vol. 117, pp. 141–152 (1998).
Mutter et al., Carbohydrate Research, vol. 311, pp. 155–164 (1998).
Abstract of Japan No. JP 10033169 Dewent WPI Accession No. 98–172089 (1998).

* cited by examiner

Primary Examiner—Rebecca E. Prouty
(74) Attorney, Agent, or Firm—Elias Lambiris; Jason Garbell

(57) ABSTRACT

The present invention is directed to isolated enzymes exhibiting rhamnogalacturonan hydrolase activity, to nucleic acids encoding such enzymes, and to methods of producing such enzymes. The present invention is also related to detergent and animal feed compositions, compositions and methods for treating cellulosic materials, such as fibers, compositions and methods for preparing fruit or vegetable products, and compositions and methods for preparing wine and juice.

10 Claims, 14 Drawing Sheets

RHAMNOGALACTURONAN HYDROLASES

CROSS-REFERENCE TO RELATED APPLICATIONS

This application is a continuation application of PCT/DK99/00244 filed May 3, 1999 and claims priority under 35 U.S.C. 119 of U.S. provisional application No. 60/084,358 filed May 5, 1998 and Danish application no. 0608/98 filed May 1, 1998, the contents of which are fully incorporated herein by reference.

BACKGROUND OF THE INVENTION

1. Field of the Invention

The present invention relates to microbial enzymes capable of degrading the rhamnogalacturonan backbone in hairy regions of pectins, more specifically to novel families of microbial rhamnogalacturonan hydrolases and the genes encoding such enzymes; to a method of producing such enzymes; and to methods for using such enzymes in the textile, detergent, animal feed and cellulose fiber processing industries.

2. Description of the Related Art

Pectic polysaccharides constitute the major matrix polysaccharides in the middle lamella and primary cell wall of dicotyledonous plants (Carpita and Gibeaut, 1993). The main backbone in pectins can be divided into linear homogalacturonan (smooth) regions of up to 200 residues of (1,4)-linked alpha-D-galacturonic acid (GalUA), and highly branched rhamnogalacturonan (hairy) regions consisting of a backbone of repeating alpha-(1,2)-L-Rha-alpha-(1,4)-D-GalUA disaccharide units (Carpita and Gibeaut, 1993; O'Neill et al., 1990; Thibault et al., 1993). The hydroxyl at the C-4 position of the rhamnose residues serves as the attachment point for the side chains (hairs), consisting mainly of neutral oligosaccharides, such as arabinan, galactan and/or arabinogalactan (Carpita and Gibeaut, 1993; O'Neill et al., 1990; Schols et al., 1990). In addition, the GalUA residues in the backbone may be acetyl esterified at the C-2 or C-3 position or methyl esterified at the carboxy group (Carpita and Gibeaut, 1993; Schols et al., 1990).

The distribution and composition of the side chains vary considerably between different cell types and physiological states, but in general about half of the rhamnosyl units in the rhamnogalacturonan regions have side chains attached. The galactan side chains are in most plants type 1 galactans, which are composed of β-1,4 linked galactopyranose with some branching points and a length of up to 60 saccharide units (DP60). Arabinofuranose residues or short arabinan oligomers can be attached to the galactan chain at the o-3 of the galactosyl unit, thus named arabinogalactan. Galactans (or arabinogalactans) have an important function in the primary cell wall, where they interact with other structural components of the cell wall such as xyloglucans or arabinoxylans. Thus they possibly serve to anchor the pectic matrix in the cell wall. (Carpita & Gibeaut, 1993, Plant J., 3, 1–30; O'Neill et al., 1990, Methods in Plant Biochemistry, 415–441; Selvendran, 1983, The Chemistry of Plant Cell Walls. Dietary Fibers; Hwang et al., Food Hydrocolloids, 7, 39–53; Fry, 1988, The growing Plant Cell Wall: Chemical and Metabolic Analysis).

Sugar beet debranched arabinan and potato galactan from Megazyme (Ireland, http://www.megazyme.com/Purchase/index.html) contain rhamnose and galacturonic acid indicating that these substrates and their AZCL derivatives contain some rhamnogalacturonan.

The biological degradation of pectic substances is a complex process involving several enzymes produced by a wide variety of saprophytic, plant pathogenic fungi and bacteria (Pilnik and Rombouts, 1979). For example, the hydrolysis of smooth, homogalacturonan regions of pectin by polygalacturonases is dependent upon demethylation of the homogalacturonan backbone by pectin methylesterase (Christgau et al., 1996; Pilnik and Rombouts, 1979). Several microbial polygalacturonases, pectate lyases, pectin methylesterases and pectin lyases active within the smooth regions of pectin have been described in literature.

A number of enzymes capable of hydrolyzing arabinan, galactan or arabinogalactan side chains in the hairy regions have been characterized. By contrast, only few enzymes capable of degrading the rhamnogalacturonan backbone have been reported. A rhamnogalacturonan hydrolase belonging to family 28 of glycosyl hydrolases and a rhamnogalacturonan lyase belonging to lyase family 4, both from Aspergillus aculeatus, have been cloned and characterized (Kofod et al. (1994) Journal of Biological Chemistry Vol. 269 (46) pp. 29182–29189; Kauppinen et al. (1995) Journal of Biological Chemistry Vol. 270 (45) pp. 27172–27178; Azadi et al. (1995) Glycobiology Vol. 5 (8) pp. 783–789; Mutter et al. (1996) Plant Physiology Vol. 110 (1) pp. 73–77; Mutter et al. (1998) Plant Physiology Vol. 117 (1) pp. 141–152; Mutter et al. (1998) Carbohydrate Research Vol. 311 (3) pp. 155–164). The sequence families can be found on http://afmb.cnrs-mrs.fr/~pedro/CAZY/db.html.

Degradation of rhamnogalacturonan by the Aspergillus rhamnogalacturonan hydrolase and lyase is enhanced by removal of acetyl groups from the backbone (Kofod et al., 1994; Schols et al., 1990). A rhamnogalacturonan acetylesterase (RGAE) cloned and characterized from Aspergillus aculeatus specifically removes acetyl groups from hairy regions and acts in synergy with the rhamnogalacturonases in degradation of apple pectin rhamnogalacturonan (Kauppinen et al., 1995).

JP 10-033169 discloses a method for purification of rhamnogalacturonase from enzyme preparations containing numerous enzymes or liquid cultures of Aspergillus, Bacillus or Erwinia.

The object of the present invention is to provide a novel rhamnogalacturonan hydrolase enzyme which can degrade the backbone of hairy regions of pectin in an effective manner useful in a number of different industrial applications.

SUMMARY OF THE INVENTION

The inventors have now found a number of novel bacterial enzymes exhibiting rhamnogalacturonan hydrolase activity which are believed to be members of two hitherto unidentified families of glycosyl hydrolases according to the classification based on hydrophobic cluster analysis (Henrissat, B. et al.). The novel enzymes have no amino acid sequence homology to known rhamnogalacturonan hydrolases from family 28 or rhamnogalacturonan lyases from lyase family 4. More specifically, novel families of enzymes degrading rhamnogalacturonan by hydrolysis has been found. The enzymes are of bacterial origin, with few or no cystein bridges and with a potential of being expressed in high yields in Gram positive bacterial hosts. The rhamnogalacturonase enzymes of this invention show enzymatic activity at neutral and alkaline conditions and, accordingly, they are very useful in a number of industrial applications.

The novel enzymes exhibit catalytic activity on rhamnogalacturonan as well as on the Megazyme products AZCL potato galactan and AZCL debranched arabinan. This activity can be explained by the presence of rhamnogalacturonan in the two AZCL carbohydrate polymers.

The inventors have succeeded in identifying either partial or full length DNA sequences encoding the novel enzymes. The DNA sequences are listed in the appended sequence listing as SEQ ID NOS: 1, 3, 5, 7, 9, 11, 13, 15, 17 and 19, and the deduced amino acid sequences are listed in the sequence listing as SEQ ID NOS: 2, 4, 6, 8, 10, 12, 14, 16, 18 and 20, respectively.

In a first aspect, the present invention relates to an enzyme exhibiting rhamnogalacturonan hydrolase activity wherein the enzyme belongs to a glycosyl hydrolase family other than family 28. In a preferred embodiment, the enzyme of the invention is obtained from a microbial strain belonging to Bacteria, preferably to Firmicutes or Proteobacteria, more preferably to Actinobacteria, Myxobacteria or the Bacillus/Clostridium group.

In second and third aspects, the invention relates to an enzyme comprising at least one amino acid sequence segment selected from the group of amino acid sequence segments consisting of NIRAGAHTQF(M or L)VYD(F or L)DGDGKAE (SEQ ID NO:21); YGNRVDRFLAG (SEQ ID NOS: 22); YGNRVDRFLAGXAYLDG (SEQ ID NO:23); AGQGNH(N or S)LS(I or V)ADVDGDGKDEII (SEQ ID NO:24); and AGQGNH(N or S)L(S or A)(I or V)ADVDGDGKDEII (SEQ ID NO:25); and to an enzyme comprising at least one amino acid sequence segment selected from the group of amino acid sequence segments consisting of EVRDATIGLL (SEQ ID NO:26); NNYVVGNPI (SEQ ID NO:27); and DADRTNRA (SEQ ID NO:28).

In further aspects, the invention relates to a rhamnogalacturonan hydrolase enzyme which is i) a polypeptide produced by a strain selected from the group consisting of *Bacillus licheniformis, Bacillus halodurans, Bacillus subtilis, Bacillus agaradhaerens,* Bacillus sp. AA386, *Sorangium cellulosum, Streptomyces coelicolor* and *Caldicellulosiruptor* sp.; or ii) a polypeptide comprising an amino acid sequence as shown in positions 1–621 of SEQ ID NO:2 or in positions 1–620 of SEQ ID NO:4, or in positions 1–620 of SEQ ID NO:6 or in positions 1–471 of SEQ ID NO:8 or in positions 1–170 of SEQ ID NO:10 or in positions 1–112 of SEQ ID NO:12 or in positions 1–655 of SEQ ID NO:14 or in positions 1–631 of SEQ ID NO:16 or in positions 1–389 of SEQ ID NO:18 or in positions 1–169 of SEQ ID NO:20; or iii) an analogue of the polypeptide defined in i) or ii) which is at least 75% homologous with said polypeptide and can be derived from said polypeptide by substitution, deletion or insertion of one or several amino acids.

Within other aspects, the present invention provides an isolated polynucleotide molecule selected from the group consisting of (a) polynucleotide molecules encoding a rhamnogalacturonase and comprising a sequence of nucleotides iselected from the group consisting of the nucleotide sequences shown in SEQ ID NO: 1 from nucleotide 1 to nucleotide 1863, SEQ ID NO:3 from nucleotide 1 to nucleotide 1863, and SEQ ID NO:5 from nucleotide 1 to nucleotide 1863, in SEQ ID NO: 7 from nucleotide 1 to nucleotide 1413, in SEQ ID NO: 9 from nucleotide 1 to nucleotide 512, in SEQ ID NO: 11 from nucleotide 1 to nucleotide 336, in SEQ ID NO: 13 from nucleotide 1 to nucleotide 1965, in SEQ ID NO: 15 from nucleotide 1 to nucleotide 1896, in SEQ ID NO: 17 from nucleotide 1 to nucleotide 1168, in SEQ ID NO: 19 from nucleotide 1 to nucleotide 507; (b) species homologs of (a); (c) polynucleotide molecules that encode a polypeptide which can degrade the rhamnogalacturonan backbone of hairy regions of pectin and which is at least 75% identical to the amino acid sequence of SEQ ID NO: 2 from amino acid residue 1 to amino acid residue 621, SEQ ID NO: 4 from amino acid residue 1 to amino acid residue 620, or SEQ ID NO: 6 from amino acid residue 1 to amino acid residue 620, SEQ ID NO: 8 from amino acid residue 1 to amino acid residue 471, SEQ ID NO: 10 from amino acid residue 1 to amino acid residue 170, SEQ ID NO: 12 from amino acid residue 1 to amino acid residue 112, SEQ ID NO: 14 from amino acid residue 1 to amino acid residue 655, SEQ ID NO: 16 from amino acid residue 1 to amino acid residue 631, SEQ ID NO: 18 from amino acid residue 1 to amino acid residue 389, SEQ ID NO: 20 from amino acid residue 1 to amino acid residue 169; (d) molecules complementary to (a), (b) or (c); and (e) degenerate nucleotide sequences of (a), (b), (c) or (d).

The *E. coli* plasmids comprising the polynucleotide molecules (the DNA sequences corresponding to SEQ ID NOS: 1, 3, 9, 13, 17 respectively) encoding an enzyme of the present invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Apr. 24, 1998 under the deposition numbers DSM 12123 and DSM 12122, on Sep. 8, 1998 under the deposition number DSM 12405, on Apr. 24, 1998 under the deposition number DSM 12124, and on May 29, 1998 under the deposition number DSM 12202, respectively.

Within another aspect of the invention there is provided an expression vector comprising the following operably linked elements: a transcription promoter; a DNA segment selected from the group consisting of (a) polynucleotide molecules encoding a rhamnogalacturonan hydrolase and comprising a sequence of nucleotides as shown in SEQ ID NO: 1 from nucleotide 1 to nucleotide 1863, SEQ ID NO:3 from nucleotide 1 to nucleotide 1863, and SEQ ID NO:5 from nucleotide 1 to nucleotide 1863, in SEQ ID NO: 7 from nucleotide 1 to nucleotide 1413, in SEQ ID NO: 9 from nucleotide 1 to nucleotide 512, in SEQ ID NO: 11 from nucleotide 1 to nucleotide 336, in SEQ ID NO: 13 from nucleotide 1 to nucleotide 1965, in SEQ ID NO: 15 from nucleotide 1 to nucleotide 1896, in SEQ ID NO: 17 from nucleotide 1 to nucleotide 1168, in SEQ ID NO: 19 from nucleotide 1 to nucleotide 507; (b) species homologs of (a); (c) polynucleotide molecules that encode a polypeptide which can degrade rhamnogalacturonan backbone of hairy regions of pectin and which is at least 75% identical to the amino acid sequence of SEQ ID NO: 2 from amino acid residue 1 to amino acid residue 621, SEQ ID NO: 4 from amino acid residue 1 to amino acid residue 620, or SEQ ID NO: 6 from amino acid residue 1 to amino acid residue 620, SEQ ID NO: 8 from amino acid residue 1 to amino acid residue 471, SEQ ID NO: 10 from amino acid residue 1 to amino acid residue 170, SEQ ID NO: 12 from amino acid residue 1 to amino acid residue 112, SEQ ID NO: 14 from amino acid residue 1 to amino acid residue 655, SEQ ID NO: 16 from amino acid residue 1 to amino acid residue 631, SEQ ID NO: 18 from amino acid residue 1 to amino acid residue 389, SEQ ID NO: 20 from amino acid residue 1 to amino acid residue 169; and (d) degenerate nucleotide sequences of (a), (b), or (c); and a transcription terminator.

Within yet another aspect of the present invention there is provided a cultured cell into which has been introduced an expression vector as disclosed above, wherein said cell expresses the polypeptide encoded by the DNA segment.

Within another aspect of the present invention there is provided a composition comprising a purified polypeptide according to the invention, i.e. an enzyme, in combination with other polypeptides exhibiting enzymatic activity.

At present it is contemplated that the novel enzyme of the present invention is useful for the treatment of cellulosic material, especially cellulose-containing fiber, yarn, woven or non-woven fabric. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising a rhamnoglacturonan hydrolase enzyme or an enzyme capable of degrading rhamnogalacturonan backbone of hairy regions of pectin; and to use of the enzyme of the invention for the treatment of cellulose-containing fibers, yarn, woven or non-woven fabric.

It is also contemplated that the enzyme of the invention is effective for use in an enzymatic scouring process in the preparation of cellulosic material e.g. for proper response in subsequent dyeing operations. Further, it is contemplated that detergent compositions comprising the novel enzyme are capable of removing or bleaching certain soils or stains present on laundry, e.g. soils and spots resulting from food, plants, and the like containing pectic substances. It is also contemplated that treatment with detergent compositions comprising the novel enzyme can prevent binding of certain soils to the cellulosic material.

DRAWINGS

In the attached drawings.

DEFINITIONS

Figure 1:
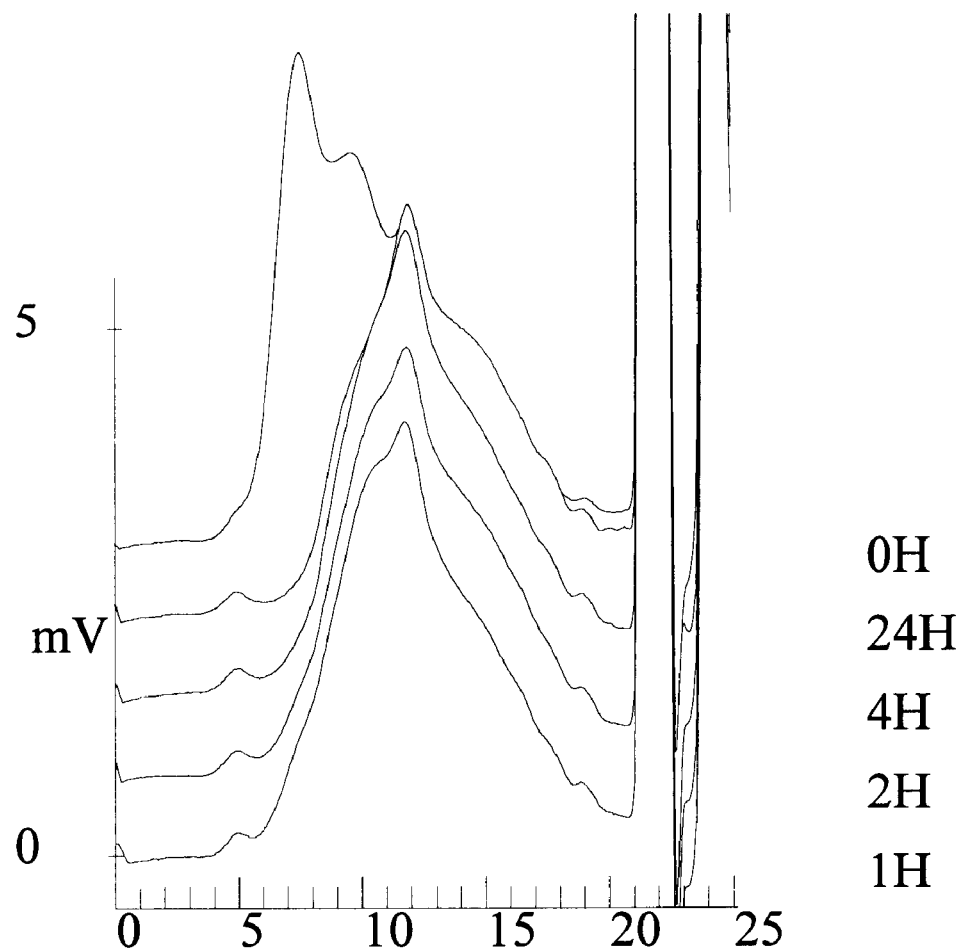
FIG. 1 shows high performance size exclusion chromatography (HPSEC) of hairy regions from apples (MHR) degraded by the rhamnogalacturonan hydrolase from Bacillus sp. AA 386 (BXR1).

Prior to discussing this invention in further detail, the following terms will first be defined.

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with specific microbial source, means that the polynucleotide and/or polypeptide produced by the specific source, or by a cell in which a gene from the source have been inserted.

The term "operably linked", when referring to DNA segments, denotes that the segments are arranged so that they function in concert for their intended purposes, e.g. transcription initiates in the promoter and proceeds through the coding segment to the terminator The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "pectin" denotes pectate, polygalacturonic acid, and pectin which may be esterified to a higher or lower degree.

The term "hairy regions of pectins" denotes the highly branched rhamnogalacturonan regions of pectins consisting of repeating alpha-1,2-L-Rha-alpha-1,4-D-GalUA disaccharide units with side chains mainly consisting of neutral oligosaccharides such as arabinan, galactan and/or arabinogalactan and wherein the GalUA residues may be acetyl esterified or methyl esterified.

The term "pectic substance" denotes pectin and hairy regions of pectins.

The term "rhamnogalacturonase" denotes an enzyme capable of degrading the rhamnogalacturonan backbone of hairy regions of pectins.

The term "rhamnogalacturonan hydrolase" denotes an enzyme belonging to the enzyme class of glycosyl hydrolases (EC 3.2.X.X according to the IUB Enzyme Nomenclature). The rhamnogalaturonan hydrolase enzyme exhibits activity towards rhamnogalacturonan backbone of hairy regions of pectin.

The term "glycosyl hydrolase family" has been descibed in:

1. Henrissat, B. "A classification of glycosyl hydrolases based of amino-acid sequence similarities." Biochem. J. 280: 309–316 (1991).
2. Henrissat, B., Bairoch, A. "New families in the classification of glycosyl hydrolases based on amino-acid sequence similarities. Biochem. J. 293: 781–788 (1993).
3. Henrissat, B., Bairoch, A. "Updating the sequence-based classification of glycosyl hydrolases." Biochem. J. 316: 695–696 (1996).
4. Davies, G., Henrissat, B. "Structures and mechanisms of glycosyl hydrolases." Structure 3: 853–859 (1995).

Public available data from:
http://afmb.cnrs-mrs.fr/~pedro/CAZY/db.html

DETAILED DESCRIPTION OF THE INVENTION

How to Use a Sequence of the Invention to Get Other Related Sequences

The disclosed sequence information herein relating to a polynucleotide sequence encoding an enzyme of the invention can be used as a tool to identify other homologous enzymes exhibiting the same enzymatic activity. For instance, polymerase chain reaction (PCR) can be used to amplify sequences encoding other homologous enzymes from a variety of microbial sources, in particular of different Bacillus species.

Assay For Activity Test

A polypeptide of the invention capable of degrading the rhamnogalacturonan backbone of hairy regions of pectins may be tested for this activity according to test procedures known in the art, such as by applying a solution to be tested to 4 mm diameter holes punched out in agar plates containing 0.5% AZCL potato galactan (Megazyme, Ireland) and 0.5% AZCL debranched arabinan (Megazyme), respectively. The enzyme of the invention shows activity on both substrates.

Polynucleotides

Within preferred embodiments of the invention an isolated polynucleotide of the invention will hybridize to similar sized regions of SEQ ID Nos: 1, 3, 5, 7, 9, 11, 13, 15, 17 and 19, respectively, or a sequence complementary thereto, under at least medium stringency conditions.

In particular polynucleotides of the invention will hybridize to a double-stranded DNA probe comprising a selected sequence from the group shown in: SEQ ID NO: 1 from nucleotide 1 to nucleotide 1863, SEQ ID NO:3 from nucleotide 1 to nucleotide 1863, SEQ ID NO:5 from nucleotide 1 to nucleotide 1863, SEQ ID NO: 7 from nucleotide 1 to nucleotide 1413, SEQ ID NO: 9 from nucleotide 1 to nucleotide 512, SEQ ID NO: 11 from nucleotide 1 to nucleotide 336, SEQ ID NO: 13 from nucleotide 1 to nucleotide 1965, SEQ ID NO: 15 from nucleotide 1 to nucleotide 1896, SEQ ID NO: 17 from nucleotide 1 to nucleotide 1168, and SEQ ID NO: 19 from nucleotide 1 to nucleotide 507, under at least medium stringency conditions, but preferably at high stringency conditions as described in detail below.

Suitable experimental conditions for determining hybridization at medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of-denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity>$1\times10^9$ cpm/µg) probe for 12 hours at ca. 45° C. The filter is then washed twice for 30 minutes in 2×SSC, 0.5% SDS at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides of the invention capable of degrading rhamnogalacturonan backbones of hairy regions of pectins, ie rhamnogalacturonases, are then identified and isolated by, for example, hybridization or PCR.

The present invention further provides counterpart polypeptides and polynucleotides from different bacterial strains (orthologs or paralogs). Of particular interest are polypeptides from gram-positive strains, including species of Bacillus such as *Bacillus subtilis, Bacillus lentus, Bacillus brevis, Bacillus stearothermophilus, Bacillus agaradhaerens, Bacillus alkalophilus, Bacillus amyloliquefaciens, Bacillus coagulans, Bacillus circulans, Bacillus halodurans, Bacillus lautus, Bacillus thuringiensis, Bacillus clausii* or *Bacillus licheniformis;* and polypeptides from Thermoanaerobacter group, including species of Caldicellulosiruptor; and polypeptides from Actinobacteria, preferably from Actinomycetales, more preferably from Streptomycetaceae, including species of Streptomyces, in particular *Streptomyces coelicolor;* and polypeptides from Proteobacteria, preferably from Myxobacteria, including species of Sorangiaceae, especially Sorangium, for example *Sorangium cellulosum.*

Based on their findings of novel enzymes encoded by the DNA sequences listed as SEQ ID NOS: 1 and 3 respectively, the inventors have searched publicly available databases for genes highly homologous therewith and have succeeded in identifying the DNA sequence corresponding to the gene known as the YesW gene from *Bacillus subtilis,* the "YesW" name implying to the skilled person that this DNA sequence has an unknown open reading frame and does not have any significant homology to any known gene, i.e. that the function of the gene/the polypeptide possibly encoded by the gene is unknown. The YesW gene is listed as SEQ ID NO:5 and the derived amino acid sequence is listed as SEQ ID NO:6. The present inventors have succeeded in cloning and expressing the YesW gene in *E.coli* as well as in *B. subtilis,* cf. the examples below, and have demonstrated the enzymatic activity of the expressed polypeptide. In a similar manner, YesW type genes have been identified from *Streptomyces coelicolor* and *Sorangium cellulosum.*

Species homologues of a polypeptide of the invention can be cloned using information and compositions provided by the present invention in combination with conventional cloning techniques. For example, DNA can be cloned using chromosomal DNA obtained from a cell type that expresses the protein. Suitable sources of DNA can be identified by probing Southern or Northern blots with probes designed from the sequences disclosed herein. A library is then prepared from chromosomal DNA of a positive cell line. A DNA encoding a polypeptide of the invention can then be isolated by a variety of methods, such as by probing with a complete or partial DNA sequence or gene, or with one or more sets of degenerate probes based on the disclosed sequences.

A DNA can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (monoclonal or polyclonal) raised against the enzyme of the invention (e.g. BXR1, BSR5, BLR3, BXA15), expressed and possibly purified as described in the examples below or by a rhamnogalacturonase activity test or another test relating to a polypeptide capable of degrading rhamnogalacturonan backbone of hairy regions of pectins.

Polypeptides

The sequence of amino acids no. 1–621 of SEQ ID No 2 is a full length enzyme sequence. The sequence of amino acids no. 1–620 of SEQ ID No 4 is a full length enzyme sequence. The sequence of amino acids no. 1–620 of SEQ ID No 6 is a full length enzyme sequence. The sequence of amino acids no. 1–655 of SEQ ID No 14 is a full length enzyme sequence. The sequence of amino acids no. 1–631 of SEQ ID No 16 is believed to be a full length enzyme sequence. The sequence of amino acids no. 1–389 of SEQ ID No 18 is a full length enzyme sequence. The sequence of amino acids no. 1–471 of SEQ ID No 8 is part of a full length enzyme sequence. The sequence of amino acids no. 1–170 of SEQ ID No 10 is part of a full length enzyme sequence. The sequence of amino acids no. 1–112 of SEQ ID No 12 is part of a full length enzyme sequence. The sequence of amino acids no. 1–169 of SEQ ID No 20 is part of a full length enzyme sequence (corrected for reading frame skips).

The present invention also provides polypeptides that are substantially homologous to the polypeptides of SEQ ID NO: 2, 4, 6, 8, 10, 12, 14, 16, 18 or 20 and their species homologs (paralogs or orthologs). The term "substantially homologous" is used herein to denote polypeptides having 45%, preferably at least 50%, more preferably at least 55%, more preferably at least 60%, more preferably at least 65%, more preferably at least 70%, more preferably at least 75%, preferably at least 80%, more preferably at least 85%, and even more preferably at least 90%, sequence identity to the sequence shown in SEQ ID NO: 2, 4, 6, 8, 10, 12, 14, 16, 18 or 20 or their orthologs or paralogs. Such polypeptides will more preferably be at least 95% identical, and most preferably 98% or more identical to the sequence shown in SEQ ID NO: 2, 4, 6, 8, 10, 12, 14, 16, 18 or or their orthologs or paralogs. Percent sequence identity is determined by conventional methods, by means of computer programs known in the art such as GAP provided in the GCG program package (Wisconsin Package Version 9.1, Genetics Computer Group (GCG), Madison, Wisc.) which is disclosed in Needleman, S.B. and Wunsch, C.D., (1970), Journal of Molecular Biology, 48, 443–453, this citation is hereby incorporated by reference in its entirety). GAP is used with the following settings for polypeptide sequence comparison: The standard PAM table blosum62 with a gap creation penalty of 12 and a gap extension penalty of 4 was employed throughout.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to the polypeptide of the invention.

TABLE 1

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e activity towards galactan and arabinan) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223, 409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to the peptides disclosed herein and retain the enzymatic activity of the wild-type protein.

Identification of Other Novel Carbohydrases in These Two Subfamilies

Two basic approaches can be used.
1) Screening with assay plates (AZCL debranched arabinan and AZCL potato galactan for example) other libraries of bacterial species.

2) This class of enzyme has a high level of sequence identity at the amino acid level as shown in the following alignment.

Multiple Sequence Alignment of Subfamily A Performed By Clustal Analysis (DNAstar, Megalign Ver. 3.1.7)
BXR1: Bacillus sp. AA386 (SEQ ID NO: 2)
BLR3: *B. licheniformis* (SEQ ID NO:4)
BSR5: *B. subtilis* (SEQ ID NO:6)
BXR9: *B. halodurans* C4538 (SEQ ID NO:14)
SCR6: *Sorangium cellulosum* (SEQ ID NO:8)
STR12: *Streptomyces coelicolor* (SEQ ID NO:16)
XXR7: Caldicellulosiruptor sp. (SEQ ID NO: 10)
XXR13: Caldicellulosiruptor sp. (SEQ ID NO:12)

```
               1                                                            60
Blr3.pro   MR....RSCLMIRRRKRMFTAVTLLVLLVMGTSVCPV.....KAEGAAR.QMEALNRGLV
Bsr5.pro   MR....RSCLMIRRRKRMFTAVTLLVLLVMGTSVCPV.....KAEGAAR.QMEALNRGLV
bxr1.PRO   M.........FSKRLHHFWRV.MLGLVVVVSTIGSVFLPVSTASAAPR.QAENISRGLV
Bxr9.pro   M...........................................LR.QKEQLDRGLV
SCR6.pro   ............................................................
Str12.pro  VRHPHTRPHAPHPHRRRPRALAAALAAAGLLGAGLTTLAPDTAEAATAR.QVEALDRGVV
Xxr13.pro  ............................................................
Xxr7.PRO   MRK.........KKIYRSWLGIVVIILWVIYCVFNPYNLAIKNVKGAVSSQVEKLKRGLI 61                                                          120
Blr3.pro   AVKTDGGIFVSWRFLGTENASVLFNVYRDGQKLNAAPV.KTTNYVDKNGSAGSTYTVRAV
Bsr5.pro   AVKTDGGIFVSWRFLGTENASVLFNVYRDGQKLNAAPV.KTTNYVDKNGSAGSTYTVRAV
bxr1.PRO   AVKVSSGVFISWRLLGTEQLSTSFNVYRNGTKVNAAPITNSTNLLDTAGTTSSTYTVRAV
Bxr9.pro   AVKAADGVFLSWRLLGTEHPLTVFHVYRDGEKITKAGLQEGTNFVDADGMTDSVYQIKAV
SCR6.pro   ............................................................
Str12.pro  SVHTGDGNLVSWRWLGTDPDNVAFNVYRAGTKVNSSPVTGSTTYFHSGAPSHADYTVRAV
Xxr13.pro  ............................................................
Xxr7.PRO   AIKVNNGVYLTWRMFGSDPADIGFNIYRNGQKINQIPIQVSThYLDTGGNTTSKYFIRPV 121                                                         180
Blr3.pro   VNGTEQPASEKASVWAQPYHSVPLDKPAGGTTPKGESYTYSANDASVGDVDGDGQYELIL
Bsr5.pro   VNGTEQPASEKASVWAQPYHSVPLDKPAGGTTPKGESYTYSANDASVGDVDGDGQYELIL
bxr1.PRO   VGGVEQPASPAVRVWANNYLDVPIQAPPGGRTPDGVNYTYSANDASIGDLDGDGEYEIVL
Bxr9.pro   .AGKDEDMSNPVSVWDDEYLAIPLDKPEGGVTPDGVSYEYTANDASVGDLDGDGQYEIIL
SCR6.pro   ...............................................DLDGDGRYEIIV
Str12.pro  VNGTEQGDSVHAIQFRAdYKDVPISPPSGGTTPDGVSYTYEANDASVGDLDGDGALDLVL
Xxr13.pro  ............................................................
Xxr7.PRO   INGHEIENSEEVSVLPTNYIEIKLNRPP..TSPLGA..IYSPNDASVGDLDGDGEYEIVL 181                                                         240
Blr3.pro   KWDPSNSKDNSQDGYTGDVLIDAYKLDGTKLWRINLGKNIRAGAHYTQFMVYDLDGDGKA
Bsr5.pro   KWDPSNSKDNSQDGYTGDVLIDAYKLDGTKLWRINLGKNIRAGAHYTQFMVYDLDGDGKA
bxr1.PRO   KWDPTNSKDNSQGGYTGNVYLDAYKLNGTRLWRIDLGRNIRAGAHYTQFLVYDFDGDGKA
Bxr9.pro   KWDPTNSKDNSRSGYTGNVYLDAYKLDGTKLWRLDLGRNIRAGAHYSQFLVYDFDGNGRS
SCR6.pro   KWDPSNLKDNSQAGRTGKTYLDAYSLEGERLWRIDLGVNIRAGAHYSPFLVYDLDGDGKA
Str12.pro  KWQPTNAKDNSQSGYTGNTVVDGIKLDGTRLWRVDLGRNIRSGAHYTQFQVYDYDGDGRA
Xxr13.pro  ............................................................
Xxr7.PRO   KWD.........................................................

241                                                         300
Blr3.pro   EVAMKTADGTKDGTGKVIGNANA.......DYRNEQGRVLSGPEYLTVFQGSTGKELVTA
Bsr5.pro   EVAMKTADGTKDGTGKVIGNANA.......DYRNEQGRVLSGPEYLTVFQGSTGKELVTA
bxr1.PRO   EIVCKTADGTVDGTGITIGNANA.......DHRNANGYVLSGPEFLTVFSGQTGKALTTI
Bxr9.pro   EVVLKTADGTIDGVGNVIGDQDA.......DYRNSSGYILDGPEYLTIFSGETGEALDTI
SCR6.pro   EVAVKTAPGTRDGTGEPLSKGPAANDDDSRDYRNNDGYILTGPEYLTVFSGETGAELATT
Str12.pro  EVAMKTADGTKDGTGAVIGNSSA.......DHRNSSGYVLSGPEYLTMFNGRTGTAMGTV
Xxr13.pro  ............................................................
Xxr7.PRO   ............................................................

301                                                         360
Blr3.pro   NFEPARGNVSDWGDS..YGNRVDRFLAGIAYLDGQ.RPSLIMTRGYYAKTMLVAYNFRDG
Bsr5.pro   NFEPARGNVSDWGDS..YGNRVDRFLAGIAYLDGQ.RPSLIMTRGYYAKTMLVAYNFRDG
bxr1.PRO   DYVPPRGNVSSWGDN..YGNRVDRFLAGVAYLDGV.HPSIIMARGYYTRTVVVAYDWNGR
Bxr9.pro   DYVPPRGNVSDWGDN..YGNRVDRFLAGVAYLDGE.RPSFVAARGYYTRTVLAAYQWDDG
SCR6.pro   DFVVGRGDPCSWGNNECYGNRVDRFVGTVAFLDDTGRPSVVFGRGYYARTTLSAWNYRDG
Str12.pro  DYVPARGSVSSWGDS..YGNRVDRFLAGTAYLDGS.RPSVIMARGYYTRTVIAAWDWRDG
Xxr13.pro  ............................................................
Xxr7.PRO   ............................................................

361                                                         420
Blr3.pro   KLSKLWTLDSSKSGNEA..FAGQGNHNLSIADVDGDGKDEIIFGSMAVDHDGKGMYSTGL
Bsr5.pro   KLSKLWTLDSSKSGNEA..FAGQGNHNLSIADVDGDGKDEIIFGSMAVDHDGKGMYSTGL
bxr1.PRO   ALTRRWTFDSNSSTNPG..TAGQGNHSLSVADVDGDGKDEIIYGALTINDNGATLYNTRL
Bxr9.pro   KIKEQWVFDSNDPGNER..YAGQGNHSLAIADVDGDGKDEIIYGAVVVDHDGTGLYSTGW
SCR6.pro   ALTNLWTFDSSSSRDNG.AYAGMGTHSISVANVDDDPQQEIINGGATFDNDGKGLCAVDY
Str12.pro  RFTRRWTFDTNSSTNSGKGYDGQGNHQLSVADVDGDGRDEIVYGAMAVDDNGYALWTTRN
Xxr13.pro  ............................................................
Xxr7.PRO   ............................................................
```

-continued

```
           421                                                        480
Blr3.pro   .GHGDALHTGDLDPGRPGLEVFQVHEDKNAKYGLSFRDAATGKILW...GVYAGKDVGRG
Bsr5.pro   .GHGDALHTGDLDPGRPGLEVFQVHEDKNAKYGLSFRDAATGKILW...GVYAGKDVGRG
bxr1.PRO   .GHGDALHVGDFNPNRPGLEVFKVMEDANAPYGAAVWDAATGQILW...GVRTGRDTGRG
Bxr9.pro   .GHGDANHVSNLNPNRKGLEIFQPHEDSRSPVGYGIRDAETGELLW...GEFTGTDVGRA
SCR6.pro   YGHGDALHVTDHILSRPGLEVFQPYEGGDSP.AYAMRDARTCEVLWRGPGNGGEEGPGRG
Str12.pro. GHGDAMHVGDLDPSRAGLEEFKVDEDGSKPSSY.LADARTGQILW...STGASGDNGRG
Xxr13.pro  ............................................................
Xxr7.PRO   ............................................................

481                                                        540
Blr3.pro   MAADIDPRYPGQEVWANG......S..LYSAKGVKIGSGVPSSTNFGIWWDGDLLREQLD
Bsr5.pro   MAADIDPRYPGQEVWANG.........LYSAKGVKIGSGVPSSTNFGIWWDGDLLREQLD
bxr1.PRO   MAADIDPNHPGVEVWASG......GVGLYSITGTKISNNTPS.INFGIWWDGDLSRELLD
Rxr9.pro   LAADIDPRFDGAELWASAQWDGREGSGLFSVEGESITTKTPQSVNFAIWWTGDLLRELLD
SCR6.pro   VAADVDPRNPGSEAWVNS......SQLLSGADGDAIGNR.PASSNFLIWWDADLSRELLD
Str12.pro  VSGDIWSGSAGAESWSSA......ESGIRNPKGTVVGSRKPSSANFLSWWDGDTVRELLD
Xxr13.pro  .....................................................DLTRELLD
Xxr7.PRO   ............................................................

541                                                        600
Blr3.pro   SN...........RIDKWDYQNGVSKNMLTASGAAANNGTKATPTLQADLLGDWREEVVW
Bsr5.pro   SN...........RIDKWDYQNGVSKNMLTASGAAANNGTKATPTLQADLLGDWREEVVW
bxr1.PRO   DI...........RIDKWNYNNNTMYNLLTGSGVASNNGTKATPTLQADLIGDWREEVIW
Bxr9.pro   HSFDPSKDPHGVGKIEKWDWEKEELVEIFVPEGTRSNNWTKGNPSLQADLFGDWREEVIW
SCR6.pro   G..NSIRQADGEG.............SNFAAEGCTANNGSKSNPTLSADILGDWREEVIF
Str12.pro  GT...........HVDK..YGTSGDTRLLTGSGVASNNGTKATPVLAGDILGDWREEVVW
Xxr13.pro  KT...........NIYKWDYNTNSSKTIFTASGCSANNGTKATPCLSADILGDWREEVIF
Xxr7.PRO   ............................................................

601                                                        660
Blr3.pro   RTEDSSALRIYTTTIPTEHRLYTLMHDPVYRLGIAWQNIAYNQPPHTSFFLGDGMAEQPK
Bsr5.pro   RTEDSSALRIYTTTIPTEHRLYTLMHDPVYRLGIAWQNIAYNQPPHTSFFLGDGMAEQPK
bxr1.PRO   RKSDNTALRIYTTTDLTNHKIYTLMHDPVYRLSIAWQNVAYNQPPHTGFFLGSGMGPVTK
Bxr9.pro   PSADSNELRIYTTTEETEHRIPTLMHDSVYRLSVAWQNVGYNQPPHTSYFLGHGMKEAPL
SCR6.pro   RCG..SSIRIFTTNRVATSRIHTLMHDPQYRVAISWQNGAYNQPPHPSFHIGEGMAPVPK
Str12.pro  RTSNNTALRIYSTPYDTDTRITTLLHDTQYRTALAWQNTAYNQPPHPSFFLGSGMPTAPR
Xxr13.pro  RTSDNSAIRIYMTTMQTSYKIPTLMHNRQYRVSIAWQNVAYNQPPHTNFYFGEGM.....
Xxr7.PRO   ............................................................

661                                                        719
Blr3.pro   PNMYT....P..................................................
Bsr5.pro   PNMYT....P..................................................
bxr11.PRO  PDIYV...VP..................................................
Bxr9.pro   PKVHAGQVVPVELKANQQGKKKLSVQVRFDSPTAGESLVSSSVRLFVNGETIQAEKVHR
SCR6.pro   PDIHV.......................................................R
Str12.pro  PSVHT....P..................................................
Xxr13.pro  ............................................................
Xxr7.PRO   ............................................................
```

Multiple Sequence Alignment of Subfamily B Performed By Clustal Analysis (DNAstar. Megalign Ver. 3.1.7)
BXA15: *B. halodurans* KJ59 (SEQ ID NO: 18)
BAR16: *B. agaradhaerens* (SEQ ID NO: 20)

```
            1                                                          60
Bxa15.pro   MNKLGMWFSGLILVVGLLVGGNEAKANEVVNARDFGATPGVATSQTN.ALHAAMRHFYDR
Bar16.pro   RD...FWDRG.............................PGVSGKAKRMPLHAAMRYFYDR 61                                                         120
Bxa15.pro   GVQG.TVYIPAGTYSIDEALRFHSGVNIVGDGMGRTILKKTGNSNNYVVGNPIMRGSN.N
Bar16 pro   GVRGKTVYLPAGTYSVDSALRFHQGVNLVGDGVGRTIIKKVGSQNNYVVGNPIFRGGTTN 121                                                        180
Bxa15.pro   LNVTVSNLTIDADRThRAQRGLGQVGGM..NLDADVSNLTLERVEVRDATIGLLLRRLKN
Bar16.pro   LNVTVSHITFDADRTNRASQGLGQVGGTGEQFTALVSNLTLEHIEVRDATIGLLVRRXR.

181                                                        240
Bxa15.pro   SVVRDSVIDNTTGHGIAFGHENHPIGDVRNNLITGNRITNSTGGSGINLSRATYTTVTHN
Bar16.pro   SVISDSLIDRTSWHGIATGSE........................................

241                                                        300
Bxa15.pro   QVINDRQQDDSYGGIRIPNGGEHNTVEYNTIRNYPRGIFVLSGARHNQINHNTVIDSRIH
Bar16.pro   ............................................................
```

```
                    -continued
        301                                            360
Bxa15.proGVLIQADHNTLRENRIQQLNSSLNPESVVRIAPGSNNSILNNNIQAHSNFRNIGIRVTGD
Bar16.pro..........................................................

361                    394
Bxa15.proSNNNVIRNNRIGTQGTLVSIEGGRVNVNEGNVRQ
Bar16.pro.................................
```

Therefore three approaches can be used to take advantage of this:

a) Design degenerate PCR primer sets deduced from consensus amino acid sequences from the disclosed rhamnogalacturonases from subfamily A or subfamily B. Perform PCR on DNA from bacterial species, eg Bacillus, and determine which species give a specific band of approximately the correct size. Clone and sequence or sequence directly this PCR fragment. This sequence information can be used to design specific primers facing outwards and one of several hybrid PCR approaches may be used to obtain the rest of the sequence (Sakamoto et al., 1997)). These methods are known by those skilled in the art.

Accordingly, it is contemplated that the novel enzyme of the present invention can be identified by amino acid consensus domains common to all amino acid sequences in this class which are provided herein (as seen in above alignment). Preferred consensus domains can be selected from the following groups:

Subfamily A
SANDAS (SEQ ID NO: 29)
LKWDP(S or T)NSKDN (SEQ ID NO: 30)
DAYKL(D or N)GT (SEQ ID NO: 31)
NIRAGAHTQF(M or L)VYD(F or L)DGDGKAE (SEQ ID NO: 32)
KTADGT (SEQ ID NO: 33)
LSGPE(Y or F)LTV (SEQ ID NO: 34)
YGNRVDRFLAG (SEQ ID NO: 35)
AYGNRVDRFIAGXAYLDG (SEQ ID NO: 36)
AGQGNH(N or S)LS(I or V)ADVDGDGKDEII (SEQ ID NO: 37)
AGQGNH(N or S)L(S or A) (I or V)ADVDGDGKDEII (SEQ ID NO: 38)
LRIYTTT (SEQ ID NO: 39)
YTLMHD (SEQ ID NO: 40)
(Y or P)TLMHD(P or S)VYRL(S or G)IAWQN (SEQ ID NO: 41)
VYRL(S or G)IAWQN (SEQ ID NO: 42)
Subfamily B
EVRDATIGLL (SEQ ID NO: 43)
NNYVWGNPI (SEQ ID NO: 44)
DADRTNRA (SEQ ID NO: 45)

b) Cloned PCR fragment can also be labelled and used to probe a genomic DNA library as either colony or phage. In this way a full length clone can be obtained. Screening plasmid or phage libraries is well known by those skilled in the art. Generally, screening in these cases is done under high stringency to avoid false positives. Screening is usually performed with hybridization conditions as follows: 6×SSC and 68° C. for hybridization of the probe to the filters. Then final washes at 0.2×SSC and 68° C.

c) Heterologous probing of a genomic DNA library may also be performed to clone genes homologous to rhamnogalactuonases of the invention. DNA sequence homology appears to be quite high in this family so this method is a generally useful one. Hybridization is then made under low stringency the lowest range normally used being 6×SCC and 42° C. for the hybridization, and washing with 2×SSC and typically 42° C. Additional washes may be necessary at higher stringency after monitoring with X-ray film.

Protein Production

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as *Bacillus subtilis, Bacillus lentus, Bacillus brevis, Bacillus stearothermophilus, Bacillus agaradhaerens, Bacillus alkalophilus, Bacillus amyloliquefaciens, Bacillus coagulans, Bacillus circulans, Bacillus halodurans, Bacillus lautus, Bacillus thuringiensis, Bacillus clausii,* or in particular *Bacillus licheniformis.*

Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989; Ausubel et al. (eds.), *Current Protocols in Molecular Biology,* John Wiley and Sons, Inc., NY, 1987; and (*Bacillus subtilis* and Other Gram-Positive Bacteria, Sonensheim et al., 1993, American Society for Microbiology, Washington D.C.), which are incorporated herein by reference.

In general, a DNA sequence encoding an enzyme of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo. Numerous suitable secretory signal sequences are known in the art and reference is made to (*Bacillus subtilis* and Other Gram-Positive Bacteria, Sonensheim et al., 1993, American Society for Microbiology, Washington D.C.; and Cutting, S. M.(eds.) "Molecular Biological Methods for Bacillus". John Wiley and Sons, 1990) for further description of suitable secretory signal sequences especially for secretion in a Bacillus host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Protein Isolation

When the expressed recombinant polypeptide is secreted the polypeptide may be purified from the growth media. Preferably the expression host cells are removed from the media before purification of the polypeptide (e.g. by centrifugation).

When the expressed recombinant polypeptide is not secreted from the host cell, the host cell are preferably disrupted and the polypeptide released into an aqueous "extract" which is the first stage of such purification techniques. Preferably the expression host cells are removed from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) is secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries.

These and other solid media are well known and widely used in the art, and are available from commercial suppliers.

Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

In the present context, the term "enzyme preparation" is intended to mean either be a conventional enzymatic fermentation product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant enzyme of the present invention, but which microorganism simultaneously produces other enzymes, e.g. galactanases, arabinases, proteases, or cellulases, being naturally occurring fermentation products of the microorganism, i.e. the enzyme complex conventionally produced by the corresponding naturally occurring microorganism.

The enzyme preparation of the invention may further comprise one or more enzymes selected from the group consisting of proteases, cellulases (endo-β-1,4-glucanases), β-glucanases (endo-β-1,3(4)-glucanases), lipases, cutinases, peroxidases, laccases, amylases, glucoamylases, pectinases, reductases, oxidases, phenoloxidases, ligninases, pullulanases, arabinanases, galactanases, hemicellulases, mannanases, xyloglucanases, xylanases, pectin acetyl esterases, rhamnogalacturonan acetyl esterases, polygalacturonases, rhamnogalacturonases, pectin lyases, pectate lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are mono-component enzyme(s) which is/are mixed with the other enzyme(s) to form an enzyme preparation with the desired enzyme blend.

In another aspect, the present invention also relates to a method of producing the enzyme preparation of the invention, the method comprising culturing a microorganism capable of producing the enzyme of the invention under conditions permitting the production of the enzyme, and recovering the enzyme from the culture. Culturing may be carried out using conventional fermentation techniques, e.g. culturing in shake flasks or fermenters with agitation to ensure sufficient aeration on a growth medium inducing production of the enzyme of the present invention. The growth medium may contain a conventional N-source such as peptone, yeast extract or casamino acids, a reduced amount of a conventional C-source such as dextrose or sucrose, and an inducer such as hairy regions from pectin or composite plant substrates such as apple pulp. The recovery may be carried out using conventional techniques, e.g. separation of bio-mass and supernatant by centrifugation or filtration, recovery of the supernatant or disruption of cells if the enzyme of interest is intracellular, perhaps followed by further purification as described in EP 0 406 314 or by crystallization as described in WO 97/15660.

Examples of useful bacteria producing the enzyme or the enzyme preparation of the invention are Gram positive bacteria, preferably from the Bacillus/Lactobacillus subdivision, preferably a strain from the genus Bacillus, especially a strain of *Bacillus licheniformis, Bacillus halodurans, Bacillus agaradhaerens,* or *Bacillus subtilis.* ATCC 14580 is the type strain of *Bacillus licheniformis.* DSM 8721 is the type strain of *Bacillus agaradhaerens.*

In yet another aspect, the present invention relates to an isolated enzyme capable of degrading rhamnogalacturonan backbones of hairy regions of pectins having the properties described above and which is free from homologous impurities, and is produced using conventional recombinant techniques.

Use in the Detergent Industry

In further aspects, the present invention relates to a detergent composition comprising the enzyme or enzyme preparation of the invention, and to a process for machine treatment of fabrics comprising treating fabric during a washing cycle of a machine washing process with a washing solution containing the enzyme or enzyme preparation of the invention.

Typically, the detergent composition of the invention comprises conventional ingredients such as surfactants (anionic, nonionic, zwitterionic, amphoteric), builders, and other ingredients, e.g. as described in WO 97/01629 which is hereby incorporated by reference.

Use in the Textile and Cellulosic Fiber Processing Industries

The enzyme of the present invention can be used in combination with other carbohydrate degrading enzymes (for instance galactanase, arabinanase, xyloglucanase, pectinase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of hairy regions of the primary cell wall. Or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The preparation of the present invention is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are desizing (for woven goods), scouring and bleaching. A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days. Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme α-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

It is contemplated that the scouring step can be carried out using the enzyme or enzyme preparation of the present invention in combination with a few other enzyme activities at a temperature of about 50° C.–80° C. and a pH of about 7–11, thus substituting or supplementing the highly causticizing agents.

Degradation or Modification of Plant Material

The enzyme or enzyme preparation according to the invention is preferably used as an agent for degradation or modification of plant cell walls or any pectin-containing material originating from plant cells walls due to the high plant cell wall degrading activity of the enzyme of the invention.

The enzyme of the present invention can be used in combination with other pectinolytic or hemicellulytic enzymes to degrade hairy regions of pectins.

The enzyme of the present invention may be used alone or together with other enzymes like glucanases, pectinases and/or hemicellulases to improve the extraction of oil from oil-rich plant material, like soy-bean oil from soy-beans, olive-oil from olives or rapeseed-oil from rape-seed or sunflower oil from sunflower.

The enzyme of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions, The separation process may be performed by use of methods known in the art.

The enzyme of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearance of processed fruit or vegetables. The consistency and appearance has been shown to be a product of the actual combination of enzymes used for processing, i.e. the specificity of the enzymes with which the enzyme of the invention is combined. Examples include the production of clear juice e.g. from apples, pears or berries; cloud stable juice e.g. from apples, pears, berries, citrus or tomatoes; and purees e.g. from carrots and tomatoes.

The enzyme of the invention may be used in modifying the viscosity of plant cell wall derived material. The viscosity reduction may be obtained by treating the pectin containing plant material with an enzyme preparation of the invention under suitable conditions for full or partial degradation of the pectin containing material.

The enzyme can be used e.g. in combination with other enzymes for the removal of pectic substances from plant fibres. This removal is essential e.g. in the production of textile fibres or other cellulosic materials. For this purpose plant fibre material is treated with a suitable amount of the enzyme of the invention under suitable conditions for obtaining full or partial degradation of pectic substances associated with the plant fibre material.

Animal Feed Additive

The enzyme of the present invention may be used for modification of animal feed and may exert their effect either in vitro (by modifying components of the feed) or in vivo. The enzyme is particularly suited for addition to animal feed compositions containing high amounts of pectic substances, e.g. feed containing plant material from soy bean, rape seed, lupin etc. When added to the feed the enzyme may significantly improve the in vivo break-down of plant cell wall material, whereby a better utilization of the plant nutrients by the animal is achieved. Thereby, the growth rate and/or feed conversion ratio (i.e. the weight of ingested feed relative to weight gain) of the animal is improved. Also, by the degradation of pectin the enzyme may improve the digestibility and uptake of non-carbohydrate feed constituents such as protein, fat and minerals.

For further description reference is made to PCT/DK 96/00443.

Wine and Juice Processing

The enzyme or enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

MATERIALS AND METHODS

Deposited Organisms and Donor Strains

*E. coli* (BLR3) comprises the plasmid containing the DNA from *B. licheniformis* ATCC 14580 encoding the enzyme of the invention (represented by SEQ ID NO 3) and is deposited as DSM 12122 on Apr. 24, 1998.

*E. coli* (clone BXR1) comprises the plasmid containing DNA from Bacillus. sp. AA386 encoding the enzyme of the invention (represented by SEQ ID NO 1) and is deposited as DSM 12123 on Apr. 24, 1998.

E. coli (clone BXR9) comprises the plasmid containing DNA from B. halodurans C4538 encoding the enzyme of the invention (represented by SEQ ID NO 13) and is deposited as DSM 12124 on Apr. 24, 1998.

E. coli (clone BXA15) comprises the plasmid containing DNA from B. halodurans KJ59 encoding the enzyme of the invention (represented by SEQ ID NO 17) and is deposited as DSM 12202 on May 29, 1998.

E. coli (clone XXR7) comprises the plasmid containing DNA from Caldocellulosiruptor sp. I24 encoding the enzyme of the invention (represented by partial SEQ ID NO 9) and is deposited as DSM 12405 on Sep. 8, 1998.

All of the above deposits were made according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany.

The donor strain Bacillus licheniformis is publicly available, for example from the deposit ATCC 14580.

The donor strain Bacillus agaradhaerens is publicly available, for example from the type strain deposit DSM 8721.

The donor strain Sorangium cellulosum is disclosed in U.S. Pat. No. 5,716,849 which is hereby incorporated by reference in its entirety. The YesW homolog gene of Sorangium cellulosum disclosed in this US patent is incomplete in that it lacks about 170 amino acids from the N terminus; a subsequence is specifically disclosed in this US patent but with unknown functionality. The partial DNA sequence of SEQ ID NO:7 is a sequence which has not been cloned by the present inventors but which is believed to encode for a rhamnogalacturonase of the present invention, since it shows sequence similarity to the enzymes identified by the present inventors.

The donor strain Streptomyces coelicolor comprises a YesW homolog gene which was submitted on Sep. 4, 1998 to the EMBL/GeneBank/DDBJ databases (Streptomyces coelicolor sequencing project, Sanger Centre, Wellcome Trust Genome Campus, Hinxton, Cambridge CB10 1SA, E-mail: barrell@sanger.ac.uk Cosmids supplied by Prof. David A. Hopwood, [3] John Innes Centre, Norwich Research Park, Colney, Norwich, Norfolk NR4 7UH, UK) but with hitherto unknown functionality (see SEQ ID NO:15 of the sequences listing herein).

The donor strain Bacillus subtilis comprises a YesW homolog gene available in the databases (TREMBL 031527; GeneBank Z99107) but with hitherto unknown functionality (see SEQ ID NO:5 of the sequences listing herein).

Other Strains

E. coli Strains

Cells of E. coli SJ2 (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321), were prepared for and transformed by electroporation using a Gene Pulser™ electroporator from BIO-RAD as described by the supplier.

XL1-Blue MRF⁻ and XLOLR E. coli strains were provided by Stratagene inc. (USA) and used according to the manufacturer's instructions.

B. subtilis Strains

DN1885. (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321).

PL1801 (B.subtilis DN1885 where the two major proteases have been inactivated).

Competent cells were prepared and transformed as described by Yasbin, R. E., Wilson, G. A. and Young, F. E. (1975) Transformation and transfection in lysogenic strains of Bacillus subtilis: evidence for selective induction of prophage in competent cells. J. Bacteriol, 121:296–304.

Plasmids pSJ1678

See International Patent Application published as WO 94/19454 which is hereby incorporated by reference in its entirety.

PUC19

See publication Yanisch-Perron et al., (1985) Gene 33:103–109 which is hereby incorporated by reference in its entirety.

pBK-CAMV

Stratagene inc. La Jolla Calif., USA.

Bacteriophage ZAP Express

Stratagene inc. La Jolla Calif., USA.

pMOL944

This plasmid is a pUB110 derivative essentially containing elements making the plasmid propagatable in Bacillus subtilis, kanamycin resistance gene and having a strong promoter and signal peptide cloned from the amyL gene of B.licheniformis ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of ordinary genetic engineering and is briefly described in the following.

Construction of pMOL944

The pUB110 plasmid (McKenzie, T. et al., 1986, Plasmid 15:93–103) was digested with the unique restriction enzyme NciI . A PCR fragment amplified from the amyL promoter encoded on the plasmid pDN1981 (P. L. Jørgensen et al.,1990, Gene, 96, p37–41.) was digested with NciI and inserted in the NciI digested pUB110 to give the plasmid pSJ2624.

The two PCR primers used have the following sequences:

LWN5494 5'-GTCGCCGGGGCGGCCGCTATCAATTGG-
    TAACTGTATCTCAGC-3'                    (SEQ ID NO:46)

LWN5495 5'-GTCGCCCGGGAGCTCTGATCAGGTAC-
    CAAGCTTGTCGACCTGCAGAATGAG-
    GCAGCAAGAAGAT-3'                      (SEQ ID NO:47)

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

LWN5938 5'-GTCGGCGGCCGCTGATCACGTAC-
    CAAGCTTGTCGACCTGCAGAATGAG-
    GCAGCAAGAAGAT-3'                      (SEQ ID NO:48)

LWN5939 5'-GTCGGAGCTCTATCAATTGGTAACTG-
    TATCTCAGC-3'                          (SEQ ID NO:49)

The plasmid pSJ2670 was digested with the restriction enzymes PstI and BclI and a PCR fragment amplified from a cloned DNA sequence encoding the alkaline amylase SP722 (disclosed in International Patent Application published as WO 95/26397 which is hereby incorporated by reference in its entirety) was digested with PstI and BclI and inserted to give the plasmid pMOL944. The two primers used for PCR amplification have the following sequence:

LWN7864 5'-AACAGCTGATCACGACTG
    ATCTTTTAGCTTGGCAC-3'     (SEQ ID NO:50)

LWN7901 5'-AACTGCAGCCGCGGCACA
    TCATAATGGGACAAATGGG-3'     (SEQ ID NO:51)

The primer #LWN7901 inserts a SacII site in the plasmid.

Determination of Rhamnogalacturonase Activity

Activity was determined by the release of blue color after incubation at 40° C. with a 0.2% slurry of AZCL-substrate on an Eppendorf thermomixer for 20 minutes followed by centrifugation and determination by spectroscopy at 620 nm.

Substrates

AZCL-potato galactan (Megazyme). The manufacturer Megazyme does not describe the composition of this substrate but the soluble potato galactan has the following composition: Galactose:Arabinose:Rhamnose:Galacturonic acid=91:2:1.7:0.35. This indicates that the substrate contains rhamnogalacturonan.

AZCL debranced arabinan from Megazyme. The composition of the soluble arabinan from sugar beets is Arabinose:Galactose:Rhamnose:Galacturonic acid=88:3:2:7. This indicates that the substrate contains rhamnogalacturonan.

Media

TY (as described in Ausubel, F. M. et al. (eds.) "Current protocols in Molecular Biology". John Wiley and Sons, 1995). LB agar (as described in Ausubel, F. M. et al. (eds.) "Current protocols in Molecular Biology". John Wiley and Sons, 1995).

BPX media is described in EP 0 506 780 (WO 91/09129).

LBPG is LB agar supplemented with 0.5% Glucose and 0.05 M potassium phosphate, pH 7.0

The following examples illustrate the invention.

EXAMPLE 1

Cloning of Rhamnogalacturonase Encoding Genes From Bacillus Species and From Caldicellulosiruptor sp.

Genomic DNA Preparation

The strains B. licheniformis, ATCC 14580, and Bacillus sp. AA386 respectively, were propagated in liquid TY medium. After 16 hours incubation at 30° C. and 300 rpm, the cells were harvested, and genomic DNA isolated by the method described by Pitcher et al. (1989). The alkalophilic strains B. halodurans KJ59 and C4538, was grown in TY with pH adjusted to approximately pH 9.7 by the addition of 50 ml of 1 M Sodium-Sesquicarbonat per 500 ml TY. After 24 hours incubation at 30° C. and 300 rpm, the cells were harvested, and genomic DNA was isolated by the method described by Pitcher et al. (1989). Caldicellulosiruptor sp. I24 was grown on DSMZ medium 640 according to the described method for growing Caldicellulosiruptor saccharolyticus (Rainey, F. A., Donnison, A. M., Janssen, P. H., Saul, D., Rodrigo, A., Bergquist, P. L., Daniel, R. M., Stackebrandt, E., Morgan, H. W., 1994, Description of Caldicellulosiruptor saccharolyticus gen. nov., sp. nov.: an obligately anaerobic, extremely thermophilic, cellulolytic bacterium. FEMS Microbiol. Lett. 120:263–266). Cells were harvested and genomic DNA isolated by the method described by Pitcher et al. (1989).

Genomic Library Construction

Libraries For B. licheniformnis, ATCC 14580, and Bacillus sp. AA386, and Bacillus halodurans C4538

Genomic DNA was partially digested with restriction enzyme Sau3A, and size-fractionated by electrophoresis on a 0.7% agarose gel. Fragments between 2 and 10 kb in size was isolated by electrophoresis onto DBAE-cellulose paper (Dretzen et al. (1981)).

Isolated DNA fragments were ligated to BamHI digested pSJ1678 plasmid DNA, and the ligation mixture was used to transform E. coli SJ2.

Libraries For Bacillus halodurans KJ59 and Caldicellulosiruptor sp. I24

The Bacillus halodurans KJ59 and the Caldicellulosiruptor sp. I24 libraries were screened as mass excised plasmid versions of the ZAP express phage libraries. The ZAP Express cloning kit used was with BamHI digested and dephosphorylated arms from Stratagene. Genomic DNA was isolated by the method of Pitcher et al., 1989. Isolated DNA was partially digested with Sau3A and size fractionated on a 1% agarose gel. DNA was excised from the agarose gel between 2 and 6 Kb and purified using Qiaspin DNA fragment purification procedure (Qiagen GMBH). 100 ng of purified, fractionated DNA was ligated with 1 ug of BamHI dephosphorylated ZAPexpress vector arms (4 degrees overnight). Ligation reaction was packaged directly with GigaPackIII Gold according to the manufacturers instructions (Stratagene). Phage libraries were titered with XL1 blue mrf⁻ (Stratagene). Mass excised libraries were made of the phage libraries according to the manufacturers instructions. The excised plasmids were screened in XLOLR cells (Stratagene) by adding kanamycin (50 ug/ml) to the selection medium described below instead of chloramphenicol.

Identification of Rhamnogalacturonase Positive Clones

The B. licheniformis, ATCC 14580, Bacillus sp. AA386, Bacillus halodurans C4538 and Bacillus halodurans KJ59 DNA libraries in E. coli, constructed as described above, were screened on LB agar plates containing 0.1% AZCL-debranched arabinan (Megazyme) and 9 µg/ml Chloramphenicol or 50 µg/ml kanamycin and incubated overnight at 37° C. The libraries were also screened on LB agar plates containing 0.1% AZCL-Galactan (potato, Megazyme). Clones expressing rhamnogalacturonase activity appeared with blue diffusion halos on both indicator plates. The plasmids of these positive clones were isolated by Qiagen plasmid spin preps on 1 ml of overnight culture broth (cells incubated at 37° C. in LB with 9 µg/ml Chloramphenicol or 50 µg/ml kanamycin and shaking at 250 rpm).

The positive clones were further characterised by DNA sequencing of the cloned genomic DNA fragments.

Identification of Rhamnogalacturonase Gene Fragments From Caldicellulosiruptor sp. I24

Partial sequences with similarity to rhamnogalacturonase genes of the invention, were identified by sequencing recombinant plasmids of the Caldicellulosiruptor sp. library.

Nucleotide Sequence Analysis

The nucleotide sequences of the genomic rhamnogalacturonan clones were determined from both strands by the dideoxy chain-termination method (Sanger, F., Nicklen, S., and Coulson, A. R. (1977) Proc. Natl. Acad. Sci. U. S. A. 74, 5463–5467) using 500 ng of Qiagen-purified template (Qiagen, USA), the Taq deoxy-terminal cycle sequencing kit (Perkin-Elmer, USA), fluorescent labelled terminators and 5 pmol of vector polylinker primers (Stratagene, USA) or synthetic oligonucleotide primers.

Analysis of the sequence data was performed with the DNA Star analysis package (WWW.dnastar.com) or with the GCG-Unix software package (Wisconsin Package Version 9.1, Genetics Computer Group (GCG), Madison, Wis.) according to Devereux et al., 1984.

Based on this sequence analysis it was found that the rhamnogalacturonase enzymes of the present invention represents two novel families of rhamnogalacturonases. In this context, one family is denoted Subfamily A and another family is denoted Subfamily B. In the attached sequence listings the mature enzyme protein represented by SEQ ID NOS: 2, 4, 6, 8, 10, 12, 14 and 16, respectively, belongs to Subfamily A; and SEQ ID NOS: 18 and 20 represent Subfamily B.

The sequence of the *B. licheniformis* (BLR3) clone encoding the mature enzyme protein is shown in SEQ ID NO:3. The derived protein sequence is shown in SEQ ID NO:4. The sequence of the Bacillus sp. AA386 clone (BXR1) encoding the mature protein is shown in SEQ ID NO:1. The derived protein sequence is shown in SEQ ID NO:2. The sequence of the *Bacillus halodurans* C4538 clone encoding the mature protein is shown in SEQ ID NO:13. The derived protein sequence is shown in SEQ ID NO:14. The sequence of the *Bacillus halodurans* KJ59 clone encoding the mature protein is shown in SEQ ID NO:17. The derived protein sequence is shown in SEQ ID NO:18. The partial sequence of a Caldocellulosiruptor sp. gene is shown in SEQ ID NO:9. The derived partial protein sequence is shown in SEQ ID NO:10. The partial sequence of another Caldocellulosiruptor sp. gene is shown in SEQ ID NO:11. The derived partial protein sequence is shown in SEQ ID NO:12. The partial sequence of the *Bacillus agaradhaerens* gene is shown in SEQ ID NO:19. The derived partial protein sequence is shown in SEQ ID NO:20 (Corrected for reading frame skips).

Based on sequence analysis, the following known genes of hitherto unknown functionality were identified: the *Bacillus subtilis* YesW gene (TREMBL: 031526; GeneBank: Z99107) represented by the DNA sequence of SEQ ID NO:5 and the derived protein sequence of SEQ ID NO:6; and the *Streptomyces coelicolor* YesW gene (E1319264; GeneBank: AL031515) represented by the DNA sequence of SEQ ID NO:15 (GTG is apparent start codon) and the derived protein sequence of SEQ ID NO:16 (Valine is first amino acid); and the *Sorangium cellulosum* gene represented by the partial sequence shown in SEQ ID NO:7. The derived partial protein sequence is shown in SEQ ID NO:8.

Subcloning and Expression in *E. coli* of the YesW Gene From *Bacillus subtilis* Encoding the Enzyme of the Invention The YesW encoding DNA sequence was PCR amplified using the PCR primer set consisting of two oligo nucleotides:

YesW upper EcoRI primer:

5'-TCGCCG<u>GAATTC</u>GTGCAGTGTCCGAAA
TAGGCAGATGC-3' (SEQ ID NO:52)

YesW lower SphI primer:

5'-TCGCCG<u>GCATGC</u>GTTCTGTCTGTACCG
CAATCAAACC-3' (SEQ ID NO:53)

Restriction Sites EcoRI and SphI Are Underlined

Chromosomal DNA isolated from *B. subtilis* DN1885 as described (Pitcher et al., 1989) was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 µM of each dNTP, 2.5 units of AmpliTaq polymerase (Perkin-Elmer, Cetus, USA) and 100 pmol of each primer The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment size 2.06 kb indicated proper amplification of the gene segment.

Subcloning of PCR Fragment

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. 5 µg of pUC19 and twentyfive-µl of the purified PCR fragment was digested with EcoRI and SphI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the EcoRI-SphI digested and purified pUC19. The ligation was performed overnight at 16° C. using 0.5 µg of each DNA fragment, 1 U of T4 DNA ligase and T4 ligase buffer (Boehringer Mannheim, Germany).

The ligation mixture was used to transform *E.coli* SJ2 by electroporation as described above. The transformed cells were plated onto LBPG with 50 µg/ml of ampicillin. After 18 hours incubation at 37° C. colonies were seen on plates. Several clones were analyzed by isolating plasmid DNA from overnight culture broth.

One clone called PL3142 contained the expected plasmid pPL3142 confirmed by restriction analysis and DNA sequencing. PL3142 was re-streaked onto two sets of LB agar plates; one containing 0.5% AZCL-debranched arabinan (Megazyme), the other containing 0.5% AZCL-potato galactan (Megazyme). The clone PL3142 showed activity on both plates.

Sequence Similarities

The deduced amino acid sequences of the rhamnogalacturonan hydrolases of the present invention show the following similarity when compared to the *Bacillus licheniformis* rhamnogalacturonan hydrolase (SEQ ID NO:4) in the case of Subfamily A members and *Bacillus halodurans* KJ59 (SEQ ID NO:18) in the case of Subfamily B members:

| | SEQ ID NO:4 | | SEQ ID NO:18 | |
|---|---|---|---|---|
| SEQ ID NO:2 | 67.3 | 71.7 | SEQ ID NO:20 | 73.8 80.0 |
| SEQ ID NO:6 | 77.4 | 81.8 | | |
| SEQ ID NO:8 | 58.0 | 64.0 | | |
| SEQ ID NO:10 | 64.0 | 68.5 | | |
| SEQ ID NO:12 | 48.0 | 57.2 | | |
| SEQ ID NO:14 | 62.7 | 69.8 | | |
| SEQ ID NO:16 | 59.5 | 65.5 | | |

Values are in percent identity/percent similarity respectively compared to the *Bacillus licheniformis* rhamnogalacturonan hydrolase (SEQ ID NO:4) and *Bacillus halodurans* KJ59 (SEQ ID NO:18), respectively. Only the core region (amino acid sequence minus the secretion signal, if present) was analyzed. The GAP program in the GCG package ver. 9.1 (Devereux et al., 1984) was used. The standard PAM table blosum62 with a gap creation penalty of 12 and a gap extension penalty of 4 was employed throughout.

EXAMPLE 2

Subcloning and Expression in *B. subtilis* of the YesW Gene From *Bacillus subtilis* Encoding the Enzyme of the Invention; Purification and Characterisation of the Enzyme The YesW encoding DNA sequence was PCR amplified using the PCR primer set consisting of these two oligo nucleotides:

YesW .upper.SacII

5'-GCAG<u>CCGCGG</u>CAGAAGGGGCAGC GCGGCAGATGG-3' (SEQ ID NO:54)

YesW .lower.NotI

5'-TCGCCG<u>GCGGCCGC</u>GTTCTGTCTG TACCGCAATCAAACC-3' (SEQ ID NO:55)

Restriction Sites SacII and NotI Are Underlined

Chromosomal DNA isolated from *B. subtilis* DN1885 as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 μM of each dNTP, 2.5 units of AmpliTaq polymerase (Perkin-Elmer, Cetus, USA) and 100 pmol of each primer.

The PCR reaction was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-μl aliquots of the amplification product was analysed by electrophoresis in 0.7% agarose gels (NuSieve, FMC). The appearance of a DNA fragment size 1.866 kb indicated proper amplification of the gene segment.

Subcloning of PCR Fragment

Fortyfive-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5.

5 μg of pMOL944 and twentyfive-μl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent *B.subtilis* PL1801 cells. The transformed cells were plated onto LBPG with 10 μg/ml of kanamycin. After 18 hours incubation at 37° C. colonies were seen on plates. Several clones were analyzed by isolating plasmid DNA from overnight culture broth.

One such positive clone was restreaked several times on agar plates as used above, this clone was called PL3151. The clone PL3151 was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for *B.subtilis* plasmid preparations. This DNA was sequenced and confirmed that the sequence corresponds to the mature part of the *B. subtilis* YesW gene (SEQ ID NO:5).

PL3151 was grown in 25×200 ml BPX media with 10 μg/ml of Kanamycin in 500 ml two baffled shakeflasks for 5 days at 37° C. at 300 rpm.

Purification and Characterisation 600 ml of culture broth was purified as follows: The pH was first adjusted to 5.5, using acetic acid and then 5 ml of cationic agent (C521 10%) and 5 ml of anionic agent (A130 0.1%) were added during agitation for flocculation. The flocculated material was separated by centrifugation using a Sorval RC 3B centrifuge at 10000 rpm for 30 min at 6° C. The resulting supernatant contained substantial amounts of a 67 kDa protein visualized on SDS-PAGE.

The supernatant was clarified using Whatman glass filters GF/D and C before final concentration on a filtron UF membrane with a cut off of 10 kDa. The total volume of 200 ml was adjusted to pH 8.5 using NaOH. The enzyme solution was applied to a 50 ml HPQ Sepharose column. All the 67 kDa peptide ran through the column that had been equilibrated with 25 mM Tris pH 8.5. The HPQ sepharose purification step was repeated and the fractions containing the 67 kDa protein were pooled and concentrated resulting in a rhamnogalacturonan hydrolase enzyme that was approximately 90% pure but which also contained some *Bacillus subtilis* rhamnogalacturonase (0.1 mg/ml). The preparation contained 4.7 mg/ml of the 67 kDa rhamnogalacturonan hydrolase enzyme.

The purified rhamnogalacturonase enzyme has activity on AZCL galactan and AZCL debranched arabinan as well as on rhamnogalacturonan.

Based on the DNA sequence SEQ ID NO. 5, the following data was obtained:

Molar extinction coefficient: 116780

Molecular weight: 63566 Dalton pI (estimated): 5.2.

EXAMPLE 3

Subcloning and Expression in *B. subtilis* of the YesW Rhamnogalacturonase Gene From Bacillus sp. AA386 (*E. coli* Clone Deposition No. DSM 12123); Purification and Characterisation of the Enzyme The YesW encoding DNA sequence was PCR amplified using the PCR primer set consisting of these two oligo nucleotides:

YesW .upper.PstI

5'-CTCG<u>CTGCAG</u>CAGCGGCGGCACCCA GACAGGCGGAGAACATTAGC-3' (SEQ ID NO:56)

YesW .lower.NotI

5'-CGACGACGT<u>GCGGCCGC</u>CATTATGCG CCTGCTCTTCG-3' (SEQ ID NO:57)

Restriction Sites PstI and NotI Are Underlined

Plasmid DNA isolated from *E. coli* clone BXR1 (DSM 12123) as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 μM of each dNTP, 2.5 units of AmpliTaq polymerase (Perkin-Elmer, Cetus, USA) and 100 pmol of each primer.

The PCR reaction was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment size 1.941 kb indicated proper amplification of the gene segment.

Subcloning of PCR Fragment

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5.

5 µg of pMOL944 was digested with PstI and NotI and twentyfive-µl of the purified PCR fragment was digested with PstI (partial digest) and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the PstI-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent B.subtilis PL1801 cells. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called PL2988. The clone PL2988 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for B. subtilis plasmid preparations. This DNA was sequenced and confirmed that the sequence corresponds to the mature part of the Bacillus sp. AA386 YesW gene (SEQ ID NO:1).

PL2988 was grown in 25×200 ml BPX media with 10 µg/ml of Kanamycin in 500 ml two baffled shakeflasks for 5 days at 37° C. at 300 rpm.

Purification and Characterisation 600 ml of culture broth was purified as follows: The pH was adjusted to 5.5, using acetic acid and 5 ml of cationic agent (C521 10%) and 5 ml of anionic agent (A130 0.1%) was added during agitation for flocculation. The flocculated material was separated by centrifugation using a Sorval RC 3B centrifuge at 10000 rpm for 30 min at 6° C. The resulting supernatant contained a substantial amount of a 63 kDa peptide as visualized by SDS-PAGE.

The supernatant was clarified using Whatman glass filters GF/D and C before final concentration on a filtron UF membrane with a cut off of 10 kDa. The total volume of 140 ml was adjusted to pH 8.5 with NaOH and was applied to a 50 ml HPQ Sepharose column. All the 63 kDa peptide ran through the column equilibrated with 25 mM Tris pH 8.5. The experiment was repeated and some of the activity ran through once again, however, a pure rhamnogalacturonan hydrolase was eluted from the column by using a NaCl gradient. The active eluted fractions containing the 63 kDa protein, as visualized in SDS-PAGE, was pooled and concentrated resulting in an essentially pure protein which contained no *Bacillus subtilis* rhamnogalacturonase. The enzyme preparation contained 8 mg/ml of the 63 kDa rhamnogalacturonase.

The pure rhamnogalacturonase enzyme has activity on AZCL Galactan and AZCL debranched arabinan as well as on rhamnogalacturonan.

Based on the DNA sequence, SEQ ID NO. 1, the following data was obtained:
Molar extinction coefficient: 128280
Molelcular weight: 63453 Dalton
pI (estimated): 5.2.

EXAMPLE 4

Subcloning and Expression in *B. subtilis* of the YesW Rhamnogalacturonase Gene From *Bacillus lichenifoxmis* (*E. coli* Clone Deposition No. DSM 12122); Purification and Characterisation of the Enzyme The YesW encoding DNA sequence was PCR amplified using the PCR primer set consisting of these two oligo nucleotides:

YesW .upper.SacII

| 5'-GCAG<u>CCGCGG</u>CAGACGGGCGGACGG CTGCGCAGG-3' | (SEQ ID NO:58) |

YesW .lower.NotI

| 5'-GTGG<u>GCGGCCGC</u>GCCTGAGAAAAT CCGTAGCCAGCACC-3' | (SEQ ID NO:59) |

Restriction Sites SacII and NotI Are Underlined

Plasmid DNA isolated from *E.coli* clone BLR3 (DSM 12122) as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM MgCl$_2$, 0.01% (w/v) gelatin) containing 200 µM of each dNTP, 2.5 units of AmpliTaq polymerase (Perkin-Elmer, Cetus, USA) and 100 pmol of each primer.

The PCR reaction was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC). The appearance of a DNA fragment size 2.028 kb indicated proper amplification of the gene segment.

Subcloning of PCR Fragment

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5.

5 µg of pMOL944 and twentyfive-µl of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent B.subtilis PL1801 cells. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called PL3149. The clone PL3149 was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for B.subtilis plasmid preparations. This DNA was sequenced and shown to correspond to the mature part of the B. licheniformis YesW gene (SEQ ID NO:3).

PL3149 was grown in 25×200 ml BPX media with 10 μg/ml of Kanamycin in 500 ml two baffled shakeflasks for 5 days at 37° C. at 300 rpm.

Purification and Characterisation 600 ml of culture broth was purified as follows: The pH was adjusted to 5.5, using acetic acid. 5 ml of cationic agent (C521 10%) and 5 ml of anionic agent (A130 0.1%) were added during agitation for flocculation. The flocculated material was separated by centrifugation using a Sorval RC 3B centrifuge at 10000 rpm for 30 min at 6° C. The resulting supernatant contained substantial amounts of a 64 kDa peptide as visualized by SDS-PAGE.

The supernatant was clarified using Whatman glass filters GF/D and C before final concentration on a filtron UF membrane with a cut off of 10 kDa. The total volume of 140 ml was adjusted to pH 8.5 with NaOH. The enzyme solution was applied to a 50 ml HPQ Sepharose column. All the 64 kDa peptide ran through the column equilibrated with 25 mM Tris pH 8.5. The experiment was repeated and some of the activity ran through once again however, a pure rhamnogalaturonase was eluted from the column by using a NaCl gradient. The active eluted fractions containing the 64 kDa protein, as visualized by SDS-PAGE, was pooled and concentrated which resulted in an essentially pure enzyme containing no Bacillus subtilis rhamnogalacturonase. The enzyme preparation contained 2.7 mg/ml of the 64 kDa rhamnogalacturonase.

The pure rhamnogalaturonase enzyme has activity on AZCL Galactan and AZCL debranched arabinan as well as on rhamnogalacturonan.

Based on the DNA sequence, SEQ ID NO. 3, the following data was obtained:

Molar extinction coefficient: 120620
Moelcular weight: 64287 Dalton
pI (estimated): 5.4.

EXAMPLE 5

Subcloning and Expression in B. subtilis of the Rhamnogalacturonase Gene From Bacillus halodurans KJ59; Purification and Characterisation of the Enzyme The rhamnogalacturonase encoding DNA sequence was PCR amplified using the PCR primer set consisting of these two oligo nucleotides:

YesW .upper.PstI

5'-GCGCTCTGCAGCAGCGGCGAAATGAAG
   TGGTGAATGCAAGGGATTTTGG-3'       (SEQ ID NO:60)

YesW .lower.NotI

5'-GTCAGGCGTGCGGCCGCGGTGTAGAGG
   TGCGATGATGGATGGG-3'             (SEQ ID NO:61)

Restriction Sites SacII and NotI Are Underlined

Plasmid DNA isolated from E.coli clone BXA15 (DSM 12202) as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 μM of each dNTP, 2.5 units of AmpliTaq polymerase (Perkin-Elmer, Cetus, USA) and 100 pmol of each primer.

The PCR reaction was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-μl aliquots of the amplification product was analysed by electrophoresis in 0.7% agarose gels (NuSieve, FMC). The appearance of a DNA fragment size 1.778 kb indicated proper amplification of the gene segment.

Subcloning of PCR Fragment

Fortyfive-μl aliquots of the PCR products generated as described above were purified using QIAquick PCR purification kit (Qiagen, USA) according to the manufacturer's instructions. The purified DNA was eluted in 50 μl of 10 mM Tris-HCl, pH 8.5.

5 μg of pMOL944 and twentyfive-μl of the purified PCR fragment was digested with PstI and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the PstI-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent B.subtilis PL1801 cells. The transformed cells were plated onto LBPG-10 μg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called PL2990. The clone PL2990 was grown overnight in TY-10 μg/ml Kanamycin at 37° C., and next day 1 ml of cells were used to isolate plasmid from the cells using the Qiaprep Spin Plasmid Miniprep Kit #27106 according to the manufacturers recommendations for B.subtilis plasmid preparations. This plasmid DNA was sequenced and confirmed the sequence corresponds to the mature part of the B. halodurans KJ59 gene (SEQ ID NO:17).

PL2990 was grown in 25×200 ml BPX media with 10 μg/ml of Kanamycin in 500 ml two baffled shakeflasks for 5 days at 37° C. at 300 rpm.

Purification and Characterisation 600 ml of culture broth was purified as follows: The pH was adjusted to 5.5, using acetic acid. 5 ml of cationic agent (C521 10%) and 5 ml of anionic agent (A130 0.1%) were added during agitation for flocculation. The flocculated material was separated by centrifugation using a Sorval RC 3B centrifuge at 10000 rpm for 30 min at 6° C. The resulting supernatant contained substantial amounts of a 42 kDa peptide as visualized by SDS-PAGE.

The supernatant was clarified using Whatman glass filters GF/D and C before final concentration on a filtron UF membrane with a cut off of 10 kDa. The total volume of 140 ml was washed with deionized water until the conductivity was below 1 mSi. The enzyme solution was applied to a 50 ml HPS Sepharose column equilibrated with 25 mM sodium acetate buffer pH 5.5. All the 42 kDa protein bound to the column and the enzyme was eluted using a sodium chloride gradient. The active eluted fractions containing the 42 kDa protein, as visualized by SDS-PAGE, were pooled and concentrated resulting in approximately a 25% pure enzyme preparation with trace amounts of *Bacillus subtilis* rhamnogalacturonase. The preparation contained 0.4 mg/ml of the 42 kDa rhamnogalacturonase.

The partially pure rhamnogalaturonase enzyme has activity on AZCL Galactan and AZCL debranched arabinan as well as on rhamnogalacturonan.

Based on the DNA sequence SEQ. ID NO. 17 the following data was obtained:
Molar extinction coefficient: 15930.

EXAMPLE 6
Degradation of Hairy Regions From Apples and Rhamnogalacturonan Obtained From Megazyme By the Enzyme of the Invention Hairy regions from apples (MHR), which mainly contain arabinan side chains on the rhamnogalacturonan backbone, were extracted essentially as described (Schols, H.A. et al (1990)). Rhamnogalacturonan (RG) prepared from soy bean pectin was obtained from Megazyme.

MHR and RG were saponified (MHR-S and RG-S, respectively) according to Kofod et al (1994).

The rhamnogalacturonan hydrolase enzymes from Bacillus sp.

AA386 (BXR1), *B. lichenifoxmis* (BLR3), *B. subtilis* (BSR5) and *B. halodurans* KJ59 (BXA15) were produced and purified as described in examples 2–5. Enzyme activity was determined using 0.2% AZCL potato galactan in 0.1 M glycin pH 9 buffer and incubation at 40° C. for 15 min. $OD_{620}$ was measured on the supernatant. For this experiment, 1 unit was defined as the amount of enzyme giving an increase in $OD_{620}$ of 0.35.

1 ml aliquots of a 0.75% solution of MHR, MHR-S, RG and RG-S, respectively, in 0.1 M glycin pH 9 buffer were incubated in thermomixers with the enzymes BXR1, BLR3, BSR5 and BXA15 at 30° C. for 1, 2, 4 and 24 hours. The enzyme dose was based on the activity on AZCL potato galactan i.e. 1 unit per ml substrate.

Figure 2:
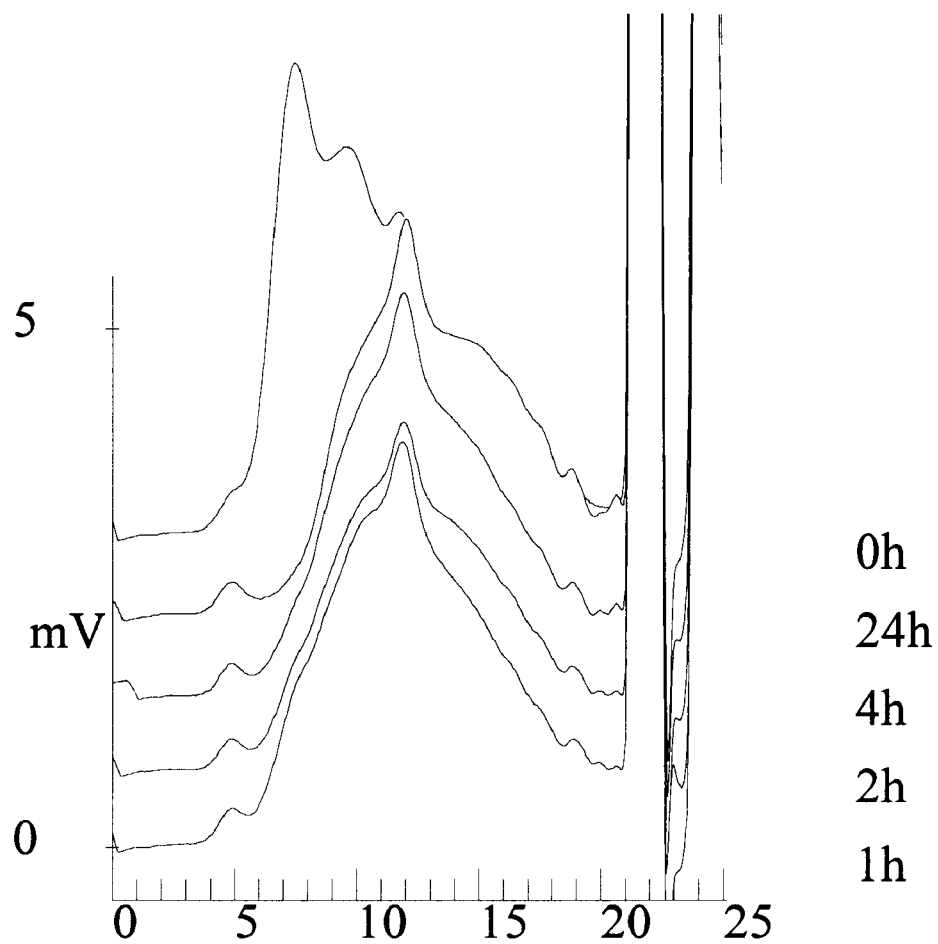
FIG. 2 shows high performance size exclusion chromatography (HPSEC) of MHR degraded by the rhamnogalacturonan hydrolase from *Bacillus licheniformis* (BLR3).
Figure 3:
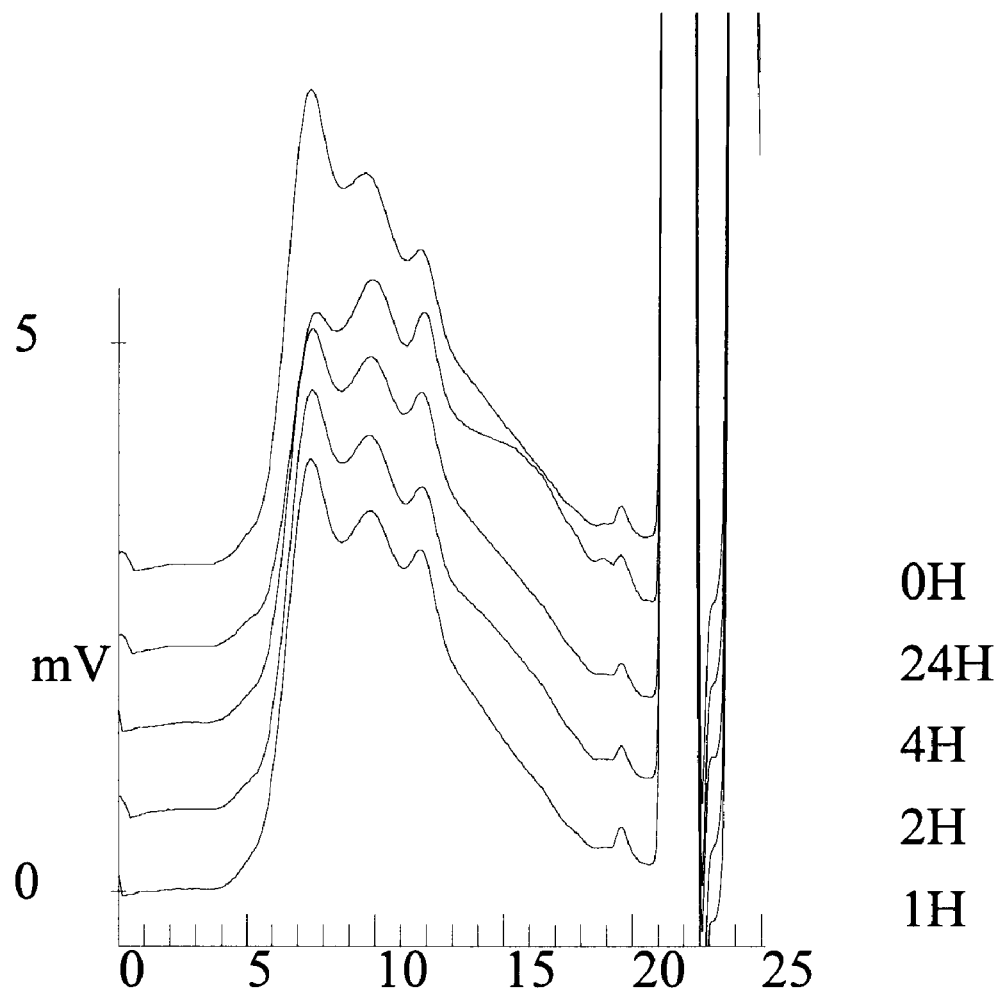
FIG. 3 shows high performance size exclusion chromatography (HPSEC) of MHR degraded by the rhamnogalacturonan hydrolase from *Bacillus subtilis* (BSR5).
Figure 4:
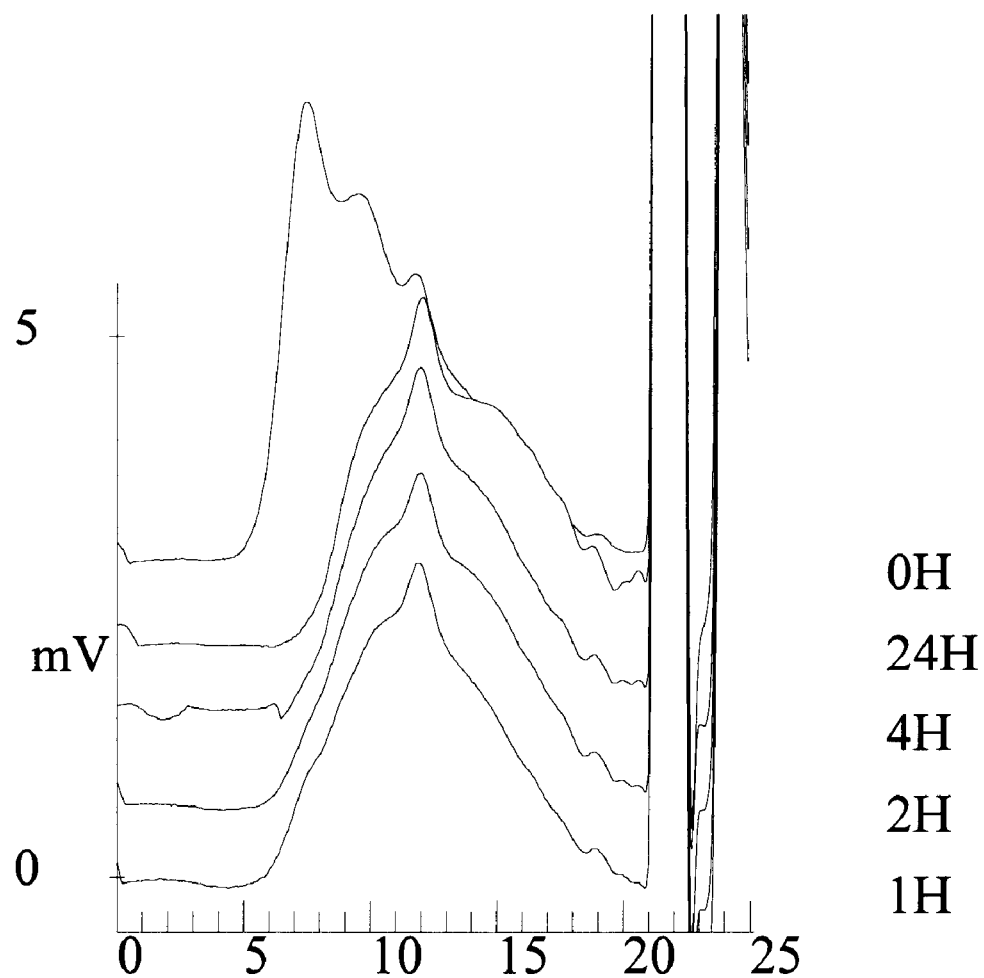
FIG. 4 shows high performance size exclusion chromatography (HPSEC) of MHR degraded by the rhamnogalacturonan hydrolase from *Bacillus halodurans* KJ59 (BXA15).
Figure 5:
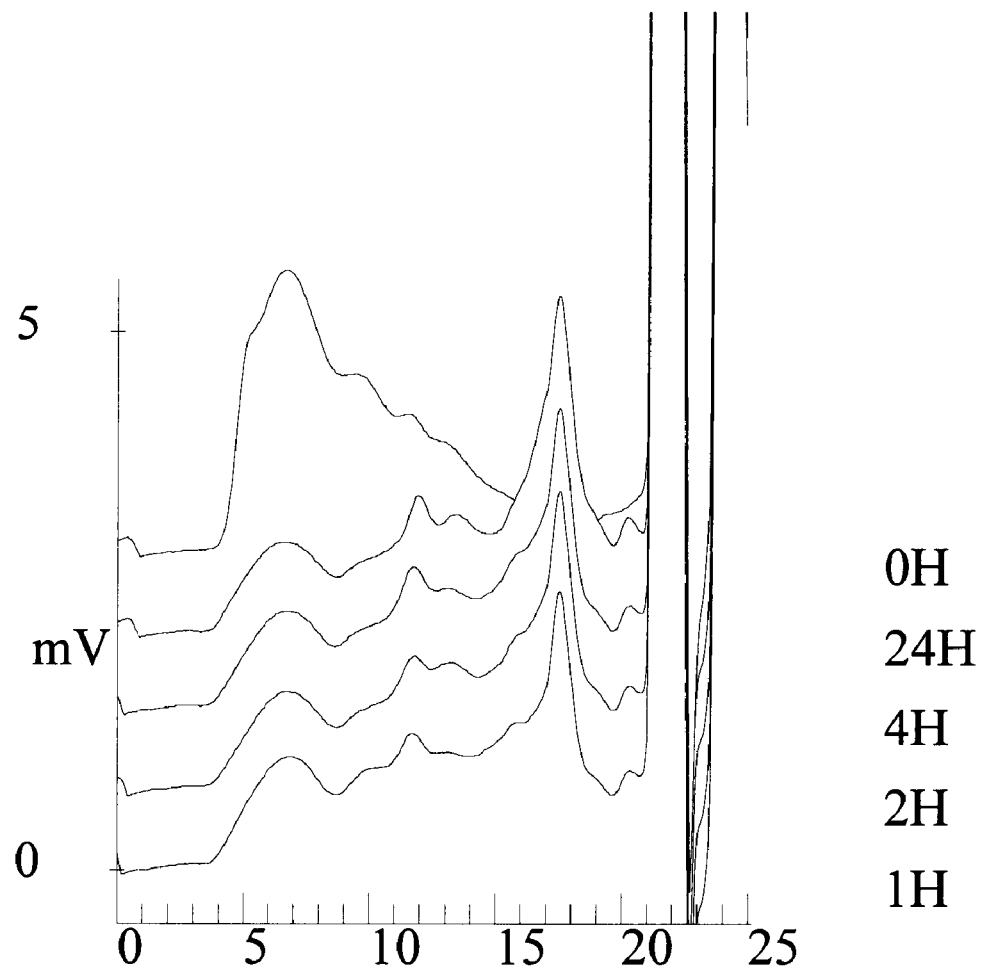
FIG. 5 shows high performance size exclusion chromatography (HPSEC) of saponified hairy regions from apples (MHR-S) degraded by the rhamnogalacturonan hydrolase from Bacillus sp. AA 386 (BXR1).
Figure 6:
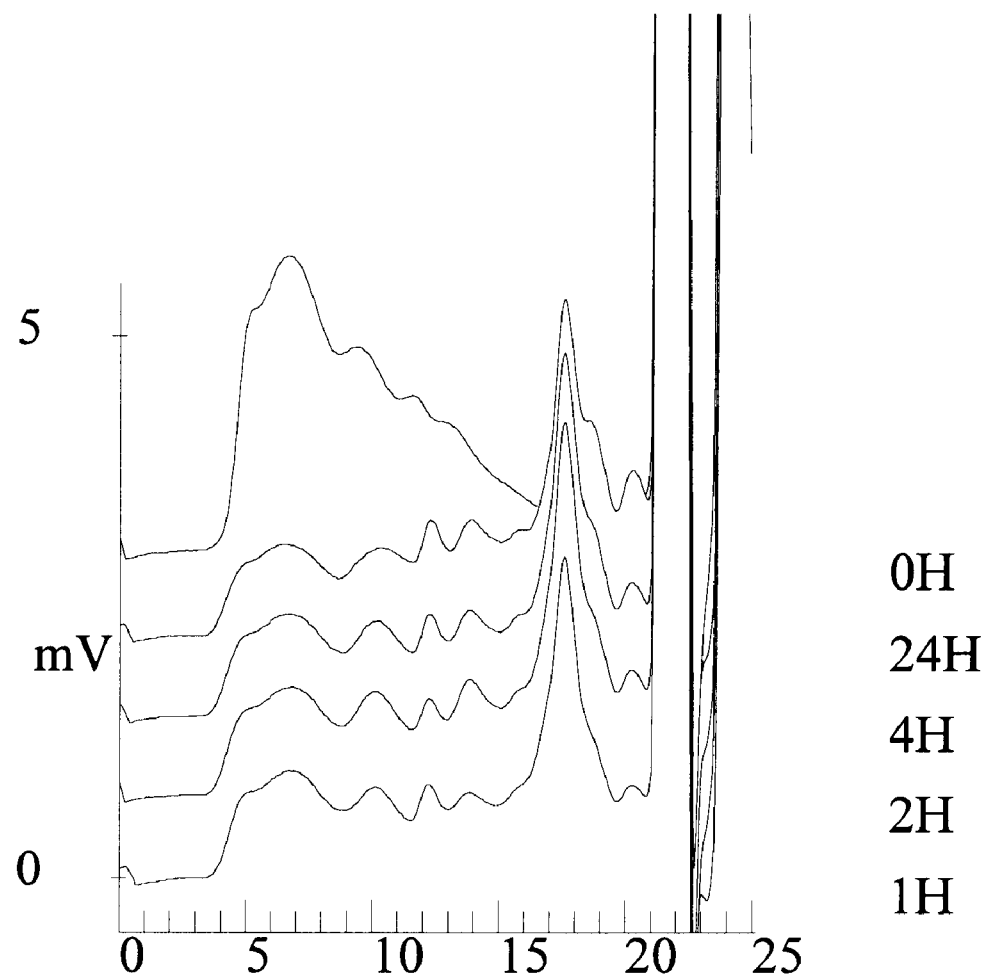
FIG. 6 shows high performance size exclusion chromatography (HPSEC) of MHR-S degraded by the rhamnogalacturonan hydrolase from *Bacillus licheniformis* (BLR3).
Figure 7:
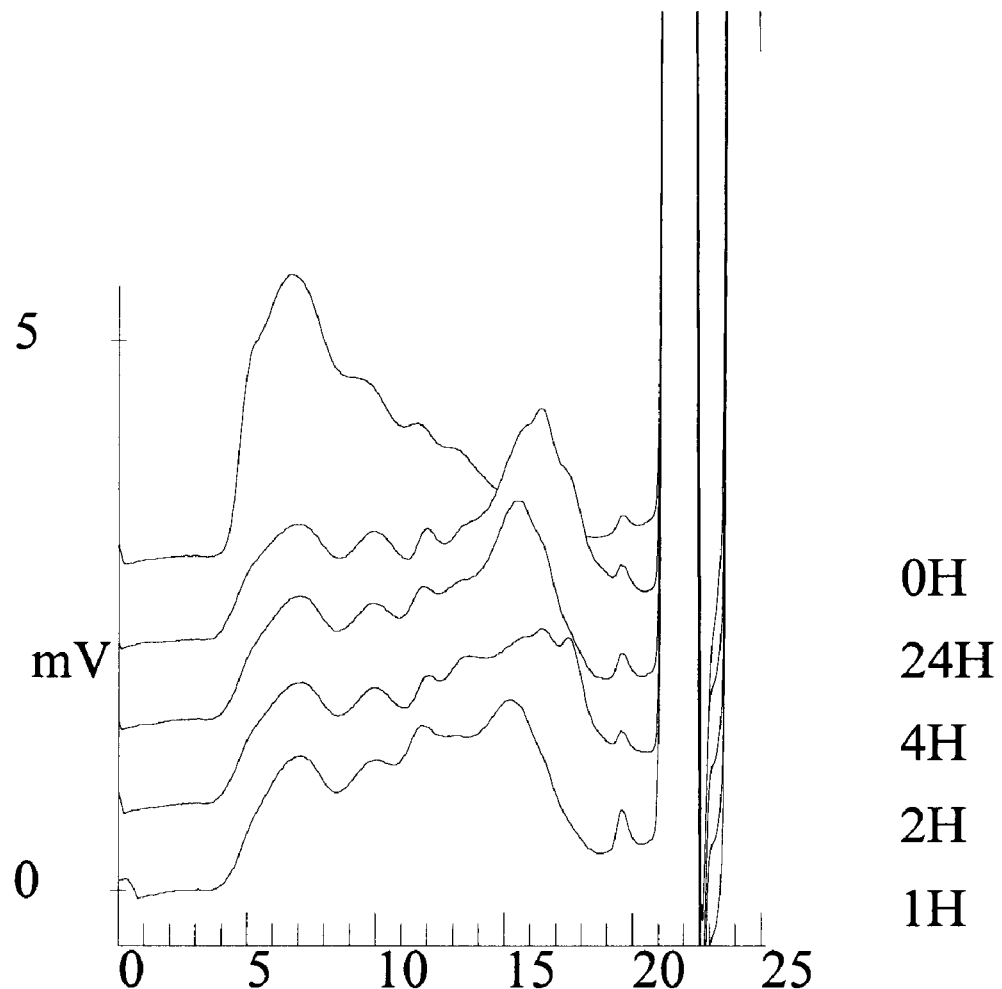
FIG. 7 shows high performance size exclusion chromatography (HPSEC) of MHR-S degraded by the rhamnogalacturonan hydrolase from *Bacillus subtilis* (BSR5).
Figure 8:
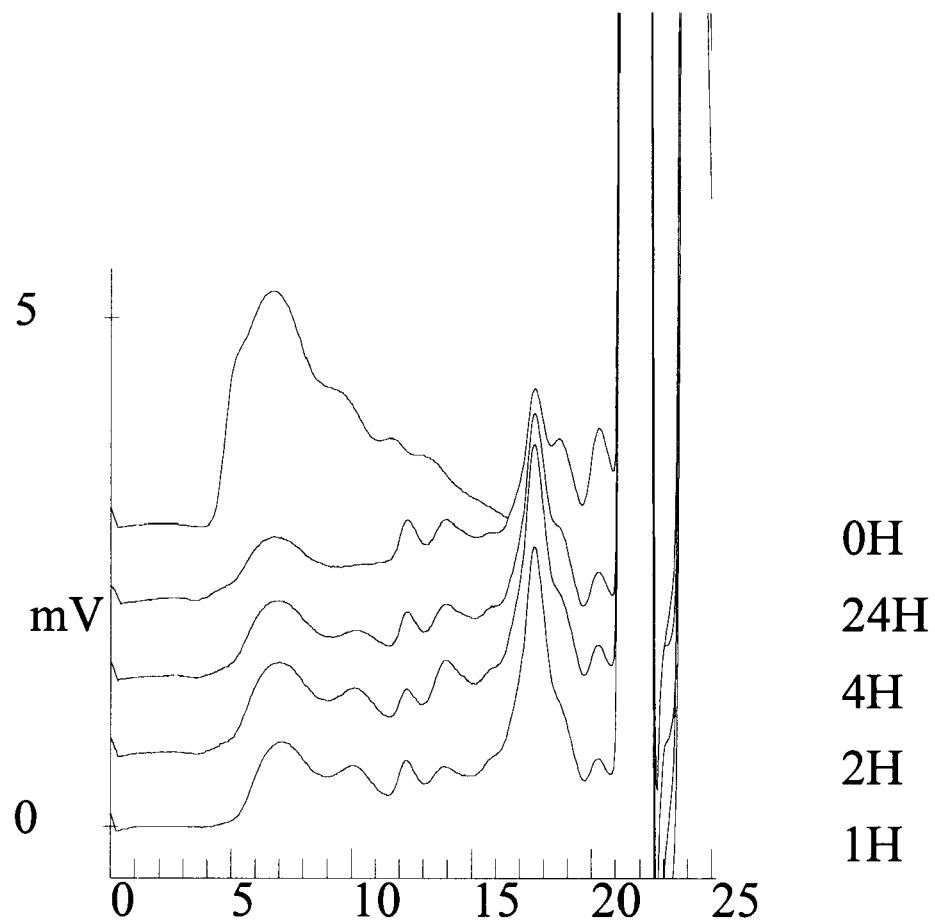
FIG. 8 shows high performance size exclusion chromatography (HPSEC) of MHR-S degraded by the rhamnogalacturonan hydrolase from *Bacillus halodurans* KJ59 (BXA15).

Degradation products were analyzed by high performance size exclusion chromatography (HPSEC) as described in Kauppinen et al (1995). The HPSEC analysis of MHR incubated with the enzymes showed that MHR was depolymerized to some extent by all four enzymes (FIGS. 1, 2, 3, 4). Further, the HPSEC analysis showed that the enzymes were capable of extensively degrading the MHR-S substrate resulting in the formation of oligomers (FIGS. 5, 6, 7, 8). In MHR-S both methyl and acetyl esters are removed, and therefore, it cannot be concluded whether both or only one type of ester linkages inhibit the enzyme action.

Figure 9:
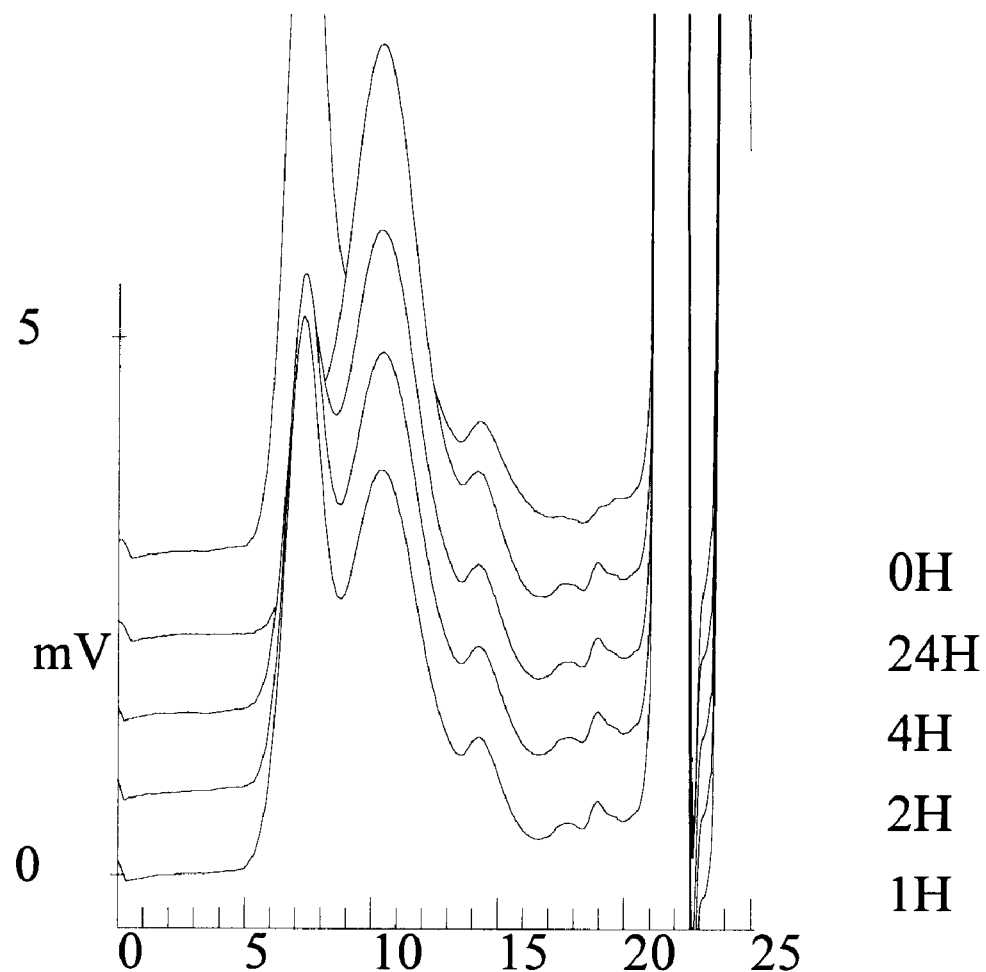
FIG. 9 shows high performance size exclusion chromatography (HPSEC) of rhamnogalacturonan obtained from Megazyme (RG) degraded by the rhamnogalacturonan hydrolase from Bacillus sp. AA 386 (BXR1).
Figure 10:
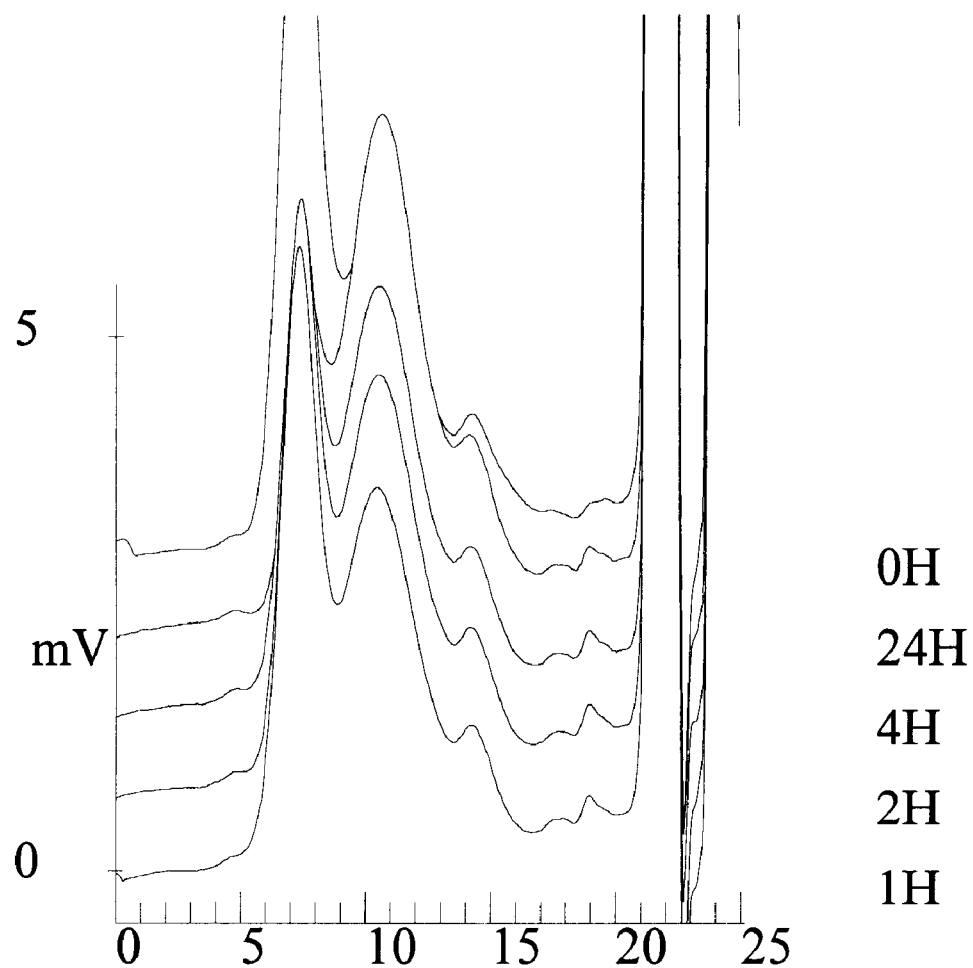
FIG. 10 shows high performance size exclusion chromatography (HPSEC) of RG degraded by the rhamnogalacturonan hydrolase from *Bacillus licheniformis* (BLR3).
Figure 11:
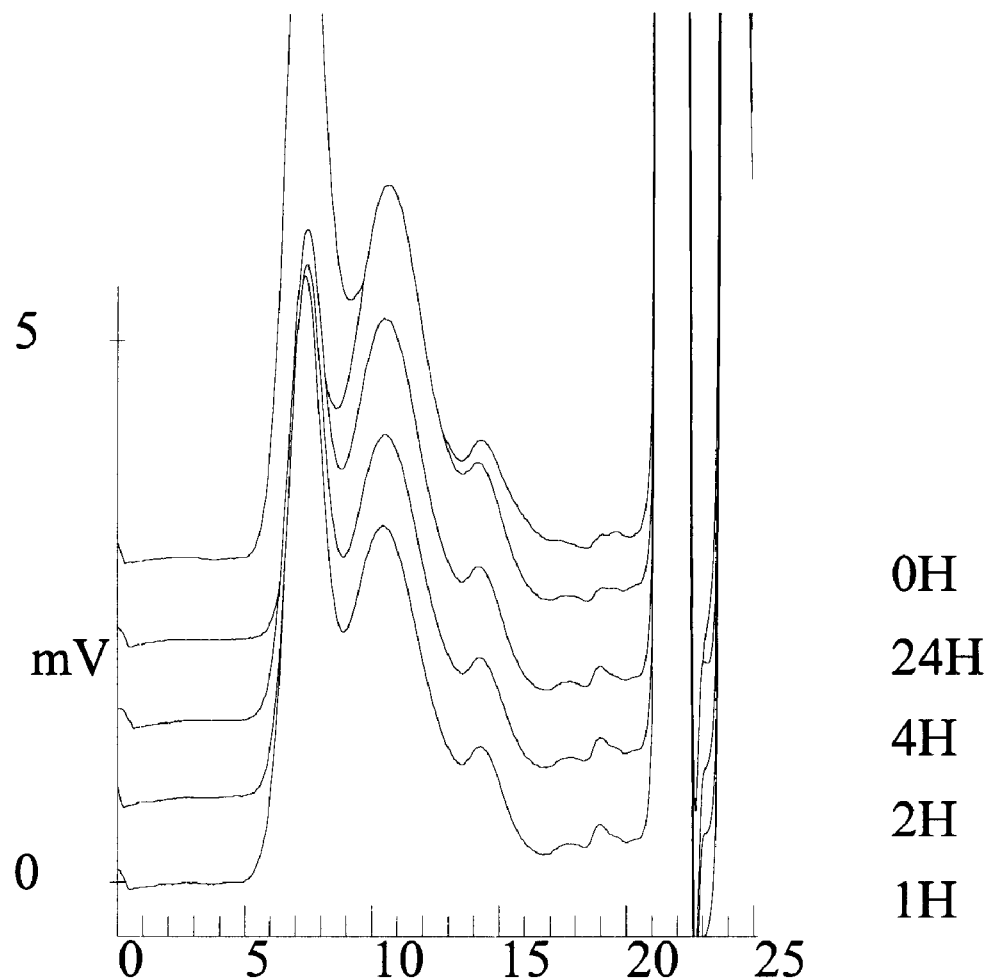
FIG. 11 shows high performance size exclusion chromatography (HPSEC) of RG degraded by the rhamnogalacturonan hydrolase from *Bacillus halodurans* KJ59 (BXA15).
Figure 12:
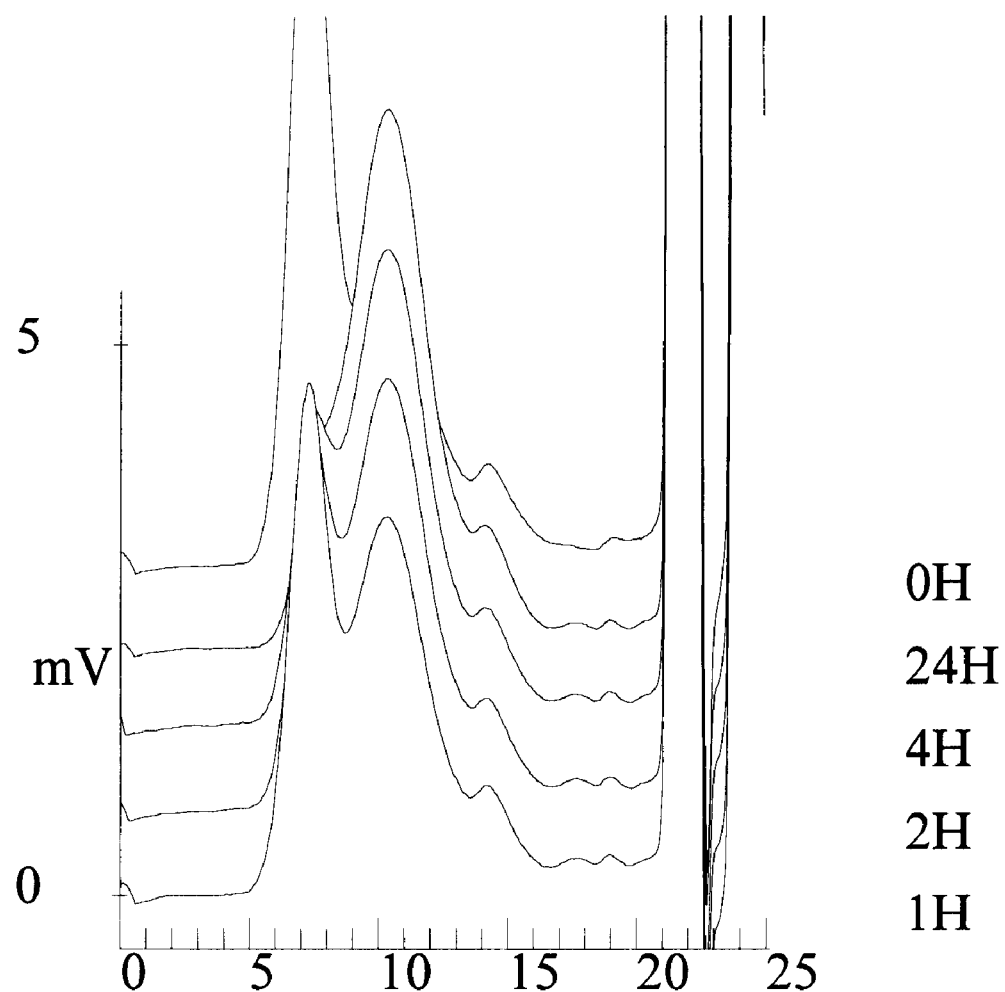
FIG. 12 shows high performance size exclusion chromatography (HPSEC) of saponified RG (RG-S) degraded by the rhamnogalacturonan hydrolase from Bacillus sp. AA 386 (BXR1).
Figure 13:
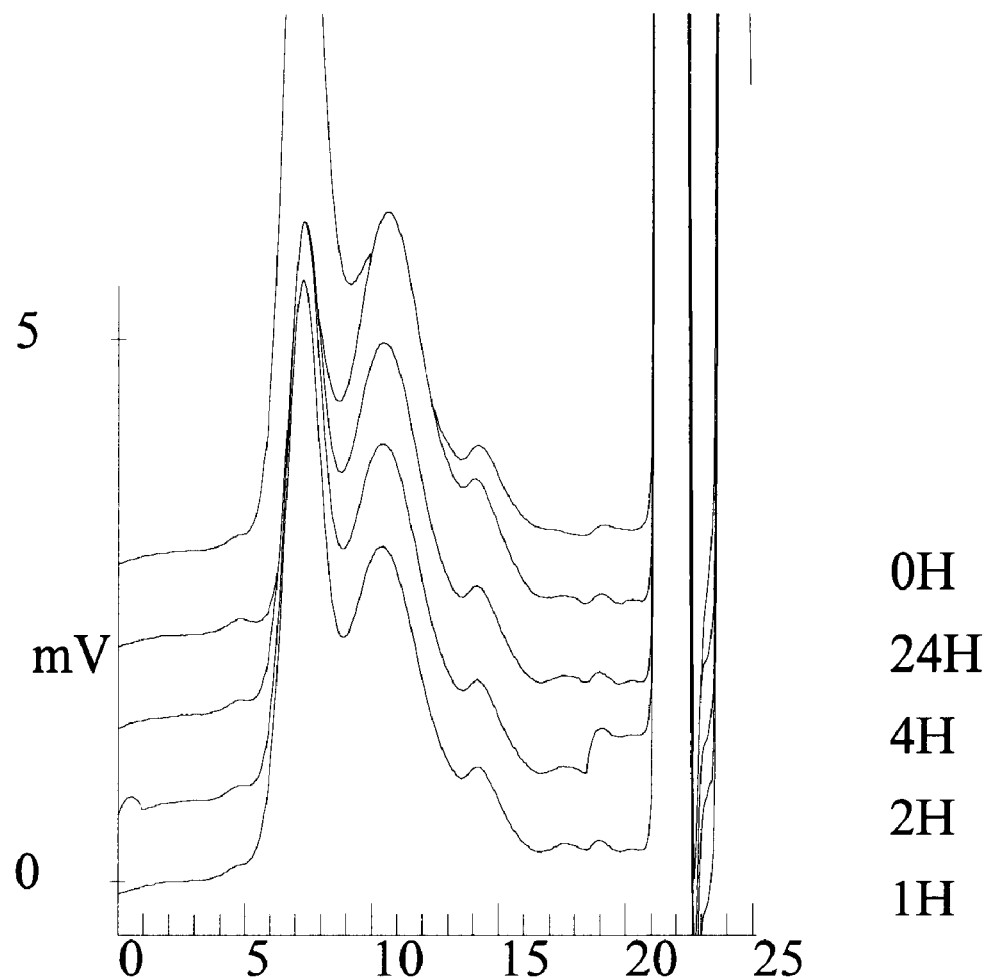
FIG. 13 shows high performance size exclusion chromatography (HPSEC) of RG-S degraded by the rhamnogalacturonan hydrolase from *Bacillus licheniformis* (BLR3).
Figure 14:
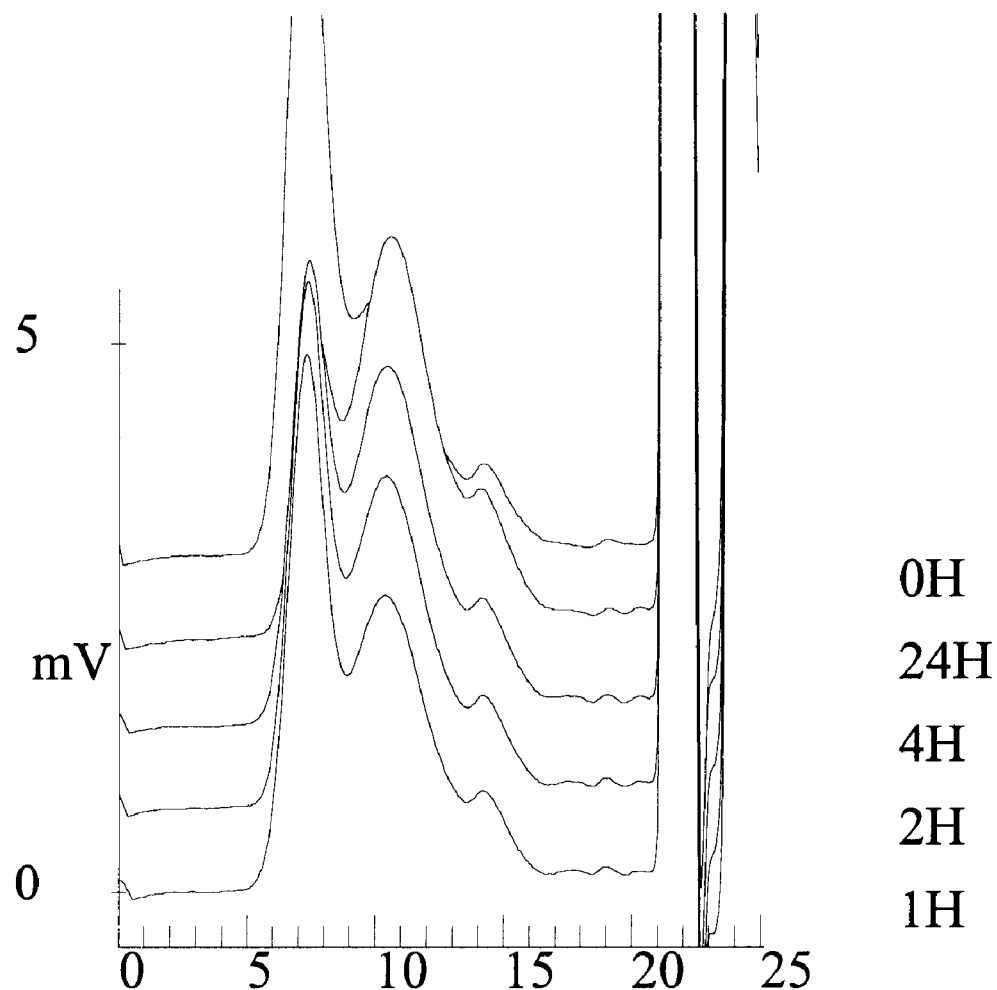
FIG. 14 shows high performance size exclusion chromatography (HPSEC) of RG-S degraded by the rhamnogalacturonan hydrolase from *Bacillus halodurans* KJS9 (BXA15).

RG and RG-S were both degraded by the enzymes BXR1, BLR3 and BXA15 and to the same extent (FIGS. 9, 10, 11, 12, 13, 14). These substrates were not depolymerized as much as the MHR-S substrate, probably, because the RG substrate has a high content of xylose and arabinose.

EXAMPLE 7
Determination of Hydrolase vs Lyase Activity
Determination of Enzyme Activity By Measuring Reducing Ends The assay was carried out in a solution of 0.5% saponified hairy regions from apples (MHR-S) in 100 mM Tris buffer pH 8. Enzymes, purified as described in Example 2 and 5, respectively, were dosed as follow:

|  | Enzyme conc. in assay |
| --- | --- |
| *B. subtilis* (BSR5) | 0.24 mg/ml |
| *B. halodurans* KJ59 (BXA15) | 0.02 mg/ml |

The assay mix was incubated at 40° C. for 15 minutes followed by a 10 fold dilution before determination of reducing sugars by the PHBAH method (Lever, M. 1972, A new reaction for colormetric determination of carbohydrates. Anal. Biochem. 47:273–279). Substrate without addition of enzyme was used as control in this experiment. Galacturonic acid was used as standard.

The following data were obtained and show that new reducing ends were formed by action of the enzymes:

|  | $OD_{410}$ |
| --- | --- |
| Control | 0.94 |
| BSR5 | 2.1 |
| BXA15 | 1.7 |

Lyase Assay

Cleavage of rhamnogalacturonan by a lyase, i.e. by beta-elimination, generates a new reducing end and a new non-reducing end with a double bond between C-4 and C-5 of the sugar residue. This double bond gives a characteristic absorption maximum at 235 nm, the extinction coefficient is 5.5 $mM^{-1} \times cm^{-1}$ (Albersheim, P. 1966, Methods in Enzymology, vol 8 p. 628).

For determination of beta-elimination an assay measuring the increase in absorbency at 235 nm was carried out using a solution of 0.1% saponified hairy regions from apples (MHR-S) in 50 mM Tris buffer pH 8. Enzymes, purified as described in Example 2 and 5, respectively, were dosed as follow:

|  | Enzyme konc. in assay |
| --- | --- |
| *B. subtilis* (BSR5) | 0.047 mg/ml |
| *B. halodurans* KJ59 (BXA15) | 0.004 mg/ml |

The assay was performed using a 0.5 ml cuvette with a 1 cm light path on a HP diode array spectrophotometer in a temperature controlled cuvette holder with continuous measurement of the absorbency at 235 nm. The temperature was 40° C. and absorbency was followed for 15 minutes. Substrate without addition of enzyme was used as control in this experiment.

The following data were obtained showing that the enzymes have no lyase activity:

|  | Increase in $OD_{235}$ (15 min.) |
| --- | --- |
| Control | 0.4 |
| BSR5 | 0.4 |
| BXA15 | 0.4 |

Conclusion

The enzymes BSR5 (*B. subtilis*) and BXA15 (*B. halodurans* KJ59) are both hydrolases.

LITERATURE

Lever, M. (1972) A new reaction for colormetric determination of carbohydrates. Anal. Biochem. 47, 273–279.

N. C. Carpita and D. M. Gibeaut (1993) The Plant Journal 3:1–30.

Devereux, J., Haeberli, P., and Smithies, O. (1984) Nucleic Acids Res. 12, 387–395.

Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol. 172:4315–4321.

Dretzen, G., Bellard, M., Sassone-Corsi, P., Chambon, P. (1981) A reliable method for the recovery of DNA fragments from agarose and acrylamide gels. Anal. Biochem., 112, 295–298.

Kauppinen et al (1995) J. Biol. Chem. 270:27172–27178.

Kofod et al (1994) J. Biol. Chem. 269:29182–29189.

Pitcher, D. G., Saunders, N. A., Owen, R. J. (1989). Rapid extraction of bacterial genomic DNA with guanidium thiocyanate. Lett. Appl. Microbiol., 8, 151–156.

Schols, H. A. et al (1990) Carbohydr. Res. 206:117–129.

What is claimed is:

1. An isolated enzyme exhibiting rhamnogalacturonan hydrolase activity, said enzyme comprising a polypeptide comprising an amino acid sequence which is at least 80% homologous to the amino add sequence shown in SEQ ID NO:4.

2. The isolated enzyme of claim 1, wherein said enzyme comprises a polypeptide comprising an amino acid sequence which is at least 85% homologous to the amino acid sequence shown in SEQ ID NO:4.

3. The isolated enzyme of claim 1, wherein said enzyme comprises a polypeptide comprising an amino acid sequence which is at least 90% homologous to the amino acid sequence shown in SEQ ID NO:4.

4. The isolated enzyme of claim 1, wherein said enzyme comprises a polypeptide comprising an amino acid sequence which is at least 95% homologous to the amino acid sequence shown in SEQ ID NO:4.

5. The isolated enzyme of claim 1, wherein said enzyme comprises a polypeptide comprising an amino acid sequence which is at least 98% homologous to the amino acid sequence shown in SEQ ID NO:4.

6. The isolated enzyme of claim 1, wherein said enzyme comprises the amino acid sequence shown in SEQ ID NO:4.

7. An animal feed composition, said animal feed composition comprising plant material rich in pectic substance and the enzyme of any one of claims 1–6.

8. A detergent composition, said detergent composition comprising the enzyme of any one of claims 1–6 and a surfactant.

9. An animal feed composition, said animal feed composition comprising plant material rich in pectic substance and an isolated enzyme exhibiting rhamnogalacturonan hydrolase activity, said enzyme comprising a polypeptide comprising an amino acid sequence which is at least 76% homologous to the amino acid sequence shown in SEQ ID NO:4.

10. A detergent composition, said detergent composition comprising a surfactant and an isolated enzyme exhibiting rhamnogalacturonan hydrolase activity, said enzyme comprising a polypeptide comprising an amino acid sequence which is at least 75% homologous to the amino acid sequence shown in SEQ ID NO:4.

* * * * *

SEQUENCE LISTING

```
<160> NUMBER OF SEQ ID NOS: 61

<210> SEQ ID NO 1
<211> LENGTH: 1863
<212> TYPE: DNA
<213> ORGANISM: Bacillus sp. AA 386

<400> SEQUENCE: 1
atgtttagta agcggttaca tcatttctgg cgagtgatgc tggggctggt t gttgttgta      60 tccacgatcg ggtcggtgtt tctcccggtg tccacagcgt cggctgcacc c agacaggcg     120 gagaacatta gccgcggcct ggtagcggtg aaggtaagca gcggcgtgtt c atcagctgg     180 cggctgcttg ggacggagca gctctcgact tccttcaatg tatatcggaa c ggaactaaa     240 gtgaacgccg ccccgattac gaacagcacg aacctgctgg atactgcggg c acgacttct     300 tccacttata cggtccgggc cgtcgtcggc ggcgtggagc agccggcctc c cccgccgtc     360 cgcgtgtggg caaacaacta cctggatgtc ccgatccagg cgcctcccgg g gggagaaca     420 ccggatgggg tgaactatac ctacagcgcc aatgatgcca gcatcggaga c ctagatggc     480 gatggggaat acgagatcgt gctcaaatgg gaccctacga actccaagga c aattcccaa     540 ggcggctata cgggcaatgt ttacctggat gcctacaagc ttaatggcac g cggctgtgg     600 cgaatcgacc tgggtcgaaa cattcgggcc ggcgcgcatt acacacagtt t ctcgtttat     660 gattttgacg gagacgggaa ggcggagatc gtctgcaaga cggcggacgg c accgttgac     720 ggcacgggca tcaccatcgg caatgccaat gccgatcatc gcaacgcgaa t ggttatgtg     780 ctctccgggc ccgagttcct taccgtcttc tccggtcaga caggcaaagc c ttaacgacc     840 atcgactatg ttccgccaag aggaaatgta tccagttggg gcgacaatta c ggcaaccgt     900 gtggaccgct tcctggccgg agtagcttat cttgatggcg tccaccccag c atcattatg     960 gcacgcgggt attatacccg gaccgttgtt gttgcctatg actggaatgg c cgcgcactg    1020 acccgaagat ggacatttga cagcaacagc tccaccaatc ccggaacagc c ggacaaggc    1080 aaccacagct taagcgtcgc cgatgtcgac ggggatggca aggacgaaat c atctacggc    1140 gctctgacca tcaacgacaa cggggccaca ctgtacaaca ccagactcgg g catggcgat    1200 gcgctgcatg taggagattt caatccaaac cggcctggac ttgaagtatt c aaagttatg    1260 gaggatgcca atgcaccttg cggtgctgct gtatgggatg ccgctaccgg g cagattctg    1320 tgggggtgc gtaccggcag ggacaccggc cggggtatgg ccgcggatat t gacccgaac    1380 catccagggg tagaggtatg ggccagcggc ggcgtcgggc tgtattccat t acaggcacc    1440 aaaatcagca ataacgcc ttcgataaac tttggcatct ggtgggacgg c gatctgtcc    1500 cgagagctgc tggacgatat tcggatcgac aagtggaatt acaacaacaa c accatgtac    1560
```

-continued

```
aatctgctaa ccggctctgg cgtcgcctcc aacaatggca ccaaagccac g ccaacgctg      1620 caggccgatc tgatcggcga ttggcgcgag gaggtcatct ggagaaaatc c gacaacacc      1680 gcgcttcgca tctacacaac taccgatctg accaatcata agatatacac g ctgatgcat     1740 gatccggtat accggctgag catcgcctgg cagaacgtcg cctacaacca g cctcctcat     1800 acaggcttct tcctggggag cggtatgggg ccggttacga aaccggatat c tatgtcgtt     1860 cca                                                                     1863
```

<210> SEQ ID NO 2
<211> LENGTH: 621
<212> TYPE: PRT
<213> ORGANISM: Bacillus sp. AA 386

<400> SEQUENCE: 2

```
Met Phe Ser Lys Arg Leu His His Phe Trp Arg Val Met Leu Gly Leu
  1               5                  10                  15

Val Val Val Ser Thr Ile Gly Ser Val Phe Leu Pro Val Ser Thr
             20                  25                  30

Ala Ser Ala Ala Pro Arg Gln Ala Glu Asn Ile Ser Arg Gly Leu Val
         35                  40                  45

Ala Val Lys Val Ser Ser Gly Val Phe Ile Ser Trp Arg Leu Leu Gly
     50                  55                  60

Thr Glu Gln Leu Ser Thr Ser Phe Asn Val Tyr Arg Asn Gly Thr Lys
 65                  70                  75                  80

Val Asn Ala Ala Pro Ile Thr Asn Ser Thr Asn Leu Leu Asp Thr Ala
                 85                  90                  95

Gly Thr Thr Ser Ser Thr Tyr Thr Val Arg Ala Val Val Gly Gly Val
            100                 105                 110

Glu Gln Pro Ala Ser Pro Ala Val Arg Val Trp Ala Asn Asn Tyr Leu
        115                 120                 125

Asp Val Pro Ile Gln Ala Pro Pro Gly Gly Arg Thr Pro Asp Gly Val
    130                 135                 140

Asn Tyr Thr Tyr Ser Ala Asn Asp Ala Ser Ile Gly Asp Leu Asp Gly
145                 150                 155                 160

Asp Gly Glu Tyr Glu Ile Val Leu Lys Trp Asp Pro Thr Asn Ser Lys
                165                 170                 175

Asp Asn Ser Gln Gly Gly Tyr Thr Gly Asn Val Tyr Leu Asp Ala Tyr
            180                 185                 190

Lys Leu Asn Gly Thr Arg Leu Trp Arg Ile Asp Leu Gly Arg Asn Ile
        195                 200                 205

Arg Ala Gly Ala His Tyr Thr Gln Phe Leu Val Tyr Asp Phe Asp Gly
    210                 215                 220

Asp Gly Lys Ala Glu Ile Val Cys Lys Thr Ala Asp Gly Thr Val Asp
225                 230                 235                 240

Gly Thr Gly Ile Thr Ile Gly Asn Ala Asn Ala Asp His Arg Asn Ala
                245                 250                 255

Asn Gly Tyr Val Leu Ser Gly Pro Glu Phe Leu Thr Val Phe Ser Gly
            260                 265                 270

Gln Thr Gly Lys Ala Leu Thr Thr Ile Asp Tyr Val Pro Pro Arg Gly
        275                 280                 285

Asn Val Ser Ser Trp Gly Asp Asn Tyr Gly Asn Arg Val Asp Arg Phe
    290                 295                 300

Leu Ala Gly Val Ala Tyr Leu Asp Gly Val His Pro Ser Ile Ile Met
305                 310                 315                 320
```

Ala Arg Gly Tyr Tyr Thr Arg Thr Val Val Ala Tyr Asp Trp Asn
                325                 330                 335

Gly Arg Ala Leu Thr Arg Arg Trp Thr Phe Asp Ser Asn Ser Ser Thr
            340                 345                 350

Asn Pro Gly Thr Ala Gly Gln Gly Asn His Ser Leu Ser Val Ala Asp
            355                 360                 365

Val Asp Gly Asp Gly Lys Asp Glu Ile Ile Tyr Gly Ala Leu Thr Ile
    370                 375                 380

Asn Asp Asn Gly Ala Thr Leu Tyr Asn Thr Arg Leu Gly His Gly Asp
385                 390                 395                 400

Ala Leu His Val Gly Asp Phe Asn Pro Asn Arg Pro Gly Leu Glu Val
                405                 410                 415

Phe Lys Val Met Glu Asp Ala Asn Ala Pro Tyr Gly Ala Ala Val Trp
            420                 425                 430

Asp Ala Thr Gly Gln Ile Leu Trp Gly Val Arg Thr Gly Arg Asp
        435                 440                 445

Thr Gly Arg Gly Met Ala Ala Asp Ile Asp Pro Asn His Pro Gly Val
    450                 455                 460

Glu Val Trp Ala Ser Gly Gly Val Gly Leu Tyr Ser Ile Thr Gly Thr
465                 470                 475                 480

Lys Ile Ser Asn Asn Thr Pro Ser Ile Asn Phe Gly Ile Trp Trp Asp
                485                 490                 495

Gly Asp Leu Ser Arg Glu Leu Leu Asp Asp Ile Arg Ile Asp Lys Trp
            500                 505                 510

Asn Tyr Asn Asn Asn Thr Met Tyr Asn Leu Leu Thr Gly Ser Gly Val
        515                 520                 525

Ala Ser Asn Asn Gly Thr Lys Ala Thr Pro Thr Leu Gln Ala Asp Leu
    530                 535                 540

Ile Gly Asp Trp Arg Glu Glu Val Ile Trp Arg Lys Ser Asp Asn Thr
545                 550                 555                 560

Ala Leu Arg Ile Tyr Thr Thr Thr Asp Leu Thr Asn His Lys Ile Tyr
                565                 570                 575

Thr Leu Met His Asp Pro Val Tyr Arg Leu Ser Ile Ala Trp Gln Asn
            580                 585                 590

Val Ala Tyr Asn Gln Pro Pro His Thr Gly Phe Phe Leu Gly Ser Gly
        595                 600                 605

Met Gly Pro Val Thr Lys Pro Asp Ile Tyr Val Val Pro
    610                 615                 620

<210> SEQ ID NO 3
<211> LENGTH: 1869
<212> TYPE: DNA
<213> ORGANISM: Bacillus licheniformis

<400> SEQUENCE: 3
atgaaaaaag gaaagaaaag gtggaagaac ctgttggccg cgtcatctct t ttattaatc    60 acgctagtga ccggcttctc ggagcaagct gaggcagacg ggcggacggc t gcgcaggca   120 aggcaaatgg aatcgcttaa caggggggctt gtcgctgtta aaacggggaa c ggtgtcttt   180 gtcagctggc ggcttctggg aaccgaaccg tcttctgttt cacttaatgt g tatcgaaac   240 ggaaagaagc tgaacggttc tccgattaca tcgagcacaa actatcagga t gcaggcggg   300 gatttgaacg ccgtttacca ggtgcgcgcc gttttgaacg gcagggagca g gctccttct   360 gaatccgtcg gcgtattgaa taaacaatat aaatctgttc cgctgcaaaa a ccggccgga   420

-continued

```
ggaaaaacgc tgatggggt gtcatacaca tacagcgcca atgatgcgag c ttaggcgac    480
cttgttggag acgcccaata tgaaatcttt ctcaagtggg atccttccaa t tcaaaggat    540
aattcacagg acgatacac gggagatgtg ctgattgacg catacaagct t gacggcacc    600
atgatgtgga gaatcaacct tggcaaaaat attcgcgccg cgcccatta t acgcagttt    660
ctcgtctatg actttgacgg cgatggaaaa gcggaaatcg ccatgaagac g gcagacggg    720
acgaaggacg gcaaagggaa ggtgatcggc aatgcaaacg ccgattaccg c aatgcccaa    780
ggccgaattt tgtcagggcc tgagtatttg acggttttta aggcgatac a ggcgctgag    840
cttacaacgg tcaactacga acctgcccgg ggaaatgtag ccgattgggg a gacagctac    900
ggcaacaggg ttgaccgctt tctggccggt gtcgcatacc ttgacgggga g cggccgagt    960
tttgtcatgg cacgcggtta ttacacgaga acagtgctag tcgcttacaa c ttcagaggc   1020
ggaaagctga ccaagctgtg gacgttcgat tcggatgctc ccggaaatgg c gcctatgcc   1080
ggtcaaggca ccacagttt gagcgtcgcc gacgttgacg gagatggaaa g gacgagatc   1140
atatacggag cgatggctgt cgatcatgac ggaaaaggcc tctactcaac c ggctgggga   1200
catggggatg ccatgcatac agggaacctg gacccgtcaa ggcctggact g gaagtcttc   1260
caagtccatg aaaacagcaa ttctccttat ggcttgtcct ccgcgatgc g aaaacagga   1320
aagatcatct ggggagttca cgcaggtaaa gatgtcggac gcggaatggc c gctgatatc   1380
gatccgcgct acgaaggagc ggaagtatgg gcgaacggca gtctttatac g gcaaaaggc   1440
gtaaaaatcg gaaacacatt gccttcatca acgaacttcg gcatctggtg g gacggcgat   1500
ctccaaagag agcttctgga cagcaacaga attgataaat gggattatca a aattcgcga   1560
accgtcaact tgctgacagc gtccggagct tcggcaaata acggaacaaa a gcgacgccg   1620
tccctgcagg cggacattct cggagactgg cgcgaagaag tggtctggcg a gcggaggac   1680
agcagcgaac tgcgcatcta cacgacgaca gacgtgacgg agcaccgcat g tatacgctg   1740
atgcatgatg cagtctatcg cctcggtatc gcctggcaga atgtcggcta c aaccagcct   1800
ccgcacaccg gcttttattt aggcgaaggc atgcagacac cggagaagcc g aacatttat   1860
acacgctga                                                            1869
```

<210> SEQ ID NO 4
<211> LENGTH: 622
<212> TYPE: PRT
<213> ORGANISM: Bacillus licheniformis

<400> SEQUENCE: 4

```
Met Lys Lys Gly Lys Lys Arg Trp Lys Asn L eu Leu Ala Ala Ser Ser
 1               5                  10                   15

Leu Leu Leu Ile Thr Leu Val Thr Gly Phe S er Glu Gln Ala Glu Ala
             20                  25                   30

Asp Gly Arg Thr Ala Ala Gln Ala Arg Gln M et Glu Ser Leu Asn Arg
         35                  40                   45

Gly Leu Val Ala Val Lys Thr Gly Asn Gly V al Phe Val Ser Trp Arg
     50                  55                   60

Leu Leu Gly Thr Glu Pro Ser Ser Val Ser L eu Asn Val Tyr Arg Asn
65                  70                  75                   80

Gly Lys Lys Leu Asn Gly Ser Pro Ile Thr S er Ser Thr Asn Tyr Gln
                 85                  90                   95

Asp Ala Gly Gly Asp Leu Asn Ala Val Tyr G ln Val Arg Ala Val Leu
            100                 105                  110
```

```
Asn Gly Arg Glu Gln Ala Pro Ser Glu Ser Val Gly Val Leu Asn Lys
            115                 120                 125
Gln Tyr Lys Ser Val Pro Leu Gln Lys Pro Ala Gly Gly Lys Thr Pro
        130                 135                 140
Asp Gly Val Ser Tyr Thr Tyr Ser Ala Asn Asp Ala Ser Leu Gly Asp
145                 150                 155                 160
Leu Val Gly Asp Ala Gln Tyr Glu Ile Phe Leu Lys Trp Asp Pro Ser
                165                 170                 175
Asn Ser Lys Asp Asn Ser Gln Asp Gly Tyr Thr Gly Asp Val Leu Ile
            180                 185                 190
Asp Ala Tyr Lys Leu Asp Gly Thr Met Met Trp Arg Ile Asn Leu Gly
        195                 200                 205
Lys Asn Ile Arg Ala Gly Ala His Tyr Thr Gln Phe Leu Val Tyr Asp
210                 215                 220
Phe Asp Gly Asp Gly Lys Ala Glu Ile Ala Met Lys Thr Ala Asp Gly
225                 230                 235                 240
Thr Lys Asp Gly Lys Gly Lys Val Ile Gly Asn Ala Asn Ala Asp Tyr
                245                 250                 255
Arg Asn Ala Gln Gly Arg Ile Leu Ser Gly Pro Glu Tyr Leu Thr Val
            260                 265                 270
Phe Lys Gly Asp Thr Gly Ala Glu Leu Thr Thr Val Asn Tyr Glu Pro
        275                 280                 285
Ala Arg Gly Asn Val Ala Asp Trp Gly Asp Ser Tyr Gly Asn Arg Val
        290                 295                 300
Asp Arg Phe Leu Ala Gly Val Ala Tyr Leu Asp Gly Glu Arg Pro Ser
305                 310                 315                 320
Phe Val Met Ala Arg Gly Tyr Tyr Thr Arg Thr Val Leu Val Ala Tyr
                325                 330                 335
Asn Phe Arg Gly Gly Lys Leu Thr Lys Leu Trp Thr Phe Asp Ser Asp
            340                 345                 350
Ala Pro Gly Asn Gly Ala Tyr Ala Gly Gln Gly Asn His Ser Leu Ser
        355                 360                 365
Val Ala Asp Val Asp Gly Asp Gly Lys Asp Glu Ile Ile Tyr Gly Ala
        370                 375                 380
Met Ala Val Asp His Asp Gly Lys Gly Leu Tyr Ser Thr Gly Trp Gly
385                 390                 395                 400
His Gly Asp Ala Met His Thr Gly Asn Leu Asp Pro Ser Arg Pro Gly
                405                 410                 415
Leu Glu Val Phe Gln Val His Glu Asn Ser Asn Ser Pro Tyr Gly Leu
            420                 425                 430
Ser Phe Arg Asp Ala Lys Thr Gly Lys Ile Ile Trp Gly Val His Ala
        435                 440                 445
Gly Lys Asp Val Gly Arg Gly Met Ala Ala Asp Ile Asp Pro Arg Tyr
        450                 455                 460
Glu Gly Ala Glu Val Trp Ala Asn Gly Ser Leu Tyr Thr Ala Lys Gly
465                 470                 475                 480
Val Lys Ile Gly Asn Thr Leu Pro Ser Ser Thr Asn Phe Gly Ile Trp
                485                 490                 495
Trp Asp Gly Asp Leu Gln Arg Glu Leu Leu Asp Ser Asn Arg Ile Asp
            500                 505                 510
Lys Trp Asp Tyr Gln Asn Ser Arg Thr Val Asn Leu Leu Thr Ala Ser
        515                 520                 525
```

```
Gly Ala Ser Ala Asn Asn Gly Thr Lys Ala T hr Pro Ser Leu Gln Ala
    530                 535             540

Asp Ile Leu Gly Asp Trp Arg Glu Val V al Trp Arg Ala Glu Asp
545                 550             555                 560

Ser Ser Glu Leu Arg Ile Tyr Thr Thr Thr A sp Val Thr Glu His Arg
                565             570                 575

Met Tyr Thr Leu Met His Asp Ala Val Tyr A rg Leu Gly Ile Ala Trp
                580             585                 590

Gln Asn Val Gly Tyr Asn Gln Pro Pro His T hr Gly Phe Tyr Leu Gly
            595             600             605

Glu Gly Met Gln Thr Pro Glu Lys Pro Asn I le Tyr Thr Arg
    610                 615             620

<210> SEQ ID NO 5
<211> LENGTH: 1863
<212> TYPE: DNA
<213> ORGANISM: Bacillus subtilis

<400> SEQUENCE: 5
```

| | | | | | |
|---|---|---|---|---|---|
| atgagaagga | gctgtctgat | gattagacga | aggaaacgca | tgtttaccgc t | gttacgttg | 60 |
| ctggtcttgt | tggtgatggg | aacctctgta | tgtcctgtga | agctgaagg g | gcagcgcgg | 120 |
| cagatggaag | cgctgaaccg | ggggcttgta | gcggtcaaga | cggacggggg c | attttttgtc | 180 |
| agctggcggt | tcttggaaac | cgaaaacgca | tctgttttgt | tcaatgtgta c | agagacggg | 240 |
| caaaaactga | atgctgcgcc | tgtcaaaaca | acgaactatg | tggataaaaa c | ggttcggcg | 300 |
| ggctcaacgt | atacggttcg | gctgttgta | aacggtaccg | aacagccggc t | tctgaaaaa | 360 |
| gcctccgtat | gggcgcagcc | gtatcattcc | gtcccgctgg | ataaaccggc t | gcggcacg | 420 |
| acgccaaagg | gtgaatctta | cacgtacagc | gctaatgacg | caagtgttgg c | gatgtggat | 480 |
| ggtgacgggc | aatacgagct | gatcctgaaa | tgggacccgt | ccaactcaaa a | gacaattca | 540 |
| caggatggct | atacgggtga | cgtgctgatt | gacgcgtata | aactggacgg c | acaaagtta | 600 |
| tggcggatca | atctcggcaa | aaacatcaga | gcgggcgcgc | actacaccca g | tttatggtg | 660 |
| tatgaccttg | atggtgacgg | aaaagcagaa | gtggcaatga | aacggcaga c | gggacaaaa | 720 |
| gacggcacgg | gcaaagtaat | tggaaatgcc | aatgcagatt | acagaaatga a | cagggcgt | 780 |
| gtgctttcag | gccctgaata | tctcactgtg | tttcaaggtt | caaccgggaa a | gagcttgtc | 840 |
| accgcaaatt | ttgaaccggc | gcgcggcaat | gtgtcggatt | ggggagacag c | tacggcaac | 900 |
| cgtgttgacc | gttttctcgc | cggcattgcc | taccttgatg | gacagcggcc g | agcctgatc | 960 |
| atgaccagag | gtattacgc | taaaaccatg | ctagttgcct | ataacttcag g | gacggaaag | 1020 |
| ctgtcaaagc | tttggacgct | ggactcctca | agtcaggaa | atgaagcgtt t | gccggacag | 1080 |
| gggaatcaca | acctgagcat | cgcggacgtt | gacggggatg | gaaaagatga g | gattatttc | 1140 |
| ggctcaatgg | ctgttgatca | tgacgggaaa | ggcatgtact | cgaccggctt a | ggccatggg | 1200 |
| gatgccctcc | atacaggaga | tcttgatccg | ggccggccgg | ggcttgaggt g | tttcaagtt | 1260 |
| catgaggaca | aaaatgcaaa | atacggctta | tctttccggg | atgctgcaac t | ggaaaaatc | 1320 |
| ctttggggcg | tttatgccgg | caaggatgta | ggccggggaa | tggctgctga t | attgacccg | 1380 |
| cgttatccgg | acaggaggt | gtgggcaaac | ggttctctct | actcagcgaa a | ggggtcaaa | 1440 |
| atcggaagcg | gggttccgtc | ctcgaccaac | ttcggcatct | ggtgggacgg c | gatctgctc | 1500 |
| cgggaacagc | tggacagcaa | ccgaattgat | aagtgggatt | atcaaaacgg c | gtatcgaaa | 1560 |
| aatatgctga | ctgcatcagg | cgcagcggct | aacaacggca | caaaagcaac a | ccaacgctt | 1620 |

```
caggctgatc tgctcggtga ctggcgcgag gaagtggtgt ggagaacgga g gacagcagt   1680 gctctgcgca tttacacgac gaccattccg actgagcaca ggctgtatac g ctgatgcac   1740 gatccggtgt accggcttgg catcgcctgg caaaatatcg cctataacca g ccgccgcac   1800 acaagcttct ttttaggaga cggcatggcg gaacagccaa accaaatat g tatacgcct    1860 taa                                                                  1863
```

<210> SEQ ID NO 6
<211> LENGTH: 620
<212> TYPE: PRT
<213> ORGANISM: Bacillus subtilis

<400> SEQUENCE: 6

```
Met Arg Arg Ser Cys Leu Met Ile Arg Arg A rg Lys Arg Met Phe Thr
 1               5                  10                  15

Ala Val Thr Leu Leu Val Leu Val Met G ly Thr Ser Val Cys Pro
            20                  25                  30

Val Lys Ala Glu Gly Ala Ala Arg Gln Met G lu Ala Leu Asn Arg Gly
        35                  40                  45

Leu Val Ala Val Lys Thr Asp Gly Gly Ile P he Val Ser Trp Arg Phe
    50                  55                  60

Leu Gly Thr Glu Asn Ala Ser Val Leu Phe A sn Val Tyr Arg Asp Gly
65                  70                  75                  80

Gln Lys Leu Asn Ala Ala Pro Val Lys Thr T hr Asn Tyr Val Asp Lys
                85                  90                  95

Asn Gly Ser Ala Gly Ser Thr Tyr Thr Val A rg Ala Val Asn Gly
            100                 105                 110

Thr Glu Gln Pro Ala Ser Glu Lys Ala Ser V al Trp Ala Gln Pro Tyr
        115                 120                 125

His Ser Val Pro Leu Asp Lys Pro Ala Gly G ly Thr Pro Lys Gly
    130                 135                 140

Glu Ser Tyr Thr Tyr Ser Ala Asn Asp Ala S er Val Gly Asp Val Asp
145                 150                 155                 160

Gly Asp Gly Gln Tyr Glu Leu Ile Leu Lys T rp Asp Pro Ser Asn Ser
                165                 170                 175

Lys Asp Asn Ser Gln Asp Gly Tyr Thr Gly A sp Val Leu Ile Asp Ala
            180                 185                 190

Tyr Lys Leu Asp Gly Thr Lys Leu Trp Arg I le Asn Leu Gly Lys Asn
        195                 200                 205

Ile Arg Ala Gly Ala His Tyr Thr Gln Phe M et Val Tyr Asp Leu Asp
    210                 215                 220

Gly Asp Gly Lys Ala Glu Val Ala Met Lys T hr Ala Asp Gly Thr Lys
225                 230                 235                 240

Asp Gly Thr Gly Lys Val Ile Gly Asn Ala A sn Ala Asp Tyr Arg Asn
                245                 250                 255

Glu Gln Gly Arg Val Leu Ser Gly Pro Glu T yr Leu Thr Val Phe Gln
            260                 265                 270

Gly Ser Thr Gly Lys Glu Leu Val Thr Ala A sn Phe Glu Pro Ala Arg
        275                 280                 285

Gly Asn Val Ser Asp Trp Gly Asp Ser Tyr G ly Asn Arg Val Asp Arg
    290                 295                 300

Phe Leu Ala Gly Ile Ala Tyr Leu Asp Gly G ln Arg Pro Ser Leu Ile
305                 310                 315                 320
```

```
Met Thr Arg Gly Tyr Tyr Ala Lys Thr Met Leu Val Ala Tyr Asn Phe
                325                 330                 335
Arg Asp Gly Lys Leu Ser Lys Leu Trp Thr Leu Asp Ser Ser Lys Ser
            340                 345                 350
Gly Asn Glu Ala Phe Ala Gly Gln Gly Asn His Asn Leu Ser Ile Ala
        355                 360                 365
Asp Val Asp Gly Asp Gly Lys Asp Glu Ile Ile Phe Gly Ser Met Ala
    370                 375                 380
Val Asp His Asp Gly Lys Gly Met Tyr Ser Thr Gly Leu Gly His Gly
385                 390                 395                 400
Asp Ala Leu His Thr Gly Asp Leu Asp Pro Gly Arg Pro Gly Leu Glu
                405                 410                 415
Val Phe Gln Val His Glu Asp Lys Asn Ala Lys Tyr Gly Leu Ser Phe
            420                 425                 430
Arg Asp Ala Ala Thr Gly Lys Ile Leu Trp Gly Val Tyr Ala Gly Lys
        435                 440                 445
Asp Val Gly Arg Gly Met Ala Ala Asp Ile Asp Pro Arg Tyr Pro Gly
    450                 455                 460
Gln Glu Val Trp Ala Asn Gly Ser Leu Tyr Ser Ala Lys Gly Val Lys
465                 470                 475                 480
Ile Gly Ser Gly Val Pro Ser Ser Thr Asn Phe Gly Ile Trp Trp Asp
                485                 490                 495
Gly Asp Leu Leu Arg Glu Gln Leu Asp Ser Asn Arg Ile Asp Lys Trp
            500                 505                 510
Asp Tyr Gln Asn Gly Val Ser Lys Asn Met Leu Thr Ala Ser Gly Ala
        515                 520                 525
Ala Ala Asn Asn Gly Thr Lys Ala Thr Pro Thr Leu Gln Ala Asp Leu
    530                 535                 540
Leu Gly Asp Trp Arg Glu Glu Val Val Trp Arg Thr Glu Asp Ser Ser
545                 550                 555                 560
Ala Leu Arg Ile Tyr Thr Thr Thr Ile Pro Thr Glu His Arg Leu Tyr
                565                 570                 575
Thr Leu Met His Asp Pro Val Tyr Arg Leu Gly Ile Ala Trp Gln Asn
            580                 585                 590
Ile Ala Tyr Asn Gln Pro Pro His Thr Ser Phe Phe Leu Gly Asp Gly
        595                 600                 605
Met Ala Glu Gln Pro Lys Pro Asn Met Tyr Thr Pro
    610                 615                 620

<210> SEQ ID NO 7
<211> LENGTH: 1413
<212> TYPE: DNA
<213> ORGANISM: Sorangium cellulosum

<400> SEQUENCE: 7
ctggacggcg acgggcggta cgagatcatc gtcaagtggg acccgtcgaa c ctcaaggac      60 aactcgcagg ctggccgcac cggcaagacg tacctcgacg cctactcgct c gagggcgag     120 cggctctggc gcatcgacct cggcgtgaac atccgggccg agcgcacta c tcgccgttc     180 ctcgtctacg atctcgacgg cgacgggaag gcggaggtgg ccgtcaagac g gcgccgggg     240 acacgcgacg gcacgggcga gcccctcagc aagggccccg cggcgaacga c gacgacagc     300 cgggactacc gcaacaacga cggctacatc ctgaccggcc cggagtacct c accgtgttc     360 tccggggaga ccggcgccga gctcgcgacg accgacttcg tggtggggcg c ggcgacccg     420
```

-continued

```
tgcagctggg gcaacaacga gtgttacggc aatcgcgtcg accgcttcgt c ggcacggtc      480 gcgttcctcg acgacaccgg tcgtccgagc gtggtgttcg ccgcggcta c tacgcgcgc      540 accacgctgt cggcgtggaa ctaccgcgac ggcgcgctca cgaacctctg g acgttcgac    600 tccagctcga gccgcgacaa cggggcgtac gccggcatgg cacccactc c atcagcgtc     660 gccaacgtgg atgacgatcc gcagcaggag atcatcaacg ggggcgccac g ttcgacaac    720 gacggcaagg gcctgtgcgc cgtggactac tacggtcacg gcgacgcgct g cacgtcacg    780 gatcacatcc tgtcgcgccc cggcctcgag gtgttccagc cgtacgaggg c ggggactca   840 cccgcctatg ccatgcgcga cgcgcgcacg tgcgaggtcc tctggcgggg g ccgggcaac   900 ggcggcgagg agggccccgg ccgcggcgtg cggccgacg tcgatccgcg c aacccgggc    960 agcgaggcgt gggtcaatag cagccagctc ctgagcggcg cggacggcga c gccatcggg  1020 aaccgccccg cgtcgtccaa cttcctcatc tggtgggacg cggatctgag c cgggagctg  1080 ctcgacggca acagcatccg ccaggccgac ggcgagggaa gcaacttcgc g gccgagggc  1140 tgcaccgcga caacggctc gaagagcaac ccgaccctca cgccgatat c ctcggcgac   1200 tggcgcgaag aggtgatctt ccgctgcggc agctcgattc gtatcttcac c acgaaccgc 1260 gtcgccacga gccggatcca caccctgatg cacgatccgc agtaccgcgt g gccatctcg 1320 tggcagaacg gcgcctacaa ccagccgcct cacccgagct ccacatcgg g gagggatg   1380 gcgccggtcc gaagccgga catccacgtc cgc                                 1413
```

<210> SEQ ID NO 8
<211> LENGTH: 471
<212> TYPE: PRT
<213> ORGANISM: Sorangium cellulosum

<400> SEQUENCE: 8

```
Leu Asp Gly Asp Gly Arg Tyr Glu Ile Ile V al Lys Trp Asp Pro Ser
 1               5                  10                  15

Asn Leu Lys Asp Asn Ser Gln Ala Gly Arg T hr Gly Lys Thr Tyr Leu
             20                  25                  30

Asp Ala Tyr Ser Leu Glu Gly Glu Arg Leu T rp Arg Ile Asp Leu Gly
         35                  40                  45

Val Asn Ile Arg Ala Gly Ala His Tyr Ser P ro Phe Leu Val Tyr Asp
     50                  55                  60

Leu Asp Gly Asp Gly Lys Ala Glu Val Ala V al Lys Thr Ala Pro Gly
 65                  70                  75                  80

Thr Arg Asp Gly Thr Gly Glu Pro Leu Ser L ys Gly Pro Ala Ala Asn
                 85                  90                  95

Asp Asp Asp Ser Arg Asp Tyr Arg Asn Asn A sp Gly Tyr Ile Leu Thr
            100                 105                 110

Gly Pro Glu Tyr Leu Thr Val Phe Ser Gly G lu Thr Gly Ala Glu Leu
        115                 120                 125

Ala Thr Thr Asp Phe Val Val Gly Arg Gly A sp Pro Cys Ser Trp Gly
    130                 135                 140

Asn Asn Glu Cys Tyr Gly Asn Arg Val Asp A rg Phe Val Gly Thr Val
145                 150                 155                 160

Ala Phe Leu Asp Asp Thr Gly Arg Pro Ser V al Val Phe Gly Arg Gly
                165                 170                 175

Tyr Tyr Ala Arg Thr Thr Leu Ser Ala Trp A sn Tyr Arg Asp Gly Ala
            180                 185                 190

Leu Thr Asn Leu Trp Thr Phe Asp Ser Ser S er Ser Arg Asp Asn Gly
```

```
                195                 200                 205
Ala Tyr Ala Gly Met Gly Thr His Ser Ile Ser Val Ala Asn Val Asp
    210                 215                 220

Asp Asp Pro Gln Gln Glu Ile Ile Asn Gly Gly Ala Thr Phe Asp Asn
225                 230                 235                 240

Asp Gly Lys Gly Leu Cys Ala Val Asp Tyr Tyr Gly His Gly Asp Ala
                245                 250                 255

Leu His Val Thr Asp His Ile Leu Ser Arg Pro Gly Leu Glu Val Phe
            260                 265                 270

Gln Pro Tyr Glu Gly Gly Asp Ser Pro Ala Tyr Ala Met Arg Asp Ala
        275                 280                 285

Arg Thr Cys Glu Val Leu Trp Arg Gly Gly Asn Gly Gly Glu Glu
    290                 295                 300

Gly Pro Gly Arg Gly Val Ala Ala Asp Val Asp Pro Arg Asn Pro Gly
305                 310                 315                 320

Ser Glu Ala Trp Val Asn Ser Ser Gln Leu Leu Ser Gly Ala Asp Gly
                325                 330                 335

Asp Ala Ile Gly Asn Arg Pro Ala Ser Ser Asn Phe Leu Ile Trp Trp
            340                 345                 350

Asp Ala Asp Leu Ser Arg Glu Leu Leu Asp Gly Asn Ser Ile Arg Gln
        355                 360                 365

Ala Asp Gly Glu Gly Ser Asn Phe Ala Ala Glu Gly Cys Thr Ala Asn
    370                 375                 380

Asn Gly Ser Lys Ser Asn Pro Thr Leu Ser Ala Asp Ile Leu Gly Asp
385                 390                 395                 400

Trp Arg Glu Glu Val Ile Phe Arg Cys Gly Ser Ser Ile Arg Ile Phe
                405                 410                 415

Thr Thr Asn Arg Val Ala Thr Ser Arg Ile His Thr Leu Met His Asp
            420                 425                 430

Pro Gln Tyr Arg Val Ala Ile Ser Trp Gln Asn Gly Ala Tyr Asn Gln
        435                 440                 445

Pro Pro His Pro Ser Phe His Ile Gly Glu Gly Met Ala Pro Val Pro
    450                 455                 460

Lys Pro Asp Ile His Val Arg
465                 470

<210> SEQ ID NO 9
<211> LENGTH: 512
<212> TYPE: DNA
<213> ORGANISM: Caldocellulosiruptor sp.

<400> SEQUENCE: 9
atgagaaaaa agaaaattta taggtcctgg ttgggtatag tggttattat tttgtgggtt      60
atatattgtg tatttaatcc gtataattta gcaataaaga atgttaaggg tgcagtttca     120
agtcaagttg agaagttaaa gaggggactg attgcaatta agttaataat ggtgtttat     180 cttacgtgga ggatgtttgg ttcagatcct gctgatattg gcttcaatat ataccgaaat     240
gggcaaaaaa taaaccaaat tcctattcaa gttagcacaa attatcttga tacaggaggg     300
aatactactt caaatacttc cattaggcca gttataaatg gccatgaaat agaaattca     360 gaagaagttt cagtcttacc taccaactat attgaaatta aattaaacag accacctacc     420
tcacctttgg gagcaatata ttctccgaat gacgcaagtg taggagattt agatggtgat     480
ggagaatacg aaatagtcct taaatgggat cc                                   512
```

<210> SEQ ID NO 10
<211> LENGTH: 170
<212> TYPE: PRT
<213> ORGANISM: Caldocellusiruptor sp.

<400> SEQUENCE: 10

Met Arg Lys Lys Ile Tyr Arg Ser Trp Leu Gly Ile Val Ile
1               5                   10                  15

Ile Leu Trp Val Ile Tyr Cys Val Phe Asn Pro Tyr Asn Leu Ala Ile
                20                  25                  30

Lys Asn Val Lys Gly Ala Val Ser Gln Val Glu Lys Leu Lys Arg
            35                  40                  45

Gly Leu Ile Ala Ile Lys Val Asn Asn Gly Val Tyr Leu Thr Trp Arg
    50                  55                  60

Met Phe Gly Ser Asp Pro Ala Asp Ile Gly Phe Asn Ile Tyr Arg Asn
65                  70                  75                  80

Gly Gln Lys Ile Asn Gln Ile Pro Ile Gln Val Ser Thr Asn Tyr Leu
                85                  90                  95

Asp Thr Gly Gly Asn Thr Thr Ser Lys Tyr Phe Ile Arg Pro Val Ile
            100                 105                 110

Asn Gly His Glu Ile Glu Asn Ser Glu Val Ser Val Leu Pro Thr
        115                 120                 125

Asn Tyr Ile Glu Ile Lys Leu Asn Arg Pro Pro Thr Ser Pro Leu Gly
    130                 135                 140

Ala Ile Tyr Ser Pro Asn Asp Ala Ser Val Gly Asp Leu Asp Gly Asp
145                 150                 155                 160

Gly Glu Tyr Glu Ile Val Leu Lys Trp Asp
                165                 170

<210> SEQ ID NO 11
<211> LENGTH: 336
<212> TYPE: DNA
<213> ORGANISM: Caldocellusiruptor sp.

<400> SEQUENCE: 11
gatcttacaa gagaattatt ggacaaaact aatatatata aatgggatta t aatactaac      60 tcatctaaaa ccatttttac agcaagtggg tgttcagcta ataatggtac g aaggcaact     120 ccatgtttga gtgcagatat attgggtgac tggcgcgagg aagttatatt c cgtacttct    180 gacaattcag ctattaggat atatatgact actatgcaga catcatacaa a attccaaca    240 ttgatgcata atcgtcaata cagagtgtca atagcatggc aaaacgtagc t tacaaccaa   300 ccgccccaca caaattttta ttttggagaa ggtatg                              336

<210> SEQ ID NO 12
<211> LENGTH: 112
<212> TYPE: PRT
<213> ORGANISM: Caldocellosiruptor sp.

<400> SEQUENCE: 12

Asp Leu Thr Arg Glu Leu Leu Asp Lys Thr Asn Ile Tyr Lys Trp Asp
1               5                   10                  15

Tyr Asn Thr Asn Ser Ser Lys Thr Ile Phe Thr Ala Ser Gly Cys Ser
                20                  25                  30

Ala Asn Asn Gly Thr Lys Ala Thr Pro Cys Leu Ser Ala Asp Ile Leu
            35                  40                  45

Gly Asp Trp Arg Glu Glu Val Ile Phe Arg Thr Ser Asp Asn Ser Ala

|   |   | 50 |   |   | 55 |   |   | 60 |   |
|---|---|---|---|---|---|---|---|---|---|

Ile Arg Ile Tyr Met Thr Thr Met Gln Thr S er Tyr Lys Ile Pro Thr
65                  70                  75                  80

Leu Met His Asn Arg Gln Tyr Arg Val Ser I le Ala Trp Gln Asn Val
                85                  90                  95

Ala Tyr Asn Gln Pro Pro His Thr Asn Phe T yr Phe Gly Glu Gly Met
            100                 105                 110

<210> SEQ ID NO 13
<211> LENGTH: 1965
<212> TYPE: DNA
<213> ORGANISM: Bacillus halodurans C4539

<400> SEQUENCE: 13

| atgcttaggc aaaaggagca gctagacaga gggcttgtcg ccgtaaaacg g cggatgga | 60 |
|---|---|
| gtgttttta a gctggcgtct actcgggacg gagcatccgc ttacggtctt t catgtgtac | 120 |
| cgtgatggag aaaaaatcac gaaagctggg ctgcaagaag ggaccaattt t gtcgacgct | 180 |
| gacgggatga ctgactctgt ctatcaaata aggcgtagta ctgggaaaga t gaagatatg | 240 |
| tccaatcctg tatcggtatg ggatgatgaa tatcttgcca tccctcttga t aagccagaa | 300 |
| ggaggagtca ctccggatgg tgtttcctat gaatatacag ccaatgatgc a gtgttgga | 360 |
| gatttagatg gggacgggca gtacgaaatt attttgaaat gggatccaac a aattcaaaa | 420 |
| gataactcac ggtctggtta tacagggaac gtttatcttg atgcgtataa a ttagatgga | 480 |
| acgaagcttt ggcgtctaga tttgggacga acattcgag ctggagccca t tatagccag | 540 |
| tttctcgtct atgattttga tggaaacggt cgttcagaag tagtcttaaa a acagcagac | 600 |
| ggaacgattg atggagttgg caacgtgata ggggatcaag acgccgatta t cgcaactca | 660 |
| tcaggttaca ttttagatgg tcctgaatac ttgacgatct ttctggga a acaggcgaa | 720 |
| gcgctagaca cgattgacta tgttccgcca cgtgggaatg tcagtgattg g ggcgacaat | 780 |
| tatggtaatc gtgtagaccg cttcctagca ggtgtggctt attagacgg a gaaagacca | 840 |
| agctttgtaa tggctagagg ctattatacg cgcacggtgc tagctgctta t caatgggac | 900 |
| gatgggaaaa taaagagca atgggtgttt gatagcaatg atccaggaaa t gaacgctat | 960 |
| gcagggcaag gtaaccatag tctagcaatc gcggatgtag acggtgatgg c aaggatgag | 1020 |
| attatctatg tgctatggt ggtggatcac gatggcactg gctttattc g actggctgg | 1080 |
| ggccatggag atgctaacca tgtgagcaac ctaaatccga atcgcaaagg g ttggagatt | 1140 |
| ttcagcctc atgaagactc gcgctctcct gtgggctacg gtattcggga t gcagagacg | 1200 |
| ggtgagctgc tctgggtga atttacaggg accgacgttg acggcgtt g gcagccgat | 1260 |
| attgatccgc gttttgatgg ggcagagcta tgggcatctg ctcaatggga t gggcgcgaa | 1320 |
| ggaagtggcc tattttccgt tgaaggcgaa tccattacga caaaaacccc a caatcggtt | 1380 |
| aattttgcga tttggtggac gggtgatttg ctgcgtgagc tccttgatca t tcctttgac | 1440 |
| ccgagcaaag atccgcatgg ggttggaaaa atcgagaagt gggattggga a aaggaagag | 1500 |
| ctagtggaga ttttcgttcc agaagggaca aggtcaaaca actggacgaa a ggtaaccca | 1560 |
| tccttacaag ccgacttgtt tgggattgg cggaggaag ttatttggcc a tctgctgat | 1620 |
| agtaacgagc tacgaatcta taccacgacc gaagaaacag agcaccgtat c ccaacactt | 1680 |
| atgcatgact ctgtctatcg tttgagtgtt gcttggcaaa atgtcggata t aatcagcca | 1740 |
| ccgcatacga gctacttcct cggccacggc atgaaggaag ccccgctacc a aaagtgcat | 1800 |

```
gcaggacaag tagtaccagt tgagctgaaa gcaaatcagc aagggaaaaa g aagctatcg      1860 gttcaagtga gattcgattc accaacggcg ggagaatccc tcgtatcatc a tctgtcaga      1920 ttattcgtca atggggaaac aatccaagca gagaaagtac acagg                       1965
```

<210> SEQ ID NO 14
<211> LENGTH: 655
<212> TYPE: PRT
<213> ORGANISM: Bacillus halodurans C4539

<400> SEQUENCE: 14

```
Met Leu Arg Gln Lys Glu Gln Leu Asp Arg G ly Leu Val Ala Val Lys
 1               5                  10                  15

Arg Ala Asp Gly Val Phe Leu Ser Trp Arg L eu Leu Gly Thr Glu His
            20                  25                  30

Pro Leu Thr Val Phe His Val Tyr Arg Asp G ly Glu Lys Ile Thr Lys
        35                  40                  45

Ala Gly Leu Gln Glu Gly Thr Asn Phe Val A sp Ala Asp Gly Met Thr
    50                  55                  60

Asp Ser Val Tyr Gln Ile Lys Ala Val Ala G ly Lys Asp Glu Asp Met
65                  70                  75                  80

Ser Asn Pro Val Ser Val Trp Asp Asp Glu T yr Leu Ala Ile Pro Leu
                85                  90                  95

Asp Lys Pro Glu Gly Gly Val Thr Pro Asp G ly Val Ser Tyr Glu Tyr
            100                 105                 110

Thr Ala Asn Asp Ala Ser Val Gly Asp Leu A sp Gly Asp Gly Gln Tyr
        115                 120                 125

Glu Ile Ile Leu Lys Trp Asp Pro Thr Asn S er Lys Asp Asn Ser Arg
    130                 135                 140

Ser Gly Tyr Thr Gly Asn Val Tyr Leu Asp A la Tyr Lys Leu Asp Gly
145                 150                 155                 160

Thr Lys Leu Trp Arg Leu Asp Leu Gly Arg A sn Ile Arg Ala Gly Ala
                165                 170                 175

His Tyr Ser Gln Phe Leu Val Tyr Asp Phe A sp Gly Asn Gly Arg Ser
            180                 185                 190

Glu Val Val Leu Lys Thr Ala Asp Gly Thr I le Asp Gly Val Gly Asn
        195                 200                 205

Val Ile Gly Asp Gln Asp Ala Asp Tyr Arg A sn Ser Ser Gly Tyr Ile
    210                 215                 220

Leu Asp Gly Pro Glu Tyr Leu Thr Ile Phe S er Gly Glu Thr Gly Glu
225                 230                 235                 240

Ala Leu Asp Thr Ile Asp Tyr Val Pro Pro A rg Gly Asn Val Ser Asp
                245                 250                 255

Trp Gly Asp Asn Tyr Gly Asn Arg Val Asp A rg Phe Leu Ala Gly Val
            260                 265                 270

Ala Tyr Leu Asp Gly Glu Arg Pro Ser Phe V al Met Ala Arg Gly Tyr
        275                 280                 285

Tyr Thr Arg Thr Val Leu Ala Ala Tyr Gln T rp Asp Asp Gly Lys Ile
    290                 295                 300

Lys Glu Gln Trp Val Phe Asp Ser Asn Asp P ro Gly Asn Glu Arg Tyr
305                 310                 315                 320

Ala Gly Gln Gly Asn His Ser Leu Ala Ile A la Asp Val Asp Gly Asp
                325                 330                 335

Gly Lys Asp Glu Ile Ile Tyr Gly Ala Met V al Val Asp His Asp Gly
            340                 345                 350
```

Thr Gly Leu Tyr Ser Thr Gly Trp Gly His Gly Asp Ala Asn His Val
        355                 360                 365

Ser Asn Leu Asn Pro Asn Arg Lys Gly Leu Glu Ile Phe Gln Pro His
    370                 375                 380

Glu Asp Ser Arg Ser Pro Val Gly Tyr Gly Ile Arg Asp Ala Glu Thr
385                 390                 395                 400

Gly Glu Leu Leu Trp Gly Glu Phe Thr Gly Thr Asp Val Gly Arg Ala
                405                 410                 415

Leu Ala Ala Asp Ile Asp Pro Arg Phe Asp Gly Ala Glu Leu Trp Ala
            420                 425                 430

Ser Ala Gln Trp Asp Gly Arg Glu Gly Ser Gly Leu Phe Ser Val Glu
        435                 440                 445

Gly Glu Ser Ile Thr Thr Lys Thr Pro Gln Ser Val Asn Phe Ala Ile
450                 455                 460

Trp Trp Thr Gly Asp Leu Leu Arg Glu Leu Leu Asp His Ser Phe Asp
465                 470                 475                 480

Pro Ser Lys Asp Pro His Gly Val Gly Lys Ile Glu Lys Trp Asp Trp
                485                 490                 495

Glu Lys Glu Glu Leu Val Glu Ile Phe Val Pro Glu Gly Thr Arg Ser
            500                 505                 510

Asn Asn Trp Thr Lys Gly Asn Pro Ser Leu Gln Ala Asp Leu Phe Gly
        515                 520                 525

Asp Trp Arg Glu Glu Val Ile Trp Pro Ser Ala Asp Ser Asn Glu Leu
    530                 535                 540

Arg Ile Tyr Thr Thr Thr Glu Glu Thr Glu His Arg Ile Pro Thr Leu
545                 550                 555                 560

Met His Asp Ser Val Tyr Arg Leu Ser Val Ala Trp Gln Asn Val Gly
                565                 570                 575

Tyr Asn Gln Pro Pro His Thr Ser Tyr Phe Leu Gly His Gly Met Lys
            580                 585                 590

Glu Ala Pro Leu Pro Lys Val His Ala Gly Gln Val Val Pro Val Glu
        595                 600                 605

Leu Lys Ala Asn Gln Gln Gly Lys Lys Lys Leu Ser Val Gln Val Arg
    610                 615                 620

Phe Asp Ser Pro Thr Ala Gly Glu Ser Leu Val Ser Ser Ser Val Arg
625                 630                 635                 640

Leu Phe Val Asn Gly Glu Thr Ile Gln Ala Glu Lys Val His Arg
                645                 650                 655

<210> SEQ ID NO 15
<211> LENGTH: 1896
<212> TYPE: DNA
<213> ORGANISM: Streptomyces coelicolor

<400> SEQUENCE: 15

```
gtgaggcacc cccacacccg cccccacgcc cccacccgc accgcagacg c ccacgcgcc      60 ctggccgcgg ccctcgccgc cgccgggctc tcggcgcgg gcctgacgac g ctggccccc     120 gacaccgccg aggccgccac ggcacgccag gtcgaggccc tggaccgggg c gtcgtcagc     180 gtccacaccg gcgacgggaa cctggtcagc tggcgctggc tgggcaccga c ccggacaac     240 gtcgcgttca acgtctaccg ggccggtacg aaggtcaact ccagcccgt c accggctcc     300 accacctact ccactccggg cgcgccctcc cacgccgact acaccgtccg c gcggtcgtg     360 aacggcacgg agcagggcga ctccgtccac gcgatccagt tccgggccgg c tacaaggac     420
```

-continued

```
gtaccgatca gcccgccctc cggcggcacc accccgacg gcgtctccta c acctacgag      480 gccaacgacg cctccgtcgg cgacctcgac ggcgacggcg ccctcgacct c gtcctcaag      540 tggcagccga ccaacgccaa ggacaactcc cagtccggct acaccggcaa c acggtcgtc      600 gacggcatca agctcgacgg cacccgcctg tggcgcgtcg acctgggccg c aacatccgc      660 tccggcgccc actacaccca gttccaggtg tacgactacg acggcgacgg c cgggccgag      720 gtcgccatga agaccgccga cggcaccaag gacggcaccg gcgcggtcat c ggcaactcc      780 tcggcggatc accgcaactc gagcggctac gtcctctccg ccccgaata c ctcaccatg      840 ttcaacggcc ggaccggcac cgcgatgggg accgtcgact acgtcccggc c cgcggctcg      900 gtctcctcct ggggcgactc ctacggcaac cgcgtcgacc ggttcctggc g ggcacggcg      960 tacctggacg gctcccgccc ctccgtgatt atggcgcgcg ggtactacac g cgcacggtg     1020 atcgcggcct gggactggcg ggacggccgg ttcacccgcc gctggacctt c gacaccaac     1080 tcctccacca acagcggcaa gggctacgac ggccagggca ccaccagct c tccgtcgcg     1140 gacgtggacg tgacggccg ggacgagatc gtctacggcg cgatggccgt c gacgacaac     1200 ggctacgccc tgtggaccac caggaacggc cacggcgacg ccatgcacgt c ggcgacctc     1260 gacccgtccc gggcgggcct ggaggagttc aaggtcgacg aggacggctc g aagccctcg     1320 tcgtacctgg cggacgcccg cacgggccag atcctctggt ccaccggcgc g agcggcgac     1380 aacggccgcg gtgtctccgg ggacatctgg tcgggcagcg cggcgccga g tcctggtcg     1440 tccgcggaga gcggcatccg caaccccaag ggcaccgtcg tcggcagccg c aagccctcc     1500 agcgccaact tcctttcctg gtgggacggc gacaccgtcc gtgaactcct c gacggcacc     1560 cacgtcgaca agtacggcac ctcgggcgac acccgcctgc tcaccggctc c ggcgtcgcc     1620 tccaacaacg gcaccaaggc caccccggtc ctggccggcg acatcctcgg c gactggcgc     1680 gaggaggtcg tctggcgcac gtcgaacaac acggccctgc gcatctactc c accccctac     1740 gacacggaca cccgcatcac gaccctcctc cacgacaccc agtaccgcac c gcactggcc     1800 tggcagaaca ccgcctacaa ccagccaccg caccccgagct tcttcctcgg a agcgggatg     1860 ccgacggccc cccggccgtc ggtccacacg ccctga                               1896
```

<210> SEQ ID NO 16
<211> LENGTH: 631
<212> TYPE: PRT
<213> ORGANISM: Streptomyces coelicolor

<400> SEQUENCE: 16

```
Val Arg His Pro His Thr Arg Pro His Ala P ro His Pro His Arg Arg
 1               5                  10                  15

Arg Pro Arg Ala Leu Ala Ala Ala Leu Ala A la Ala Gly Leu Leu Gly
            20                  25                  30

Ala Gly Leu Thr Thr Leu Ala Pro Asp Thr A la Glu Ala Ala Thr Ala
        35                  40                  45

Arg Gln Val Glu Ala Leu Asp Arg Gly Val V al Ser Val His Thr Gly
    50                  55                  60

Asp Gly Asn Leu Val Ser Trp Arg Trp Leu G ly Thr Asp Pro Asp Asn
65                  70                  75                  80

Val Ala Phe Asn Val Tyr Arg Ala Gly Thr L ys Val Asn Ser Ser Pro
                85                  90                  95

Val Thr Gly Ser Thr Thr Tyr Phe His Ser G ly Ala Pro Ser His Ala
            100                 105                 110
```

-continued

Asp Tyr Thr Val Arg Ala Val Asn Gly Thr Glu Gln Gly Asp Ser
            115                 120                 125

Val His Ala Ile Gln Phe Arg Ala Gly Tyr Lys Asp Val Pro Ile Ser
        130                 135                 140

Pro Pro Ser Gly Gly Thr Thr Pro Asp Gly Val Ser Tyr Thr Tyr Glu
145                 150                 155                 160

Ala Asn Asp Ala Ser Val Gly Asp Leu Asp Gly Asp Gly Ala Leu Asp
                165                 170                 175

Leu Val Leu Lys Trp Gln Pro Thr Asn Ala Lys Asp Asn Ser Gln Ser
            180                 185                 190

Gly Tyr Thr Gly Asn Thr Val Val Asp Gly Ile Lys Leu Asp Gly Thr
            195                 200                 205

Arg Leu Trp Arg Val Asp Leu Gly Arg Asn Ile Arg Ser Gly Ala His
        210                 215                 220

Tyr Thr Gln Phe Gln Val Tyr Asp Tyr Asp Gly Asp Gly Arg Ala Glu
225                 230                 235                 240

Val Ala Met Lys Thr Ala Asp Gly Thr Lys Asp Gly Thr Gly Ala Val
                245                 250                 255

Ile Gly Asn Ser Ser Ala Asp His Arg Asn Ser Ser Gly Tyr Val Leu
            260                 265                 270

Ser Gly Pro Glu Tyr Leu Thr Met Phe Asn Gly Arg Thr Gly Thr Ala
        275                 280                 285

Met Gly Thr Val Asp Tyr Val Pro Ala Arg Gly Ser Val Ser Ser Trp
    290                 295                 300

Gly Asp Ser Tyr Gly Asn Arg Val Asp Arg Phe Leu Ala Gly Thr Ala
305                 310                 315                 320

Tyr Leu Asp Gly Ser Arg Pro Ser Val Ile Met Ala Arg Gly Tyr Tyr
                325                 330                 335

Thr Arg Thr Val Ile Ala Ala Trp Asp Trp Arg Asp Gly Arg Phe Thr
            340                 345                 350

Arg Arg Trp Thr Phe Asp Thr Asn Ser Ser Thr Asn Ser Gly Lys Gly
        355                 360                 365

Tyr Asp Gly Gln Gly Asn His Gln Leu Ser Val Ala Asp Val Asp Gly
    370                 375                 380

Asp Gly Arg Asp Glu Ile Val Tyr Gly Ala Met Ala Val Asp Asp Asn
385                 390                 395                 400

Gly Tyr Ala Leu Trp Thr Thr Arg Asn Gly His Gly Asp Ala Met His
                405                 410                 415

Val Gly Asp Leu Asp Pro Ser Arg Ala Gly Leu Glu Glu Phe Lys Val
            420                 425                 430

Asp Glu Asp Gly Ser Lys Pro Ser Ser Tyr Leu Ala Asp Ala Arg Thr
        435                 440                 445

Gly Gln Ile Leu Trp Ser Thr Gly Ala Ser Gly Asp Asn Gly Arg Gly
    450                 455                 460

Val Ser Gly Asp Ile Trp Ser Gly Ser Ala Gly Ala Glu Ser Trp Ser
465                 470                 475                 480

Ser Ala Glu Ser Gly Ile Arg Asn Pro Lys Gly Thr Val Val Gly Ser
                485                 490                 495

Arg Lys Pro Ser Ser Ala Asn Phe Leu Ser Trp Trp Asp Gly Asp Thr
            500                 505                 510

Val Arg Glu Leu Leu Asp Gly Thr His Val Asp Lys Tyr Gly Thr Ser
        515                 520                 525

Gly Asp Thr Arg Leu Leu Thr Gly Ser Gly V al Ala Ser Asn Asn Gly
          530                 535                 540

Thr Lys Ala Thr Pro Val Leu Ala Gly Asp I le Leu Gly Asp Trp Arg
545                 550                 555                 560

Glu Glu Val Val Trp Arg Thr Ser Asn Asn T hr Ala Leu Arg Ile Tyr
                565                 570                 575

Ser Thr Pro Tyr Asp Thr Asp Thr Arg Ile T hr Thr Leu Leu His Asp
          580                 585                 590

Thr Gln Tyr Arg Thr Ala Leu Ala Trp Gln A sn Thr Ala Tyr Asn Gln
          595                 600                 605

Pro Pro His Pro Ser Phe Phe Leu Gly Ser G ly Met Pro Thr Ala Pro
          610                 615                 620

Arg Pro Ser Val His Thr Pro
625                 630

<210> SEQ ID NO 17
<211> LENGTH: 1168
<212> TYPE: DNA
<213> ORGANISM: Bacillus halodurans KJ59

<400> SEQUENCE: 17

| | | | | | |
|---|---|---|---|---|---|
| atgaacaagt | tagggatgtg | gttctctgga | ttgatcttag | tagttggtct | attggtcgga | 60 |
| gggaacgaag | cgaaggcaaa | tgaagtggtg | aatgcaaggg | attttggtgc | g actccaggg | 120 |
| gtagcaacct | cacaaacaaa | tgcgcttcat | gcggcgatgc | gtcatttta | t gatcgcggg | 180 |
| gtgcaaggaa | cggtctatat | tccggcggga | acttattcaa | ttgacgaagc | g ctcaggttt | 240 |
| cactcaggtg | taaacatcgt | tggtgatggg | atgggaagga | ccattttaaa | g aagacagga | 300 |
| aacagtaaca | attatgtggt | tggcaatccc | attatgagag | ggtcgaacaa | c ctcaatgtg | 360 |
| acggtttcta | atttaacgat | tgatgccgat | cgaacgaacc | gagcgcagcg | g ggattaggg | 420 |
| caagtcgggg | gcatgaatct | tgacgcggat | gtgagcaatt | taacgttaga | g cgtgtcgaa | 480 |
| gtacgtgatg | ccacgattgg | gctttttatta | agacggttaa | aaaactcggt | t gttagagat | 540 |
| agtgtgatcg | acaatacgac | tggtcatggg | atcgcatttg | gtcatgaaaa | t catccgatt | 600 |
| ggagatgttc | gcaacaacct | tattacagga | aaccgaatta | cgaattctac | t ggcggtagt | 660 |
| gggattaacc | tgtcacgggc | cacgtatacg | actgttaccc | ataaccaagt | g ataaatgat | 720 |
| cgacaacagg | atgactcgta | tggtggcatt | cgaattccaa | atggtgggga | g cataatacg | 780 |
| gttgaatata | atacgattcg | aaactatcca | cgaggaatct | ttgtattaag | c ggtgcaagg | 840 |
| cataaccaaa | tcaatcataa | caccgtcatt | gattcgagaa | ttcatggagt | g ttgatccaa | 900 |
| gctgatcata | acacgcttcg | tgaaaaccgg | attcagcagc | ttaacagctc | g ttaaatccg | 960 |
| gagtcggtgg | ttcgcatcgc | cccgggtagc | aataattcca | ttctcaataa | c aacatccaa | 1020 |
| gcccattcga | actttcgaaa | tatcgggatt | cgggtgacgg | gggattcgaa | c aacaatgtg | 1080 |
| attcgcaata | accgaatcgg | cacccaaggc | acacttgtaa | gtatagaagg | t gggcgtaac | 1140 |
| aatgtgaatg | aagggaacgt | acgacaat | | | | 1168 |

<210> SEQ ID NO 18
<211> LENGTH: 389
<212> TYPE: PRT
<213> ORGANISM: Bacillus halodurans KJ59

<400> SEQUENCE: 18

Met Asn Lys Leu Gly Met Trp Phe Ser Gly L eu Ile Leu Val Val Gly
 1               5                  10                  15

-continued

```
Leu Leu Val Gly Gly Asn Glu Ala Lys Ala Asn Glu Val Val Asn Ala
             20                  25                  30

Arg Asp Phe Gly Ala Thr Pro Gly Val Ala Thr Ser Gln Thr Asn Ala
         35                  40                  45

Leu His Ala Ala Met Arg His Phe Tyr Asp Arg Gly Val Gln Gly Thr
     50                  55                  60

Val Tyr Ile Pro Ala Gly Thr Tyr Ser Ile Asp Glu Ala Leu Arg Phe
 65                  70                  75                  80

His Ser Gly Val Asn Ile Val Gly Asp Gly Met Gly Arg Thr Ile Leu
                 85                  90                  95

Lys Lys Thr Gly Asn Ser Asn Tyr Val Val Gly Asn Pro Ile Met
            100                 105                 110

Arg Gly Ser Asn Asn Leu Asn Val Thr Val Ser Asn Leu Thr Ile Asp
            115                 120                 125

Ala Asp Arg Thr Asn Arg Ala Gln Arg Gly Leu Gly Gln Val Gly Gly
        130                 135                 140

Met Asn Leu Asp Ala Asp Val Ser Asn Leu Thr Leu Glu Arg Val Glu
145                 150                 155                 160

Val Arg Asp Ala Thr Ile Gly Leu Leu Leu Arg Arg Leu Lys Asn Ser
                165                 170                 175

Val Val Arg Asp Ser Val Ile Asp Asn Thr Thr Gly His Gly Ile Ala
            180                 185                 190

Phe Gly His Glu Asn His Pro Ile Gly Asp Val Arg Asn Asn Leu Ile
        195                 200                 205

Thr Gly Asn Arg Ile Thr Asn Ser Thr Gly Gly Ser Gly Ile Asn Leu
    210                 215                 220

Ser Arg Ala Thr Tyr Thr Thr Val Thr His Asn Gln Val Ile Asn Asp
225                 230                 235                 240

Arg Gln Gln Asp Asp Ser Tyr Gly Gly Ile Arg Ile Pro Asn Gly Gly
                245                 250                 255

Glu His Asn Thr Val Glu Tyr Asn Thr Ile Arg Asn Tyr Pro Arg Gly
            260                 265                 270

Ile Phe Val Leu Ser Gly Ala Arg His Asn Gln Ile Asn His Asn Thr
        275                 280                 285

Val Ile Asp Ser Arg Ile His Gly Val Leu Ile Gln Ala Asp His Asn
    290                 295                 300

Thr Leu Arg Glu Asn Arg Ile Gln Gln Leu Asn Ser Ser Leu Asn Pro
305                 310                 315                 320

Glu Ser Val Val Arg Ile Ala Pro Gly Ser Asn Asn Ser Ile Leu Asn
                325                 330                 335

Asn Asn Ile Gln Ala His Ser Asn Phe Arg Asn Ile Gly Ile Arg Val
            340                 345                 350

Thr Gly Asp Ser Asn Asn Val Ile Arg Asn Asn Arg Ile Gly Thr
        355                 360                 365

Gln Gly Thr Leu Val Ser Ile Glu Gly Gly Arg Asn Asn Val Asn Glu
    370                 375                 380

Gly Asn Val Arg Gln
385

<210> SEQ ID NO 19
<211> LENGTH: 507
<212> TYPE: DNA
<213> ORGANISM: Bacillus agaradhaerens
<220> FEATURE:
```

```
<221> NAME/KEY: misc_feature
<222> LOCATION: (1)...(507)
<223> OTHER INFORMATION: n= a, c, g or t

<400> SEQUENCE: 19
agatttttgg gaccgaggcc caggtgtttc aggcaaagcc aaacggatgc c attacatgc      60 agcgatgcgt tatttctatg atagaggtgt tagagggaaa ccgtctatt t g ccggcgggc   120 acatattcag tggatagcgc cttacgcttt catcaagggg ttaatcttgt g ggagatggt   180 gtaggacgaa caatcattaa aaagtaggc agccaaaata attatgttgt a ggtaaccct    240 atttttcgtg gggggacgac taatcttaat gtgacagtct ctcacatcac c tttgatgca   300 gatcggacaa accgtgcgtc tcaaggtctt ggacaagtag gtgggacttg g agaacagtt   360 tactgcgctc gtatccaatt taacgttgga acacatagaa gtaagggatg c cactattgg   420 tntgcttgtt agaaggtaga gattctgtta tttcagacag ccttantgat c ggacgagtn   480 ggcatggtat tgccacaggg agtgaat                                          507

<210> SEQ ID NO 20
<211> LENGTH: 169
<212> TYPE: PRT
<213> ORGANISM: Bacillus agaradhaerens
<220> FEATURE:
<221> NAME/KEY: VARIANT
<222> LOCATION: 147
<223> OTHER INFORMATION: Xaa = any amino acid

<400> SEQUENCE: 20

Arg Asp Phe Trp Asp Arg Gly Pro Gly Val S er Gly Lys Ala Lys Arg
 1               5                  10                  15

Met Pro Leu His Ala Ala Met Arg Tyr Phe T yr Asp Arg Gly Val Arg
             20                  25                  30

Gly Lys Thr Val Tyr Leu Pro Ala Gly Thr T yr Ser Val Asp Ser Ala
         35                  40                  45

Leu Arg Phe His Gln Gly Val Asn Leu Val G ly Asp Gly Val Gly Arg
     50                  55                  60

Thr Ile Ile Lys Lys Val Gly Ser Gln Asn A sn Tyr Val Val Gly Asn
65                  70                  75                  80

Pro Ile Phe Arg Gly Gly Thr Thr Asn Leu A sn Val Thr Val Ser His
                 85                  90                  95

Ile Thr Phe Asp Ala Asp Arg Thr Asn Arg A la Ser Gln Gly Leu Gly
            100                 105                 110

Gln Val Gly Gly Thr Gly Glu Gln Phe Thr A la Leu Val Ser Asn Leu
        115                 120                 125

Thr Leu Glu His Ile Glu Val Arg Asp Ala T hr Ile Gly Leu Leu Val
    130                 135                 140

Arg Arg Xaa Arg Ser Val Ile Ser Asp Ser L eu Ile Asp Arg Thr Ser
145                 150                 155                 160

Trp His Gly Ile Ala Thr Gly Ser Glu
                165

<210> SEQ ID NO 21
<211> LENGTH: 22
<212> TYPE: PRT
<213> ORGANISM: Microbial
<220> FEATURE:
<221> NAME/KEY: VARIANT
<222> LOCATION: 11
<223> OTHER INFORMATION: Xaa= Met or Leu
<221> NAME/KEY: VARIANT
```

```
<222> LOCATION: 15
<223> OTHER INFORMATION: Xaa= Phe or Leu

<400> SEQUENCE: 21

Asn Ile Arg Ala Gly Ala His Thr Gln Phe Xaa Val Tyr Asp Xaa Asp
 1               5                  10                  15
Gly Asp Gly Lys Ala Glu
            20

<210> SEQ ID NO 22
<211> LENGTH: 11
<212> TYPE: PRT
<213> ORGANISM: Microbial

<400> SEQUENCE: 22

Tyr Gly Asn Arg Val Asp Arg Phe Leu Ala Gly
 1               5                  10

<210> SEQ ID NO 23
<211> LENGTH: 17
<212> TYPE: PRT
<213> ORGANISM: Microbial
<220> FEATURE:
<221> NAME/KEY: VARIANT
<222> LOCATION: 12
<223> OTHER INFORMATION: Xaa= any amino acid

<400> SEQUENCE: 23

Tyr Gly Asn Arg Val Asp Arg Phe Leu Ala Gly Xaa Ala Tyr Leu Asp
 1               5                  10                  15
Gly

<210> SEQ ID NO 24
<211> LENGTH: 22
<212> TYPE: PRT
<213> ORGANISM: Microbial
<220> FEATURE:
<221> NAME/KEY: VARIANT
<222> LOCATION: 7
<223> OTHER INFORMATION: Xaa= Asn or Ser
<221> NAME/KEY: VARIANT
<222> LOCATION: 10
<223> OTHER INFORMATION: Xaa= Ile or Val

<400> SEQUENCE: 24

Ala Gly Gln Gly Asn His Xaa Leu Ser Xaa Ala Asp Val Asp Gly Asp
 1               5                  10                  15
Gly Lys Asp Glu Ile Ile
            20

<210> SEQ ID NO 25
<211> LENGTH: 22
<212> TYPE: PRT
<213> ORGANISM: Microbial
<220> FEATURE:
<221> NAME/KEY: VARIANT
<222> LOCATION: 7
<223> OTHER INFORMATION: Xaa= Asn or Ser
<221> NAME/KEY: VARIANT
<222> LOCATION: 9
<223> OTHER INFORMATION: Xaa= Ser or Ala
<221> NAME/KEY: VARIANT
<222> LOCATION: 10
<223> OTHER INFORMATION: Xaa= Ile or Val

<400> SEQUENCE: 25

Ala Gly Gln Gly Asn His Xaa Leu Xaa Xaa Ala Asp Val Asp Gly Asp
```

```
                1               5                  10                 15

Gly Lys Asp Glu Ile Ile
                20

<210> SEQ ID NO 26
<211> LENGTH: 10
<212> TYPE: PRT
<213> ORGANISM: Microbial

<400> SEQUENCE: 26

Glu Val Arg Asp Ala Thr Ile Gly Leu Leu
  1               5                  10

<210> SEQ ID NO 27
<211> LENGTH: 9
<212> TYPE: PRT
<213> ORGANISM: Microbial

<400> SEQUENCE: 27

Asn Asn Tyr Val Val Gly Asn Pro Ile
  1               5

<210> SEQ ID NO 28
<211> LENGTH: 8
<212> TYPE: PRT
<213> ORGANISM: Microbial

<400> SEQUENCE: 28

Asp Ala Asp Arg Thr Asn Arg Ala
  1               5

<210> SEQ ID NO 29
<211> LENGTH: 6
<212> TYPE: PRT
<213> ORGANISM: Microbial

<400> SEQUENCE: 29

Ser Ala Asn Asp Ala Ser
  1               5

<210> SEQ ID NO 30
<211> LENGTH: 11
<212> TYPE: PRT
<213> ORGANISM: Microbial
<220> FEATURE:
<221> NAME/KEY: VARIANT
<222> LOCATION: 6
<223> OTHER INFORMATION: Xaa= Ser or Thr

<400> SEQUENCE: 30

Leu Lys Trp Asp Pro Xaa Asn Ser Lys Asp Asn
  1               5                  10

<210> SEQ ID NO 31
<211> LENGTH: 8
<212> TYPE: PRT
<213> ORGANISM: Microbial
<220> FEATURE:
<221> NAME/KEY: VARIANT
<222> LOCATION: 6
<223> OTHER INFORMATION: Xaa= Asp or Asn

<400> SEQUENCE: 31

Asp Ala Tyr Lys Leu Xaa Gly Thr
  1               5
```

```
<210> SEQ ID NO 32
<211> LENGTH: 22
<212> TYPE: PRT
<213> ORGANISM: Microbial
<220> FEATURE:
<221> NAME/KEY: VARIANT
<222> LOCATION: 11
<223> OTHER INFORMATION: Xaa= Met or Leu
<221> NAME/KEY: VARIANT
<222> LOCATION: 15
<223> OTHER INFORMATION: Xaa= Phe or Leu

<400> SEQUENCE: 32

Asn Ile Arg Ala Gly Ala His Thr Gln Phe Xaa Val Tyr Asp Xaa Asp
 1               5                  10                  15

Gly Asp Gly Lys Ala Glu
            20

<210> SEQ ID NO 33
<211> LENGTH: 6
<212> TYPE: PRT
<213> ORGANISM: Microbial

<400> SEQUENCE: 33

Lys Thr Ala Asp Gly Thr
 1               5

<210> SEQ ID NO 34
<211> LENGTH: 9
<212> TYPE: PRT
<213> ORGANISM: Microbial
<220> FEATURE:
<221> NAME/KEY: VARIANT
<222> LOCATION: 6
<223> OTHER INFORMATION: Xaa= Tyr or Phe

<400> SEQUENCE: 34

Leu Ser Gly Pro Glu Xaa Leu Thr Val
 1               5

<210> SEQ ID NO 35
<211> LENGTH: 11
<212> TYPE: PRT
<213> ORGANISM: Microbial

<400> SEQUENCE: 35

Tyr Gly Asn Arg Val Asp Arg Phe Leu Ala Gly
 1               5                  10

<210> SEQ ID NO 36
<211> LENGTH: 17
<212> TYPE: PRT
<213> ORGANISM: Microbial
<220> FEATURE:
<221> NAME/KEY: VARIANT
<222> LOCATION: 12
<223> OTHER INFORMATION: Xaa= any amino acid

<400> SEQUENCE: 36

Tyr Gly Asn Arg Val Asp Arg Phe Leu Ala Gly Xaa Ala Tyr Leu Asp
 1               5                  10                  15

Gly

<210> SEQ ID NO 37
<211> LENGTH: 22
<212> TYPE: PRT
```

```
<213> ORGANISM: Microbial
<220> FEATURE:
<221> NAME/KEY: VARIANT
<222> LOCATION: 7
<223> OTHER INFORMATION: Xaa=Asn or Ser
<221> NAME/KEY: VARIANT
<222> LOCATION: 10
<223> OTHER INFORMATION: Xaa= Ile or Val

<400> SEQUENCE: 37

Ala Gly Gln Gly Asn His Xaa Leu Ser Xaa A la Asp Val Asp Gly Asp
 1               5                  10                  15

Gly Lys Asp Glu Ile Ile
            20

<210> SEQ ID NO 38
<211> LENGTH: 22
<212> TYPE: PRT
<213> ORGANISM: Microbial
<220> FEATURE:
<221> NAME/KEY: VARIANT
<222> LOCATION: 7
<223> OTHER INFORMATION: Xaa= Asn or Ser
<221> NAME/KEY: VARIANT
<222> LOCATION: 9
<223> OTHER INFORMATION: Xaa=Ser or Ala
<221> NAME/KEY: VARIANT
<222> LOCATION: 10
<223> OTHER INFORMATION: Xaa= Ile or Val

<400> SEQUENCE: 38

Ala Gly Gln Gly Asn His Xaa Leu Xaa Xaa A la Asp Val Asp Gly Asp
 1               5                  10                  15

Gly Lys Asp Glu Ile Ile
            20

<210> SEQ ID NO 39
<211> LENGTH: 7
<212> TYPE: PRT
<213> ORGANISM: Mirobial

<400> SEQUENCE: 39

Leu Arg Ile Tyr Thr Thr Thr
 1               5

<210> SEQ ID NO 40
<211> LENGTH: 6
<212> TYPE: PRT
<213> ORGANISM: Microbial

<400> SEQUENCE: 40

Tyr Thr Leu Met His Asp
 1               5

<210> SEQ ID NO 41
<211> LENGTH: 17
<212> TYPE: PRT
<213> ORGANISM: Microbial
<220> FEATURE:
<221> NAME/KEY: VARIANT
<222> LOCATION: 1
<223> OTHER INFORMATION: Xaa= Tyr or Pro
<221> NAME/KEY: VARIANT
<222> LOCATION: 7
<223> OTHER INFORMATION: Xaa= Pro or Ser
<221> NAME/KEY: VARIANT
<222> LOCATION: 12
<223> OTHER INFORMATION: Xaa= Ser or Gly
```

<400> SEQUENCE: 41

Xaa Thr Leu Met His Asp Xaa Val Tyr Arg Leu Xaa Ile Ala Trp Gln
1               5                   10                  15
Asn

<210> SEQ ID NO 42
<211> LENGTH: 10
<212> TYPE: PRT
<213> ORGANISM: Microbial
<220> FEATURE:
<221> NAME/KEY: VARIANT
<222> LOCATION: 5
<223> OTHER INFORMATION: Xaa= Ser or Gly

<400> SEQUENCE: 42

Val Tyr Arg Leu Xaa Ile Ala Trp Gln Asn
1               5                   10

<210> SEQ ID NO 43
<211> LENGTH: 10
<212> TYPE: PRT
<213> ORGANISM: Microbial

<400> SEQUENCE: 43

Glu Val Arg Asp Ala Thr Ile Gly Leu Leu
1               5                   10

<210> SEQ ID NO 44
<211> LENGTH: 9
<212> TYPE: PRT
<213> ORGANISM: Microbial

<400> SEQUENCE: 44

Asn Asn Tyr Val Val Gly Asn Pro Ile
1               5

<210> SEQ ID NO 45
<211> LENGTH: 8
<212> TYPE: PRT
<213> ORGANISM: Microbial

<400> SEQUENCE: 45

Asp Ala Asp Arg Thr Asn Arg Ala
1               5

<210> SEQ ID NO 46
<211> LENGTH: 42
<212> TYPE: DNA
<213> ORGANISM: Artificial Sequence
<220> FEATURE:
<223> OTHER INFORMATION: Primer

<400> SEQUENCE: 46
gtcgccgggg cggccgctat caattggtaa ctgtatctca gc                           42

<210> SEQ ID NO 47
<211> LENGTH: 64
<212> TYPE: DNA
<213> ORGANISM: Artificial Sequence
<220> FEATURE:
<223> OTHER INFORMATION: Primer

<400> SEQUENCE: 47
gtcgcccggg agctctgatc aggtaccaag cttgtcgacc tgcagaatga g gcagcaaga       60

```
agat                                                            64

<210> SEQ ID NO 48
<211> LENGTH: 61
<212> TYPE: DNA
<213> ORGANISM: Artificial Sequence
<220> FEATURE:
<223> OTHER INFORMATION: Primer

<400> SEQUENCE: 48
gtcggcggcc gctgatcacg taccaagctt gtcgacctgc agaatgaggc a gcaagaaga    60
t                                                               61

<210> SEQ ID NO 49
<211> LENGTH: 35
<212> TYPE: DNA
<213> ORGANISM: Artificial Sequence
<220> FEATURE:
<223> OTHER INFORMATION: Primer

<400> SEQUENCE: 49
gtcggagctc tatcaattgg taactgtatc tcagc                          35

<210> SEQ ID NO 50
<211> LENGTH: 35
<212> TYPE: DNA
<213> ORGANISM: Artificial Sequence
<220> FEATURE:
<223> OTHER INFORMATION: Primer

<400> SEQUENCE: 50
aacagctgat cacgactgat cttttagctt ggcac                          35

<210> SEQ ID NO 51
<211> LENGTH: 37
<212> TYPE: DNA
<213> ORGANISM: Artificial Sequence
<220> FEATURE:
<223> OTHER INFORMATION: Primer

<400> SEQUENCE: 51
aactgcagcc gcggcacatc ataatgggac aaatggg                        37

<210> SEQ ID NO 52
<211> LENGTH: 38
<212> TYPE: DNA
<213> ORGANISM: Artificial Sequence
<220> FEATURE:
<223> OTHER INFORMATION: Primer

<400> SEQUENCE: 52
tcgccggaat tcgtgcagtg tccgaaatag gcagatgc                       38

<210> SEQ ID NO 53
<211> LENGTH: 37
<212> TYPE: DNA
<213> ORGANISM: Artificial Sequence
<220> FEATURE:
<223> OTHER INFORMATION: Primer

<400> SEQUENCE: 53
tcgccggcat gcgttctgtc tgtaccgcaa tcaaacc                        37

<210> SEQ ID NO 54
<211> LENGTH: 34
```

```
<212> TYPE: DNA
<213> ORGANISM: Artificial Sequence
<220> FEATURE:
<223> OTHER INFORMATION: Primer

<400> SEQUENCE: 54
gcagccgcgg cagaaggggc agcgcggcag atgg                          34

<210> SEQ ID NO 55
<211> LENGTH: 39
<212> TYPE: DNA
<213> ORGANISM: Artificial Sequence
<220> FEATURE:
<223> OTHER INFORMATION: Primer

<400> SEQUENCE: 55
tcgccggcgg ccgcgttctg tctgtaccgc aatcaaacc                     39

<210> SEQ ID NO 56
<211> LENGTH: 45
<212> TYPE: DNA
<213> ORGANISM: Artificial Sequence
<220> FEATURE:
<223> OTHER INFORMATION: Primer

<400> SEQUENCE: 56
ctcgctgcag cagcggcggc acccagacag gcggagaaca ttagc              45

<210> SEQ ID NO 57
<211> LENGTH: 37
<212> TYPE: DNA
<213> ORGANISM: Artificial Sequence
<220> FEATURE:
<223> OTHER INFORMATION: Primer

<400> SEQUENCE: 57
cgacgacgtg cggccgccat tatgcgcctg ctcttcg                       37

<210> SEQ ID NO 58
<211> LENGTH: 34
<212> TYPE: DNA
<213> ORGANISM: Artificial Sequence
<220> FEATURE:
<223> OTHER INFORMATION: Primer

<400> SEQUENCE: 58
gcagccgcgg cagacgggcg gacggctgcg cagg                          34

<210> SEQ ID NO 59
<211> LENGTH: 87
<212> TYPE: DNA
<213> ORGANISM: Artificial Sequence
<220> FEATURE:
<223> OTHER INFORMATION: Primer

<400> SEQUENCE: 59
gtgggcggcc gcgcctgaga aaatccgtag ccagcaccgc gctctgcagc a gcggcgaaa    60 tgaagtggtg aatgcaaggg attttgg                                  87

<210> SEQ ID NO 60
<211> LENGTH: 49
<212> TYPE: DNA
<213> ORGANISM: Artificial Sequence
<220> FEATURE:
<223> OTHER INFORMATION: Primer
```

```
<400> SEQUENCE: 60
gcgctctgca gcagcggcga aatgaagtgg tgaatgcaag ggattttgg                    49

<210> SEQ ID NO 61
<211> LENGTH: 43
<212> TYPE: DNA
<213> ORGANISM: Artificial Sequence
<220> FEATURE:
<223> OTHER INFORMATION: Primer

<400> SEQUENCE: 61
gtcaggcgtg cggccgcggt gtagaggtgc gatgatggat ggg                          43
```